(12) United States Patent
Yuan et al.

(10) Patent No.: US 12,122,784 B2
(45) Date of Patent: Oct. 22, 2024

(54) PREPARATION METHOD FOR ECTEINASCIDIN COMPOUND AND INTERMEDIATE THEREOF

(71) Applicant: BRIGHTGENE BIO-MEDICAL TECHNOLOGY CO., LTD., Suzhou (CN)

(72) Inventors: Jiandong Yuan, Suzhou (CN); Xinliang Fu, Suzhou (CN); Zhanli Sun, Suzhou (CN); Xiaopei Xing, Suzhou (CN); Jingcheng Hui, Suzhou (CN); Qilei Cong, Suzhou (CN)

(73) Assignee: BRIGHTGENE BIO-MEDICAL TECHNOLOGY CO., LTD., Jiangsu (CN)

( * ) Notice: Subject to any disclaimer, the term of this patent is extended or adjusted under 35 U.S.C. 154(b) by 407 days.

(21) Appl. No.: 17/283,012

(22) PCT Filed: Aug. 26, 2019

(86) PCT No.: PCT/CN2019/102565
§ 371 (c)(1),
(2) Date: Apr. 5, 2021

(87) PCT Pub. No.: WO2020/155613
PCT Pub. Date: Aug. 6, 2020

(65) Prior Publication Data
US 2021/0355132 A1 Nov. 18, 2021

(30) Foreign Application Priority Data
Feb. 1, 2019 (CN) .......................... 201910101895.0

(51) Int. Cl.
*C07D 487/18* (2006.01)
*C07D 515/22* (2006.01)

(52) U.S. Cl.
CPC .......... *C07D 487/18* (2013.01); *C07D 515/22* (2013.01)

(58) Field of Classification Search
CPC ........................... C07D 487/18; C07D 515/22
See application file for complete search history.

(56) References Cited

U.S. PATENT DOCUMENTS

| 5,721,362 | A | 2/1998 | Corey et al. |
| 2004/0002602 | A1 | 1/2004 | Francesch |
| 2008/0045713 | A1 | 2/2008 | Cuevas et al. |
| 2013/0066067 | A1 | 3/2013 | Martin López et al. |

FOREIGN PATENT DOCUMENTS

| CN | 1237974 | A | 12/1999 |
| CN | 1360588 | A | 7/2002 |
| CN | 100475822 | C | 4/2009 |
| CN | 107033164 | A | 8/2017 |
| CN | 107522698 | A | 12/2017 |
| WO | 2000018233 | A1 | 4/2000 |
| WO | 2007045686 | A2 | 4/2007 |
| WO | WO2001087895 | A1 | 11/2011 |
| WO | 2011147828 | A1 | 12/2011 |

OTHER PUBLICATIONS

Second Office Action Issued in Corresponding Application No. EP 19 913 508.8 mailed Oct. 13, 2022, 4 pages.
Cuevas and Francesch, "Chapter 1: Semisynthesis Approach of Ecteinascidin 743 (ET-743, Yondelis®)," Drug Discovery from Natural Products (Genilloud and Vicente eds.). 2012;5-16.
Extended European Search Report from EP 19913508.8, dated Mar. 17, 2022.
Libretexts, "20.05.1: Alkylation of Amines by Alkyl Halides," Mar. 17, 2015.
Loudon, "23.7 Alkylation and Acylation Reactions of Amines," Organic Chemistry (5th ed.). 2009;1131-9.
Nokami et al., "Synthesis of Ionic Liquids Equipped with 2-Methoxyethoxymethyl/Methoxymethyl Groups Using a Simple Microreactor System," Org Process Res Dev. 2014; 18(11):1367-71.
Reusch, "Chemistry of Amines," May 5, 2013: https://www2.chemistry.msu.edu/faculty/reusch/virttxtjml/amine1.htm.
Sakai et al., "Ecteinascidins: Putative Biosynthetic Precursors and Absolute Stereochemistry," J Am Chem Soc. 1996;118(38):9017-23.
Warriner, "Houben-Weyl methods of molecular transformations—Science of synthesis—Compounds with two carbon-heteroatom bonds: Acetals : Hal/X and O/O, S, Se, Te," Georg Thieme Verlag, Stuttgart. 2007;vol. 29:321-2.
Wuts, "Methoxymethyl Ether (MOM Ether)," Greene's Protective Groups in Organic Synthesis (5th ed.). 2014;489.
Extended European Search Report dated Jul. 5, 2021 in connection with EP19913508.8 (12 pages).
Chen et al., 2006 "Total Synthesis of Ecteinascidin 743," J Am Chem Soc 128(1):87-89.
Corey et al., 1996 "Enantioselective Total Synthesis of Ecteinascidin 743," J Am Chem Soc 118(38):9202-9203.
Cuevas et al., 2000 "Synthesis of Ecteinascidin ET-743 and Phthalascidin Pt-650 from Cyanosafracin B," Org Lett 2 (16):2545-48.
Kawagishi et al., 2013 "Total Synthesis of Ecteinascidin 743," J Am Chem Soc 135(37):13684-87.
Menchaca et al., 2003 "Synthesis of Natural Ecteinascidins (ET-729, ET-745, ET-759B, ET-736, ET-637, ET-594) from Cyanosafracin B," J Org Chem 68(23):8859-66.

(Continued)

*Primary Examiner* — Timothy R Rozof
(74) *Attorney, Agent, or Firm* — DINSMORE & SHOHL LLP

(57) ABSTRACT

The present invention provides a method for preparing an ecteinascidin compound and an intermediate thereof, and specifically provides a preparation method for a novel compound QT9, and a method of using QT9 to prepare an ecteinascidin compound. The method provided by the present invention has high reaction selectivity and high yield, the obtained compound is easy to purify, and defects in the prior art that multiple intermediates are oily substances, and the reaction selectivity is poor are solved. The method of the present invention is particularly applicable to industrial production.

25 Claims, No Drawings

(56) References Cited

OTHER PUBLICATIONS

Rath et al., 2000 "Meta-omic Characterization of the Marine Invertebrate Microbial Consortium That Produces the Chemotherapeutic Natural Product ET-743," ACS Chem Biol 6(11):1244-56.
Xu et al., 2017 "A Concise and Practical Semisynthesis of Ecteinascidin 743 and (-)-Jorumycin," Eur J Org Chem 5:975-983.
International Search Report from related Application No. PCT/CN2019/102565, mailed Dec. 3, 2019 (12 pages).
Written Opinion from related Application No. PCT/CN2019/102565, mailed Dec. 3, 2019 (12 pages).

PREPARATION METHOD FOR ECTEINASCIDIN COMPOUND AND INTERMEDIATE THEREOF

1. TECHNICAL FIELD

The present invention belongs to the technical field of medicine, and in particular relates to a method for preparing an ecteinascidin compound and an intermediate thereof.

2. BACKGROUND

Ecteinascidin-743 (ET743), also known as trabectedin, is a class of active natural products with unique structures and is a first marine-derived anti-tumor drug from the tunicate *Ecteinascidia turbinata*, which is a semi-synthetic product of tetrahydroquinoline alkaloids extracted from ascidians. In addition to arresting the differentiation of tumor cells at the G1/G2 phase, ecteinascidin-743 can also inhibit the secretion of vascular endothelial growth factor (VEGF) and the expression of a receptor thereof. Trabectedin was approved by the European Union in September 2007 for the treatment of soft tissue sarcomas for which anthracyclines and ifosfamide treatments fail, or patients who are not suitable for receiving these two drugs; and trabectedin is combined with an azithromycin liposome for the treatment of platinum-sensitive ovarian cancer.

Studies have shown that in terms of anti-tumor activity, trabectedin is higher than well-known anticancer drugs such as camptothecin, paclitaxel, doxorubicin, bleomycin, cisplatin and etoposide, which are currently widely used in the clinic, by 1 to 3 orders of magnitude and has a unique multiple mechanism of action.

At present, the main methods for preparing trabectedin include a biological extraction method, wherein the highest yield of trabectedin is 0.0001% (ACS Chem. Biol. 2011, 6, 1244), which is very low in preparation and cannot satisfy industrial use. Corey et al. reported a total synthesis method for totally synthesizing trabectedin through 36 steps of reaction (J. Am. Chem. Soc. 1996, 118, 9202-9203), which method has cumbersome steps and requires the use of an expensive chiral ligand and noble metal ruthenium for the reactions, as well as harsh reaction conditions such as a reaction at −78° C.; moreover, the selectivity in the protection and deprotection for a plurality of intermediate phenol hydroxyl groups and primary hydroxyl groups is poor, resulting in difficulty in purification, and the multiple protections and deprotections result in cumbersome operation steps.

Cuevas et al. reported a method for preparing ecteinascidin analogs (J. Org. Chem, Vol. 68, No. 23, 2003, 8859-8866), which involves intermediate preparation methods involving first protecting a primary hydroxyl group with TBDPS, followed by phenol hydroxyl group oxidation, selective hydroxylation, then TBDPS protecting group removal from the primary hydroxyl group, and then esterification of the primary hydroxyl group with a cysteic acid derivative. The deprotection of the phenol hydroxyl group and the primary hydroxyl group in this method lacks selectivity, for example, during the removal of the TBDPS from compound 32/33 to prepare compound 34, MEM on the phenol hydroxyl group is easily removed from protection at the same time, and the by-product is difficult to remove and affects the yield and purity of subsequent reactions, thereby ultimately affecting the purification and quality control of API; furthermore, as shown below, 7 steps of reaction are required for only the preparation of compound 34 from compound 25, causing the reaction route to be cumbersome; in addition, during the preparation of compound 28 from compound 25, the protection of the primary hydroxyl group and phenol hydroxyl group with TBDPS also presents a poor selectivity as what is mentioned above, and during the protection of the primary hydroxyl group, the phenol hydroxyl group is also protected at the same time; furthermore, the subsequent purification process has difficulty in removing by-products.

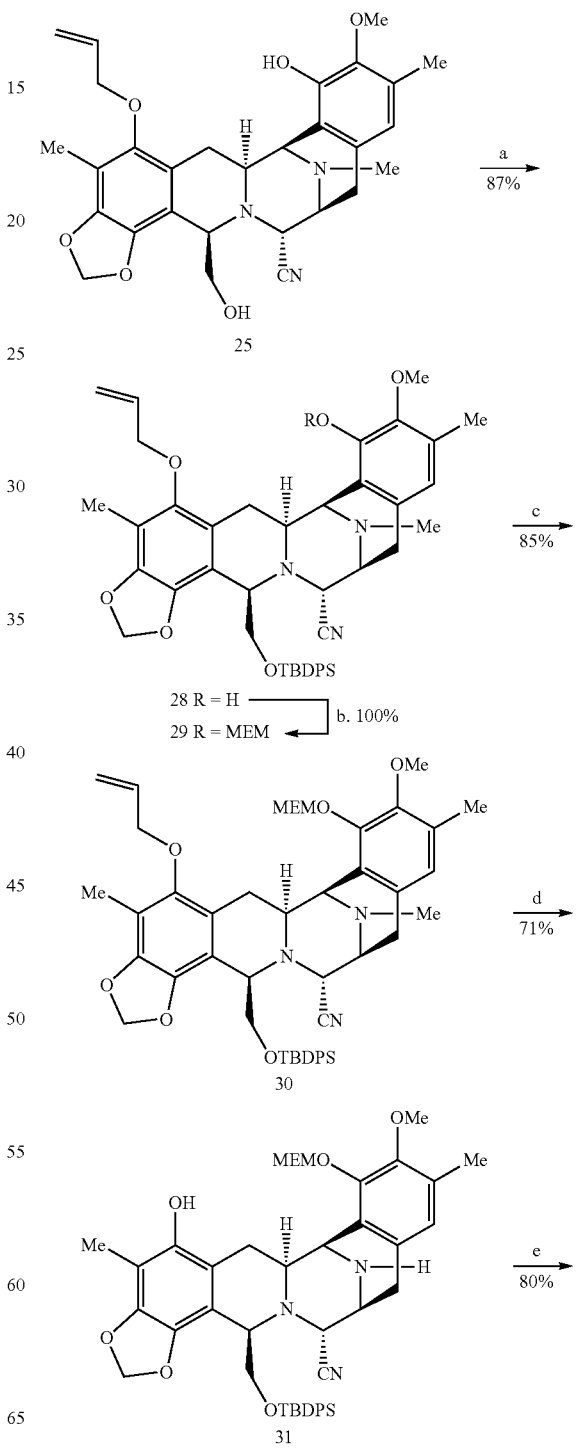

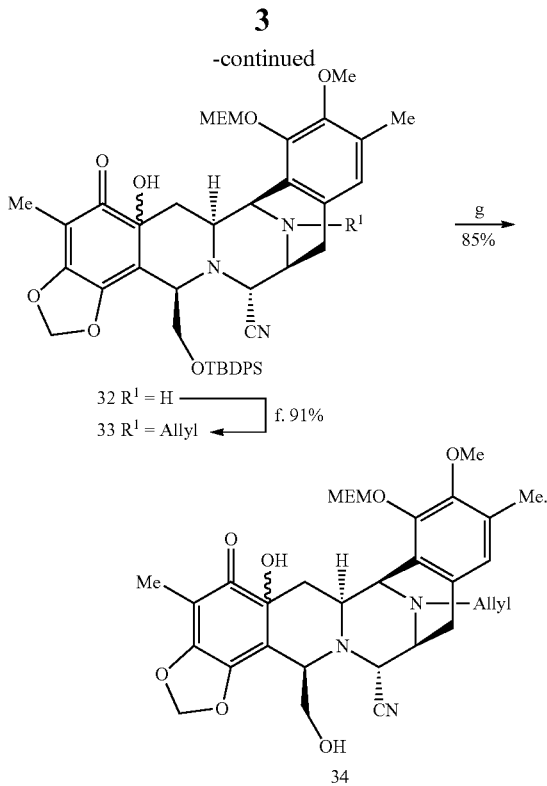

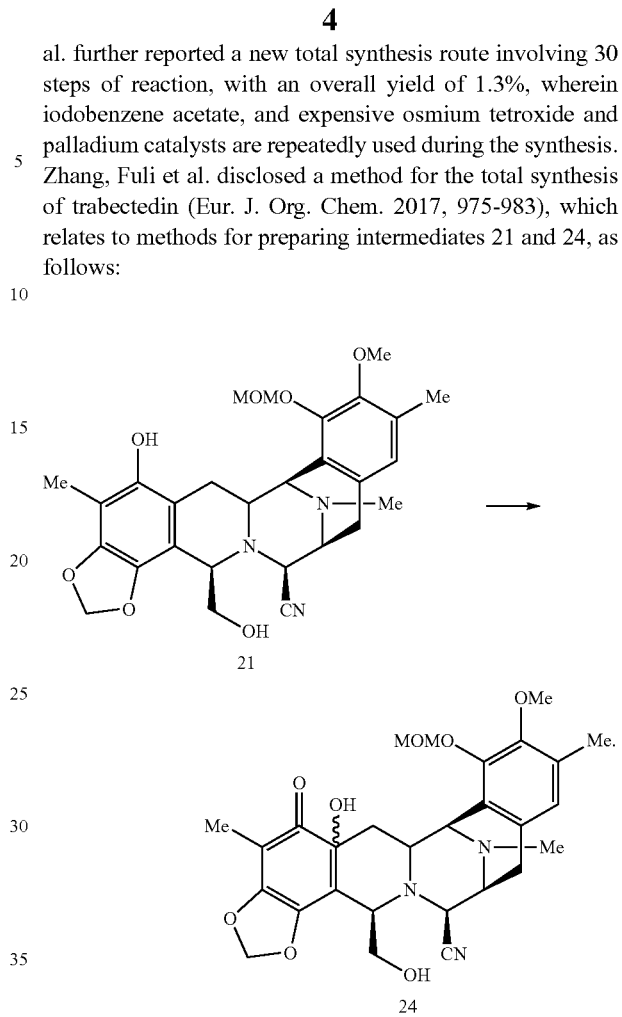

Manzanares et al. reported another method for preparing trabectedin (Org. Lett., Vol. 2, No. 16, 2000, 2545-2548), which comprises first subjecting compound 7 to three steps of reaction to obtain compound 8 in which a phenol hydroxyl group is protected by MOM, and then subjecting the compound 8 to a one-step reaction to obtain compound 9 with an overall yield of 35.8%; this method has a long preparation route, complicated operations and a very low overall yield, and is not suitable for industrial use.

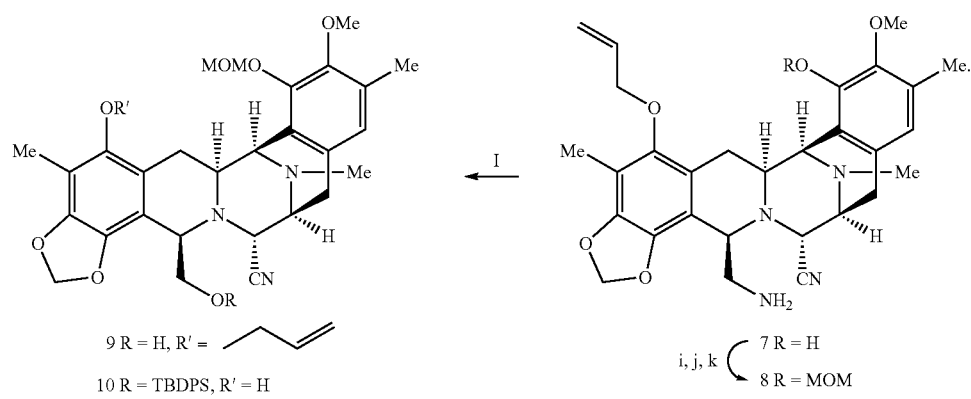

Fukuyama et al reported a total synthesis involving 50 steps, with a yield of 0.56%, in which the use of an expensive chiral ligand and a noble metal ruthenium are also required; in addition, n-butyl lithium, which is a flammable hazardous agent, is used many times (J. Am. Chem. Soc. 2002, 124, 6552-6554); in addition, Zhu et al. reported a total synthesis route involving 31 steps of reaction, with a yield of 1.7%, in which the use of highly toxic hydrofluoric acid and hazardous n-butyl lithium is required. Fukuyama et al. further reported a new total synthesis route involving 30 steps of reaction, with an overall yield of 1.3%, wherein iodobenzene acetate, and expensive osmium tetroxide and palladium catalysts are repeatedly used during the synthesis. Zhang, Fuli et al. disclosed a method for the total synthesis of trabectedin (Eur. J. Org. Chem. 2017, 975-983), which relates to methods for preparing intermediates 21 and 24, as follows:

wherein in this route, the main problem in the direct preparation of compound 24 from compound 21 is that there are a large number of phenol hydroxyl groups also protected during the process of protecting the primary hydroxyl groups of the compound 21, resulting in more side reactions.

In addition, the prior art discloses a semi-synthesis method for trabectedin, the method comprising the following process:

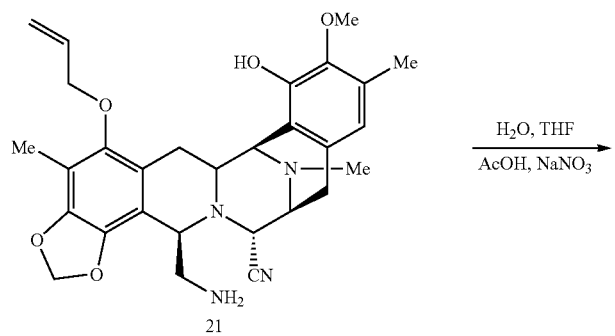
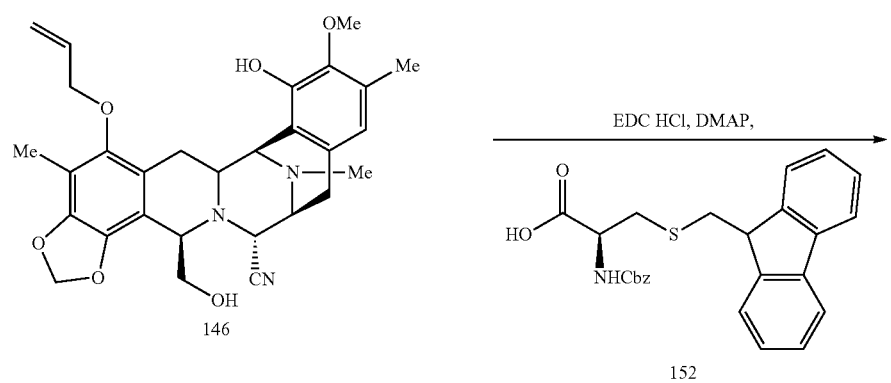
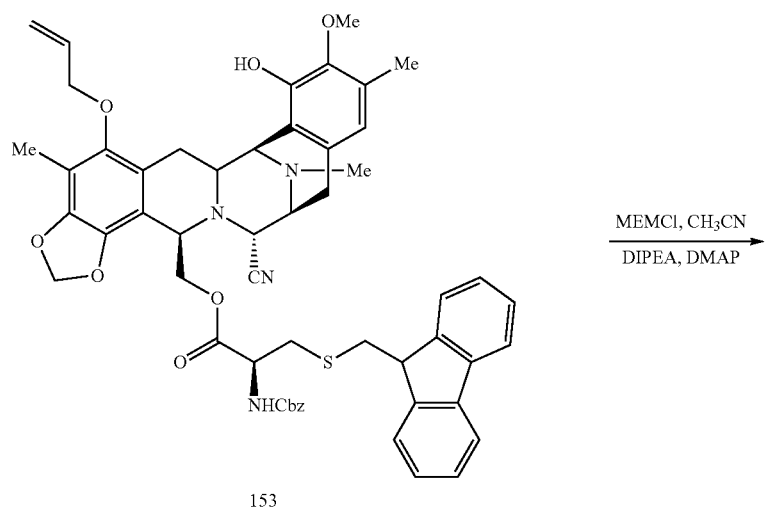

-continued

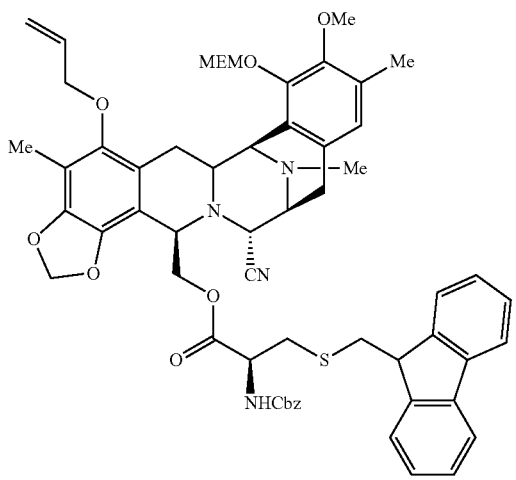

154

This method also has the problem of a poor reaction selectivity; during the esterification of the primary hydroxyl group of compound 146 with a cysteine derivative, the phenol hydroxyl group in the structure also easily undergoes an esterification reaction. Furthermore, compound 153 and compound 154 are both present as an oil, and are difficult to purify and store.

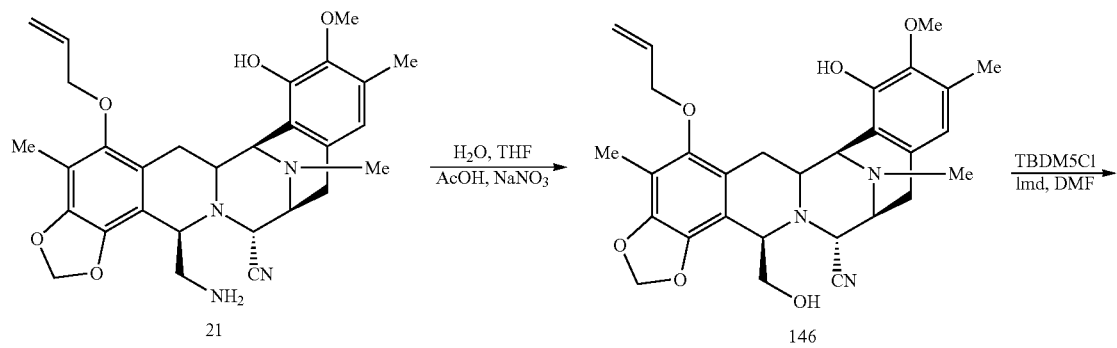

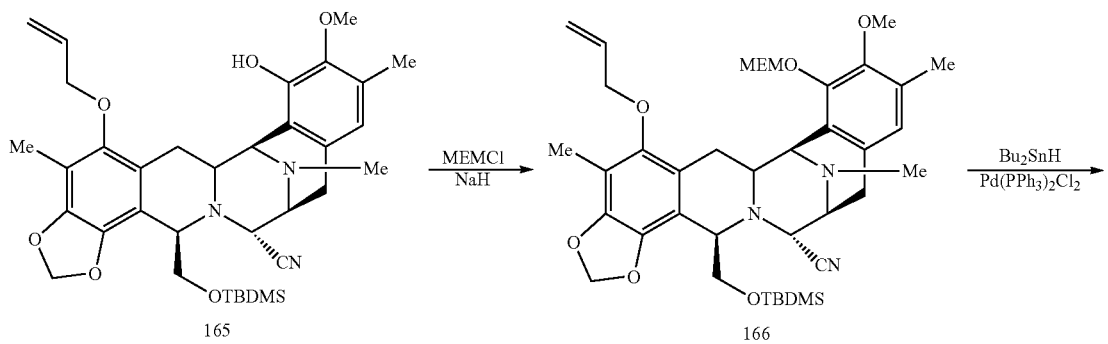

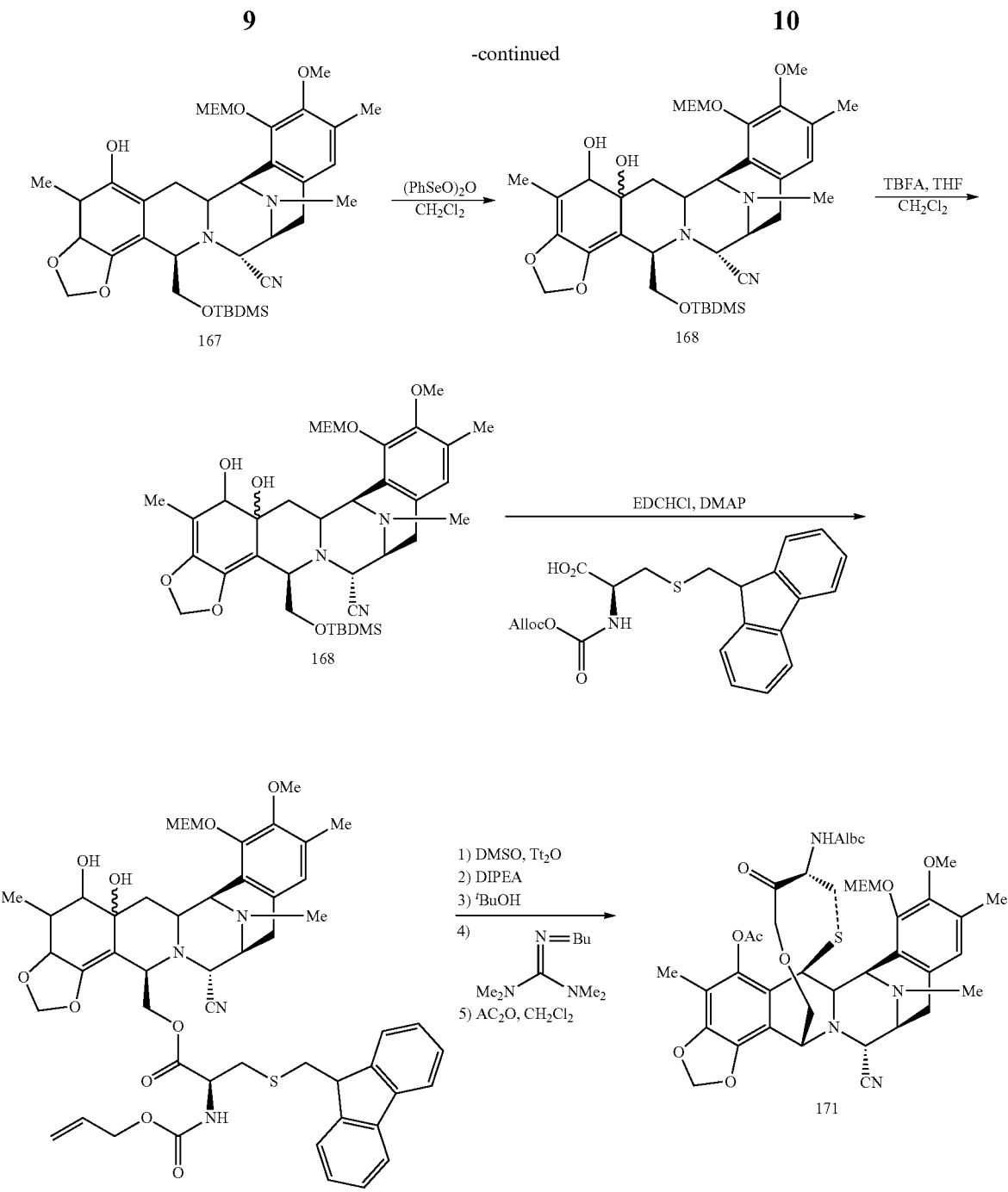

CN 100475822 C discloses a method for preparing compound 170, in which a primary hydroxyl group needs to be protected first by TBOMS due to poor selectivity for the protection of a phenol hydroxyl group with MEM, and the protecting group TBMOS further needs to be subsequently removed from the primary hydroxyl group, resulting in cumbersome reaction steps; in addition, during the deprotection of the primary hydroxyl group, the deprotection of the phenol hydroxyl group easily occurs, resulting in defects such as more side reactions and a low reaction yield.

From the above, it can be seen that there are still many problems to be solved in the methods for preparing trabectedin, such as a long preparation route, a low selectivity for protection and deprotection of the phenol hydroxyl group during a reaction, difficulty in purification, or a need to use highly toxic, expensive reagents, etc., during the reaction process.

3. SUMMARY OF THE INVENTION

The present disclosure describes methods for preparing an ecteinascidin compound and intermediates thereof.

In one embodiment, the present disclosure is directed to a method for preparing compound QT9, comprising reacting compound QT10 with a hydroxyl protecting agent to obtain compound QT9:

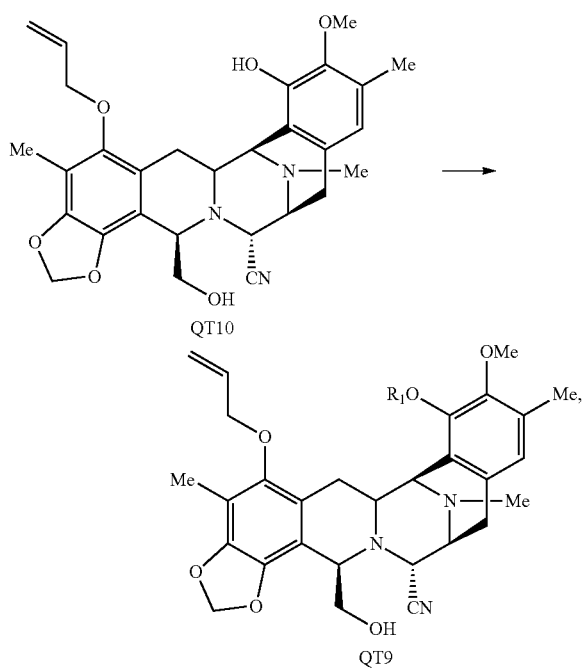

QT10

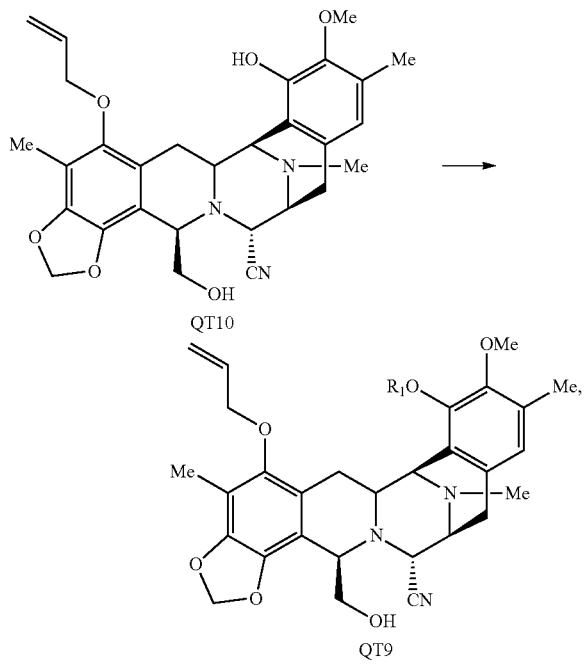

QT9 in which R₁ is a hydroxyl protecting group.

In certain instances, the hydroxyl protecting group R₁ is MOM, MEM, trimethylsilyl, tert-butyldimethylsilyl, or tert-butyldiphenylsilyl.

In one embodiment, the present disclosure is directed to a method for preparing an ecteinascidin compound, comprising reacting compound QT10 with a hydroxyl protecting agent to obtain compound QT9:

QT10

QT9 in which R₁ is a hydroxyl protecting group; preferably, the hydroxyl protecting group R₁ is MOM, MEM, trimethylsi-lyl, tert-butyldimethylsilyl, or tert-butyldiphenylsilyl; and more preferably, the hydroxyl protecting group R₁ is MOM or MEM.

In some instances, the method further comprises selectively removing the allyl group from the compound QT9 to obtain compound QT8:

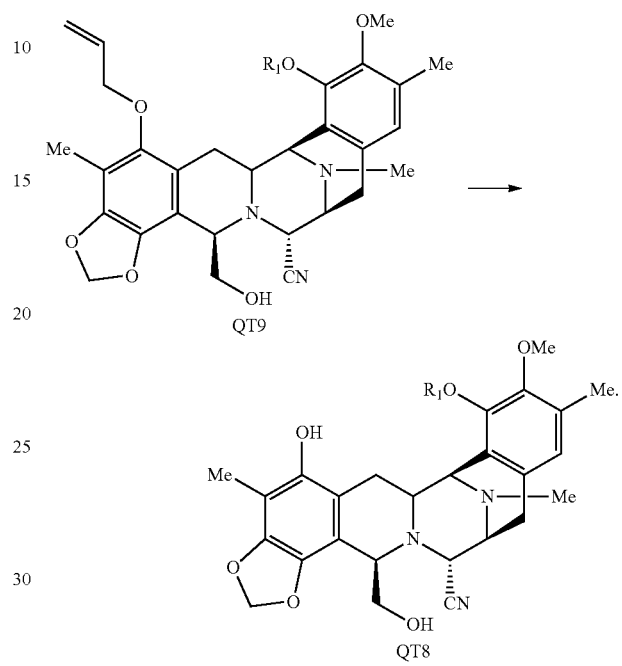

QT9

QT8

In some aspects, the method further comprises subjecting the phenol hydroxyl group of the compound QT8 to oxidization, and selective hydroxylation for conversion into compound QT7:

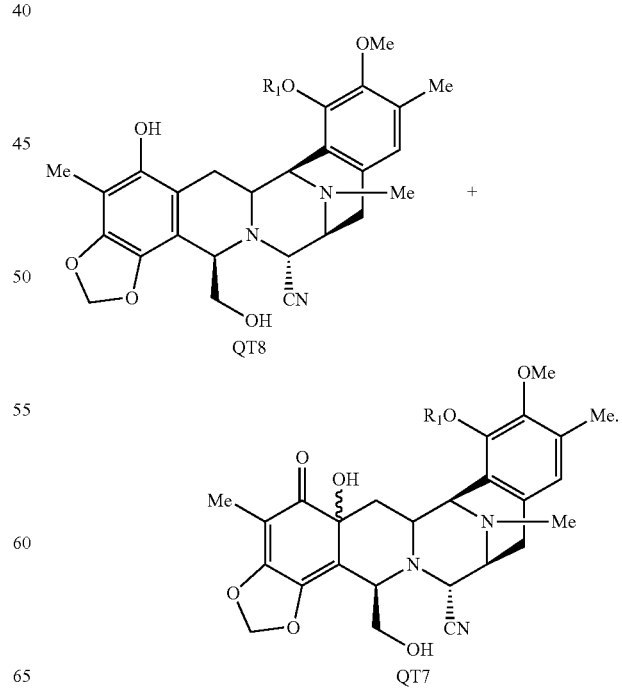

QT8 +

QT7

In some aspects, the method further comprises esterifying the primary hydroxyl group of the compound QT7 with a cysteine derivative for conversion into compound QT6:

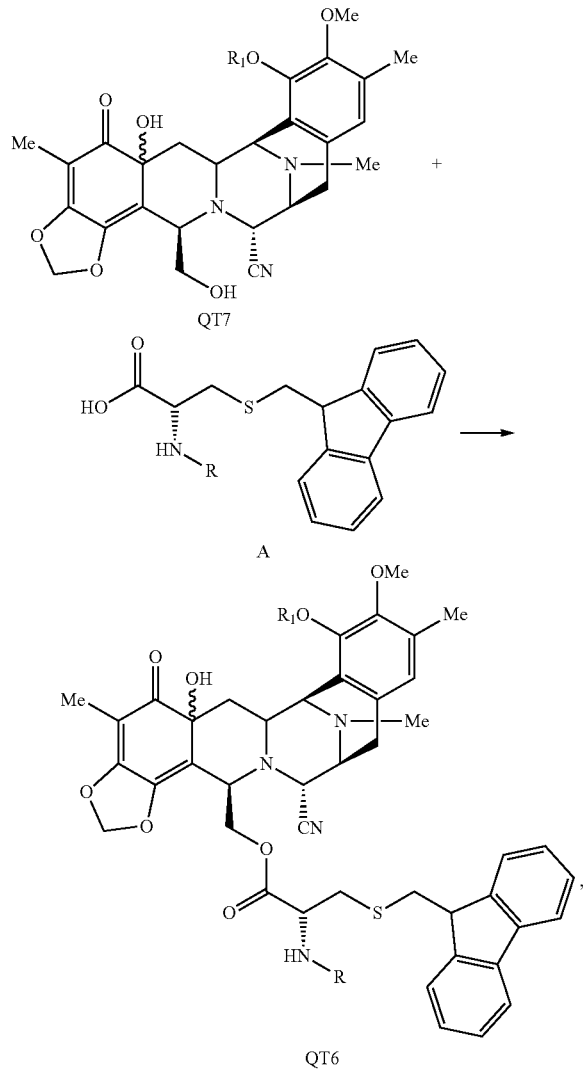

in which R is an amino protecting group, and preferably, R is Alloc, Cbz, Troc, or Boc.

In some aspects, the method further comprises esterifying the primary hydroxyl group of the compound QT9 with a cysteine derivative for conversion into compound QT8A:

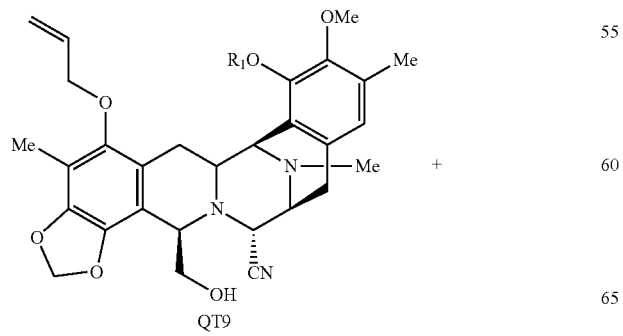

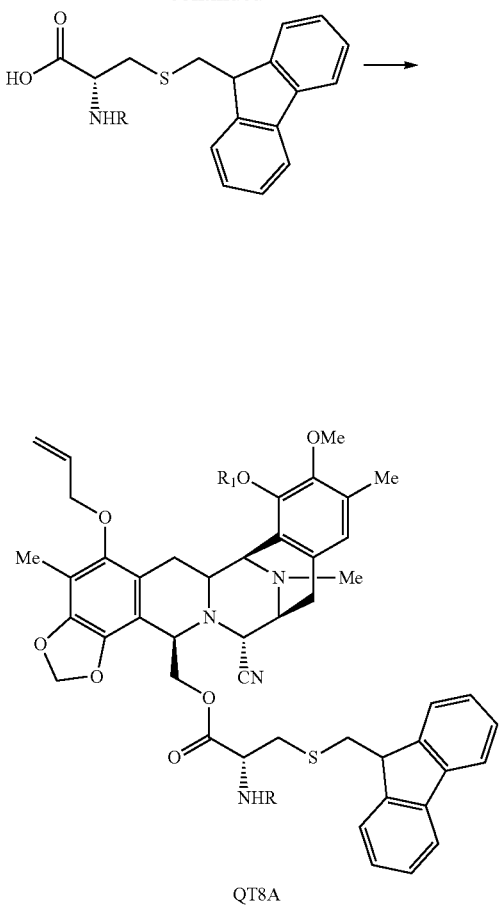

in which R is an amino protecting group, and preferably, R is Alloc, Cbz, Troc, or Boc.

In some aspects, the method further comprises selectively removing the allyl group from the compound QT8A to obtain compound QT7A:

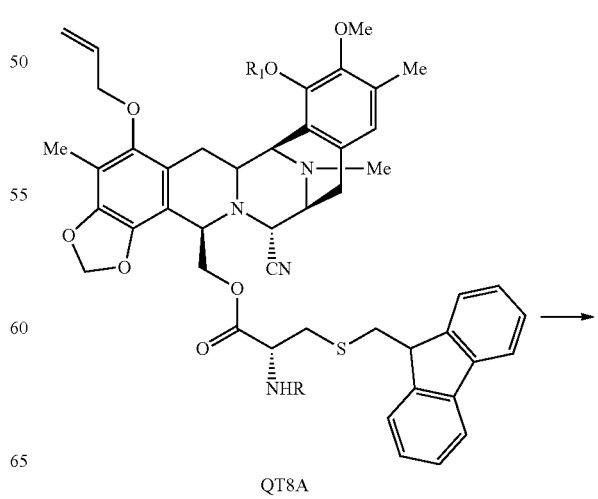

-continued

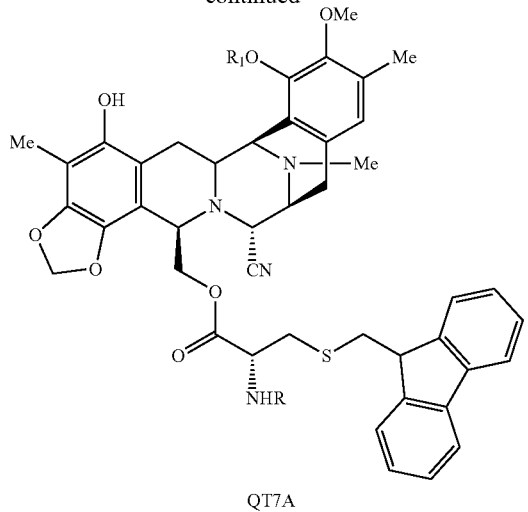

QT7A

In some aspects, the method further comprises subjecting the phenol hydroxyl group of the compound QT7A to oxidization, and selective hydroxylation for conversion into compound QT6:

QT7A

QT6

In some aspects, the method further comprises reacting the compound QT6 with a Swern reagent and further with N-tert-butyl-N',N'-tetramethylguanidine to form a 1,4-bridged lactone compound QT5:

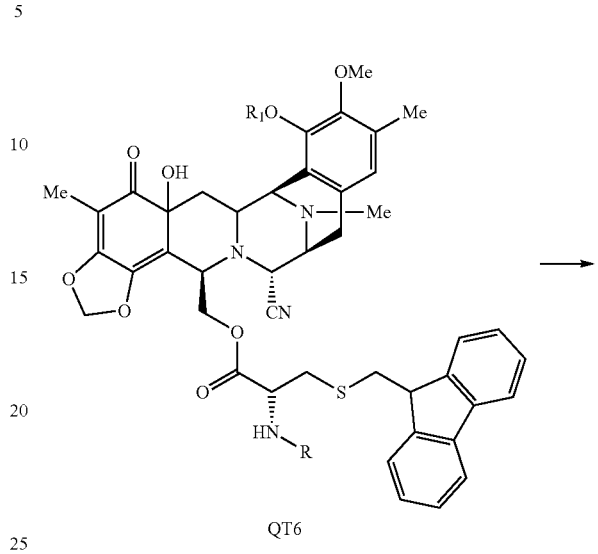

QT6

In some aspects, the method further comprises selectively removing amino protecting group R from the compound QT5 to obtain compound QT4:

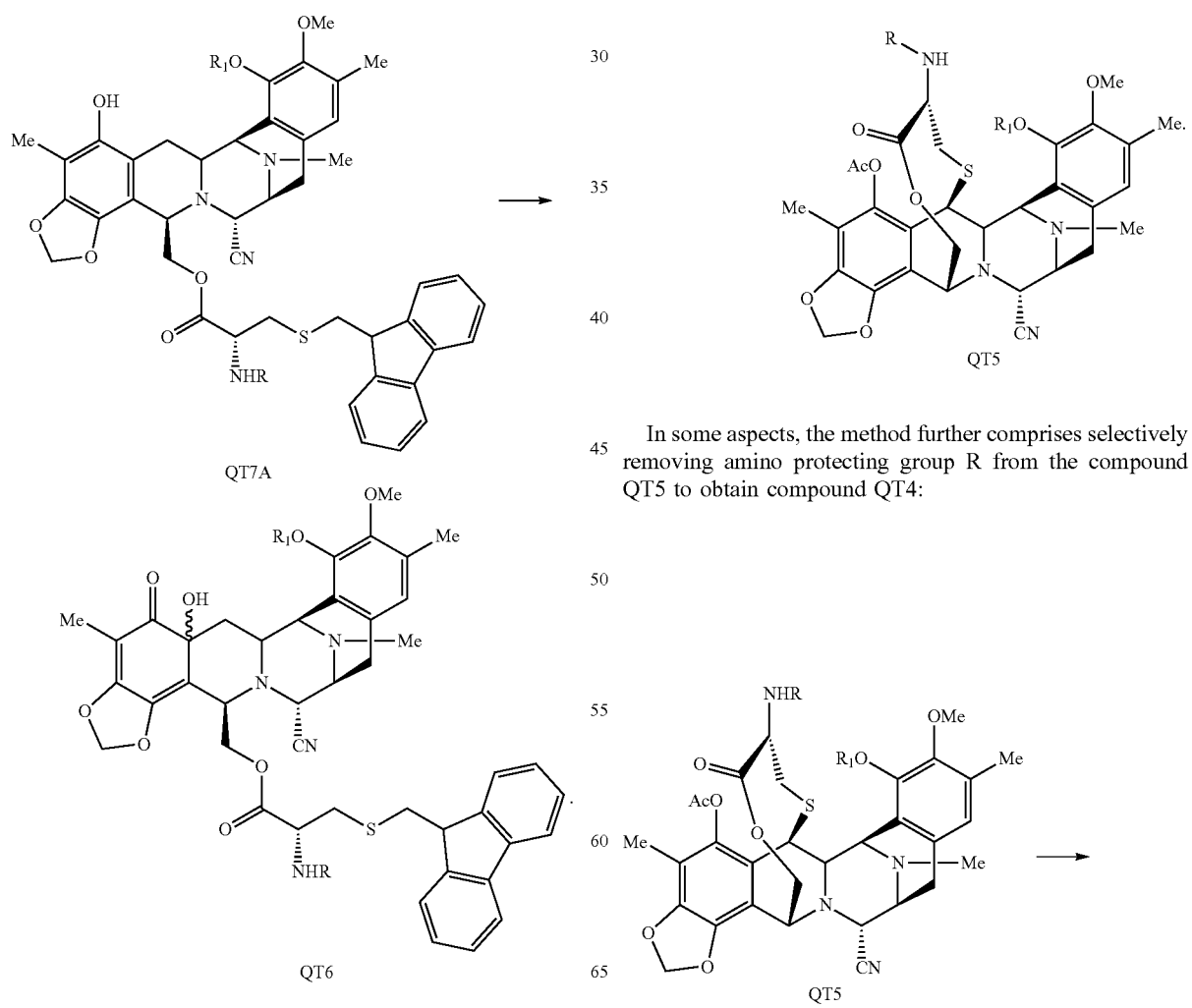

QT5

QT5

-continued

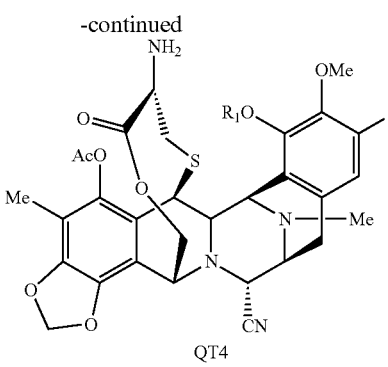
QT4

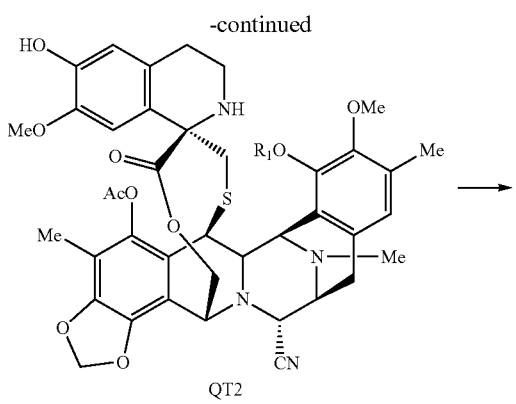
QT2

In some aspects, the method further comprises converting the compound QT4 into compound QT3 by means of a transamination reaction:

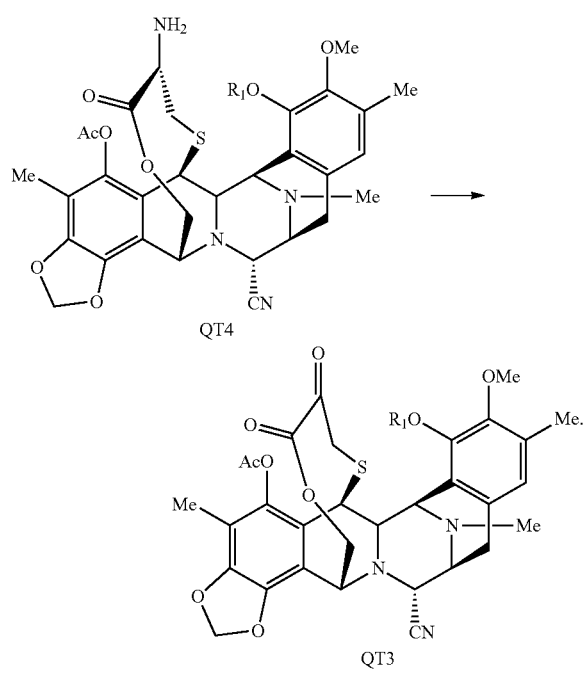

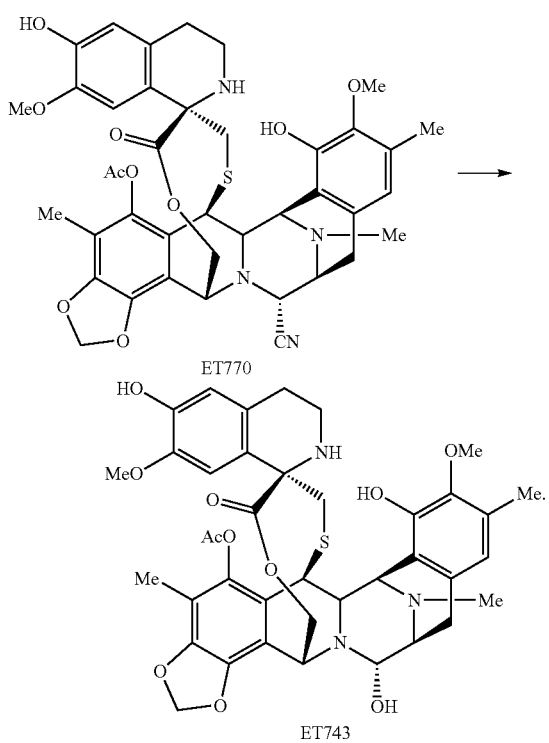
ET770

ET743

In some aspects, the method further comprises reacting the compound QT3 with 2-[3-hydroxy-4-methoxy-phenyl]ethylamine for conversion into compound QT2, then selectively removing the phenol hydroxyl protecting group RI from the compound QT2 to obtain compound ET770, and optionally converting CN in the compound ET770 into OH to obtain compound ET743:

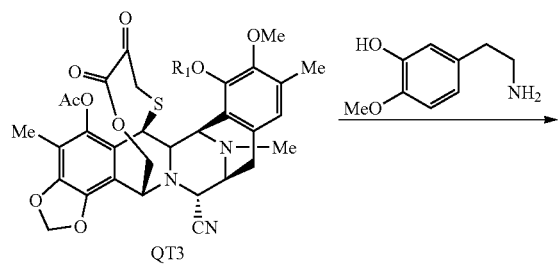

In some aspects, the method further comprises simultaneously removing the amino protecting group R and the hydroxyl protecting group RI from the compound QT5 to obtain compound QT4A:

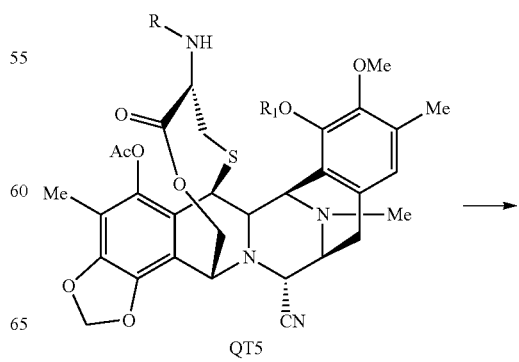
QT5

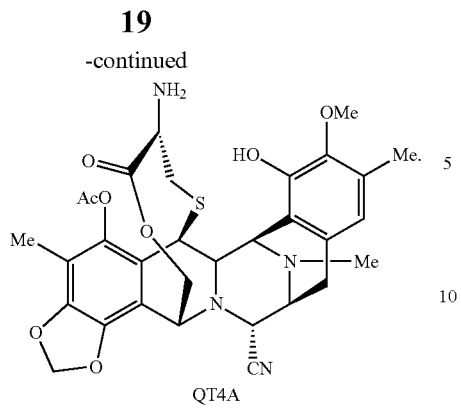

QT4A

In some aspects, the method further comprises converting the compound QT4A into compound QT3A by means a transamination reaction, and optionally comprises reacting the compound QT3A with 2-[3-hydroxy-4-methoxy-phenyl] ethylamine for conversion into compound ET770, and further converting CN in the compound ET770 into OH to obtain compound ET743:

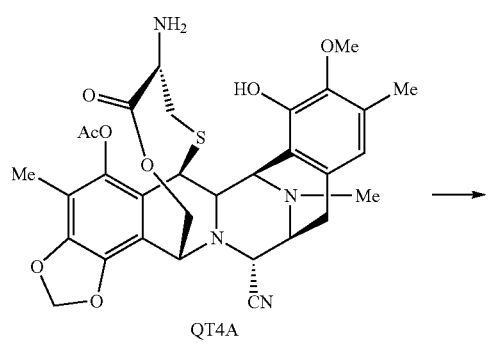

QT4A

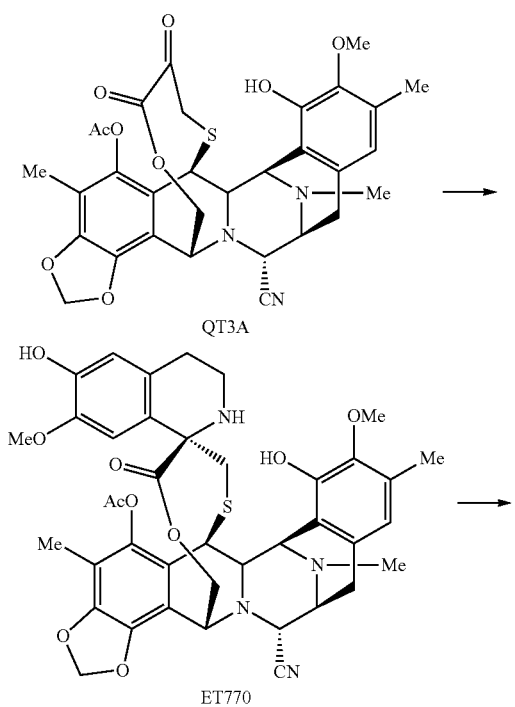

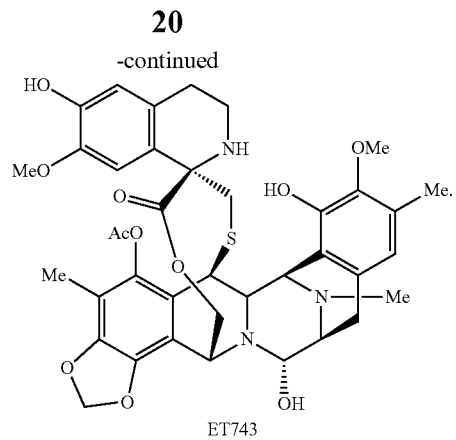

ET743

In some instances, the compound QT10 is converted into compound QT9 under alkaline conditions, in which the base is NaOH, KOH, NaH, LiOH, LiOCH$_3$, Na$_2$CO$_3$, K$_2$CO$_3$ or a mixture thereof, and the base is preferably NaOH, KOH, NaH or a mixture thereof.

In other instances, the hydroxyl protecting agent is bromomethyl methyl ether, chloromethyl methyl ether, or 2-methoxyethoxymethyl chloride, and the molar ratio of the compound QT10 to the hydroxyl protecting agent is 1:1 to 20, preferably 1.5 to 2.5.

In some aspects, the molar ratio of the compound QT10 to the base is 1:1 to 30, preferably 1.5 to 4, and the reaction temperature is −10° C. to 30° C., preferably 0° C. to 10° C.

In some aspects, R$_1$ is MEM or MOM; and R is Alloc, Cbz, or Troc. In other aspects, R$_1$ is MEM or MOM, and R is Boc.

In one embodiment, the present disclosure describes a compound, the compound has the following structure:

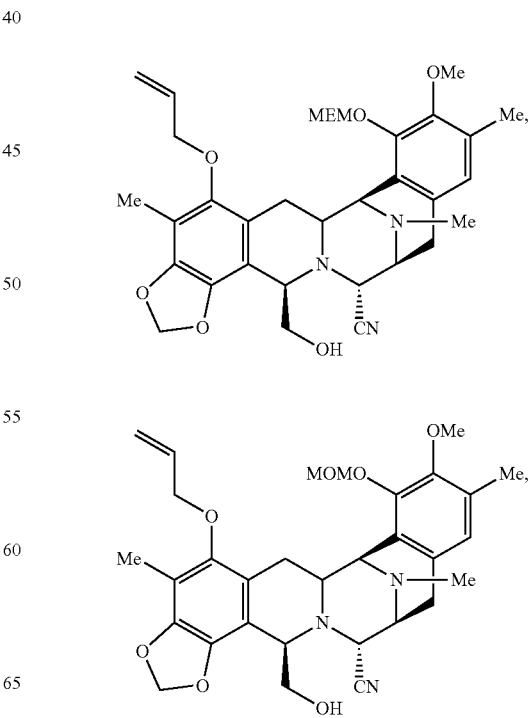

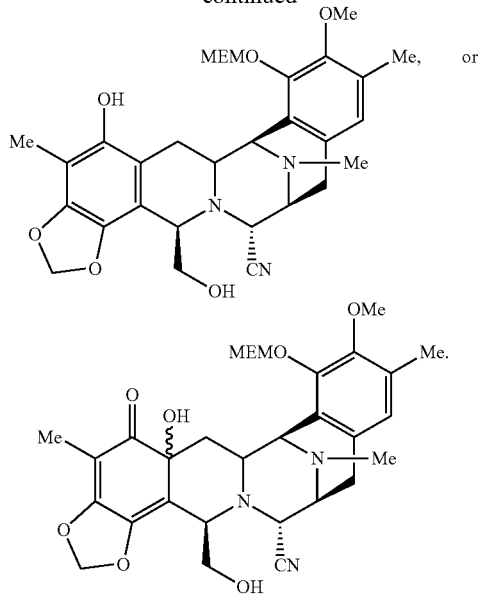

4. DETAILED DESCRIPTION OF THE EMBODIMENTS

4.1. Definitions

Terms and abbreviations used in the present invention: "MOM" refers to methoxy methyl ether; "MEM" refers to methoxyethoxymethyl; Boc refers to tert-butoxycarbonyl; Alloc refers to allyloxycarbonyl: Cbz refers to benzyloxycarbonyl; Troc refers to 2,2,2-trichloroethoxycarbonyl; EDCl refers to 1-ethyl-(3-dimethylaminopropyl)carbodiimide hydrochloride (EDCHCl); DMAP refers to 4-dimethylaminopyridine; DBU refers to 1,8-diazabicycloundec-7-ene; and DIPEA refers to diisopropylethylamine.

4.2. Detailed Description

In order to solve the above-mentioned problems, the present invention provides a new method for preparing trabectedin and an intermediate.

Firstly, the present invention provides a method for preparing intermediate compound QT9 of trabectedin, the method comprising reacting compound QT10 with a hydroxyl protecting agent to obtain compound QT9:

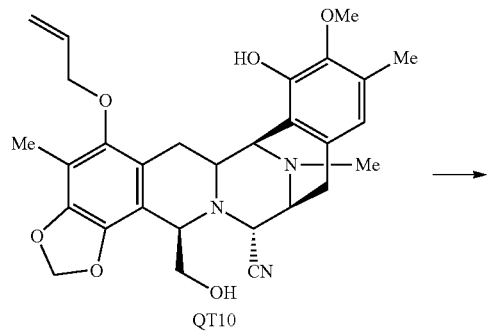

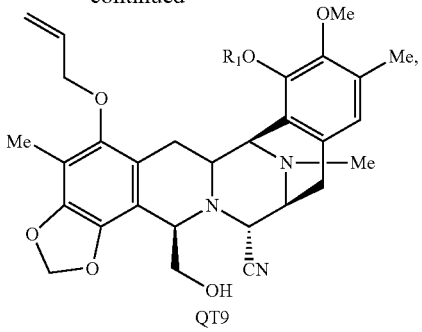

in which $R_1$ is a hydroxyl protecting group, and the hydroxyl protecting group $R_1$ is preferably MOM (methoxymethyl), MEM (methoxyethoxymethyl), trimethylsilyl, tert-butyldimethylsilyl, or tert-butyldiphenylsilyl; further preferably, the hydroxyl protecting group $R_1$ is MOM or MEM.

Preferably, in the above-mentioned reaction, the compound QT10 is reacted with the hydroxyl protecting agent in a suitable solution such as tetrahydrofuran, ethylene glycol dimethyl ether or a mixed solution thereof at a suitable temperature such as −10° C. to 20° C. under alkaline conditions to produce the compound QT9, wherein the hydroxyl protecting agent is preferably bromomethyl methyl ether, chloromethyl methyl ether, or 2-methoxyethoxymethyl chloride, more preferably bromomethyl methyl ether or 2-methoxyethoxymethyl chloride. The molar ratio of the compound QT10 to the hydroxyl protecting agent therein is 1:1 to 20, preferably 1:1 to 10, more preferably 1:1.5 to 2.5, and the base is NaOH, KOH, NaH, potassium t-butoxide, lithium t-butoxide, LiOH, LiOCH$_3$ or a combination thereof; preferably NaOH, KOH, NaH, or a mixture thereof, most preferably NaOH. The molar ratio of the compound QT10 to the base is 1:0.5 to 30, preferably 1:1 to 15, more preferably 1:1.5 to 4, most preferably 1:1 to 2.5; and the reaction temperature is −10° C. to 30° C., preferably 0° C. to 20° C., more preferably 0° C. to 10° C.

The inventors have found through extensive experimental design and verification studies that during the reaction of the compound QT10 with the hydroxyl protecting agent, where the base is NaOH, KOH, NaH, potassium t-butoxide, lithium t-butoxide, LiOH, LiOCH$_3$ or a combination thereof, conversion of the compound QT10 to the compound QT9 can be achieved; furthermore, where the base is selected from NaOH or NaH, the reaction effect is particularly good, and the conversion efficiency is significantly improved, for example, it can be as high as 98%; moreover, where the base is NaOH or NaH, and the hydroxyl protecting agent is bromomethyl methyl ether or 2-methoxyethoxymethyl chloride, the reaction process can results in the selective protection of the phenol hydroxyl group with MOM or MEM, while side reactions on the primary hydroxyl position are very few, for example, it can be less than 2%; in addition, since the conversion rate of the reaction in this step is high and the purity of the resulting product is very high, no complicated chromatographic purification or column chromatography is necessary, and refining can be achieved simply by recrystallization; in addition, studies have found that the compound QT9 has a very good performance and can be purified by means of crystallization in various solvents such as ethyl acetate, isopropanol and methanol, so that it is very suitable for industrial applications; in addition, since NaOH is significantly safer than NaH in the industrial scale-up production process, it is more preferable that the base is NaOH in the industrial process.

In another aspect, the present invention further provides a method for preparing an ecteinascidin compound, the method comprising: selectively protecting the phenol hydroxyl group of compound QT10 to obtain compound QT9:

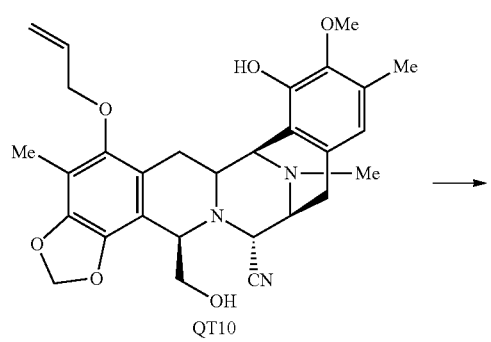
QT10

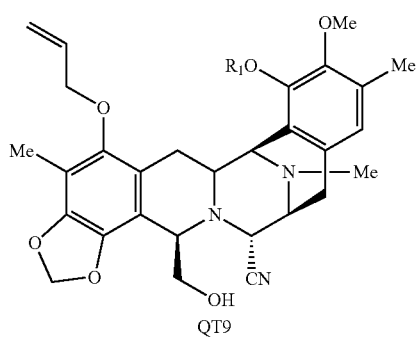
QT9 in which $R_1$ is a hydroxyl protecting group; preferably, the hydroxyl protecting group $R_1$ is MOM, MEM, trimethylsilyl, tert-butyldimethylsilyl, or tert-butyldiphenylsilyl; and more preferably, the hydroxyl protecting group $R_1$ is MOM or MEM.

The above-mentioned method for preparing the ecteinascidin compound further comprises selectively removing the allyl group from the compound QT9 to obtain compound QT8:

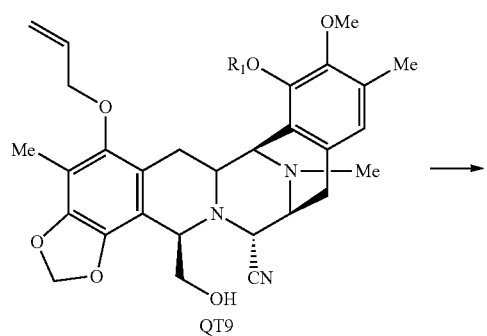
QT9

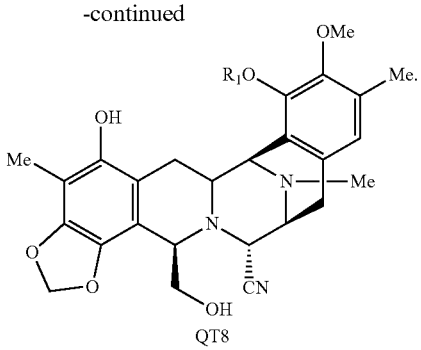
QT8

In a preferred embodiment, the reaction temperature for the conversion of the compound QT9 into the compound QT8 is preferably −10° C. to 30° C., more preferably −5° C. to 10° C., and the reaction time for this conversion is preferably 0.5 to 4 hours, more preferably 1 to 2 hours.

Furthermore, the method for preparing the ecteinascidin compound further comprises subjecting the phenol hydroxyl group of the compound QT8 to oxidization, and selective hydroxylation for conversion into compound QT7:

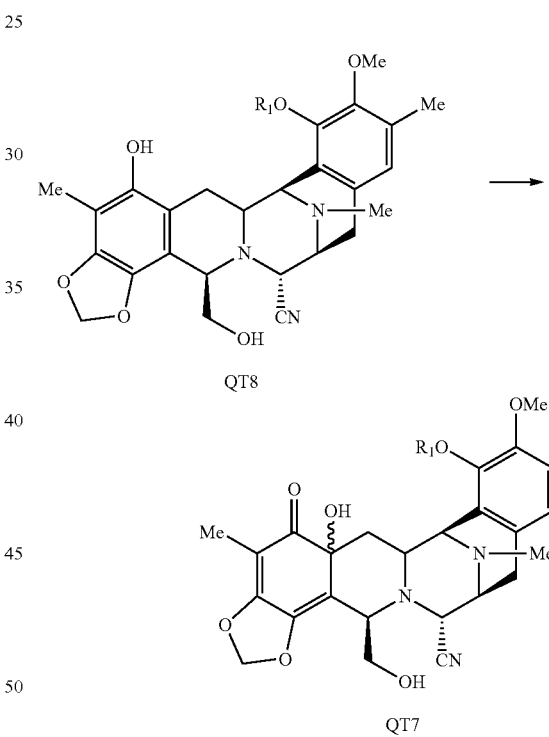
QT8

QT7 wherein an oxidizing agent for the oxidation reaction is preferably benzeneseleninic anhydride or 2-iodoxybenzoic acid, more preferably benzeneseleninic anhydride; the molar ratio of the compound QT8 to the oxidizing agent is preferably 0.5 to 2.0 eq, more preferably 0.6 to 0.8 eq; the reaction temperature is preferably −40° C. to 30° C., more preferably −20° C. to −10° C.; the reaction time is preferably 0.5 to 4 hours, more preferably, 1.5 to 2 hours; and the reaction solvent is preferably dichloromethane, ethyl acetate, tetrahydrofuran or isopropanol.

Furthermore, the method for preparing the ecteinascidin compound further comprises esterifying the primary hydroxyl group of the compound QT7 with a cysteine derivative for conversion into compound QT6:

25

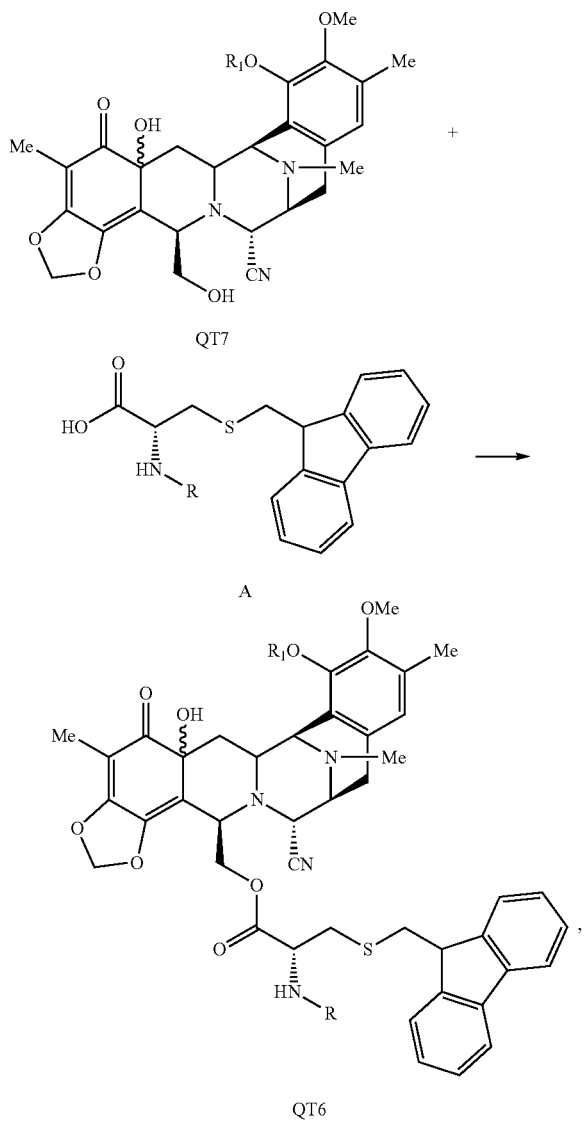

QT7

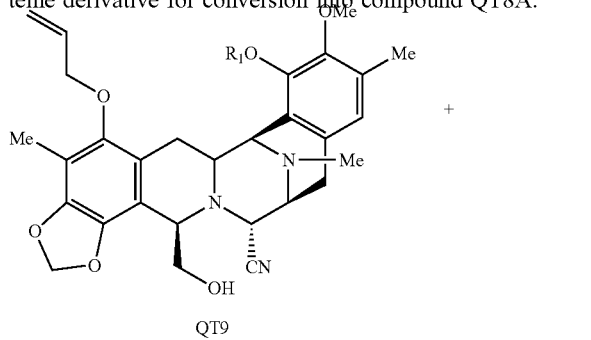

QT9 wherein R is an amino protecting group, and preferably, R is Alloc (allyloxycarbonyl), Cbz (benzyloxycarbonyl), Troc (2,2,2-trichloroethoxycarbonyl), or Boc (benzyloxycarbonyl).

In another embodiment of the present invention, a method for preparing an ecteinascidin compound is further provided, the method comprising esterifying the primary hydroxyl group of the above-mentioned compound QT9 with a cysteine derivative for conversion into compound QT8A:

26

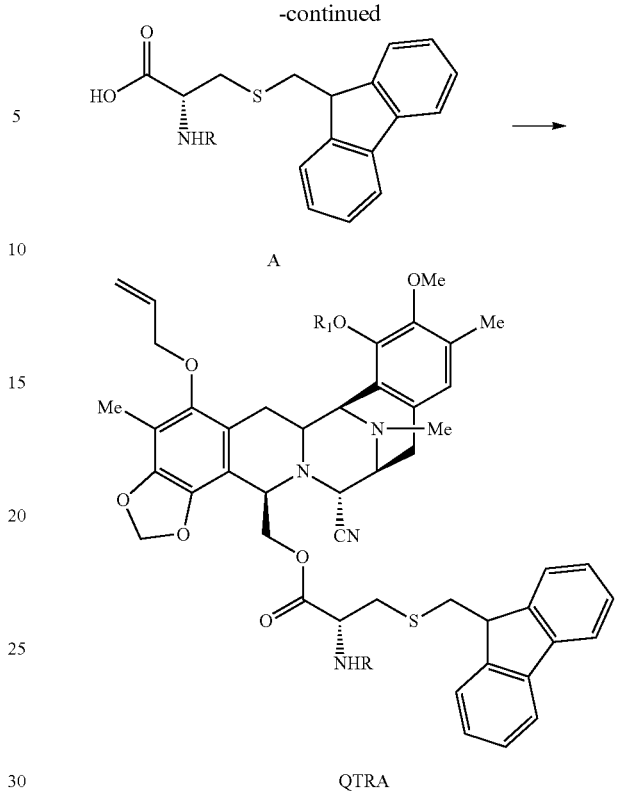

QTRA in which R is an amino protecting group, and preferably, R is Alloc, Cbz, Troc, or Boc.

In the above reaction, the molar ratio of the compound QT9 to the compound A is preferably 1:1 to 2, more preferably 1:1.5; the reaction temperature is preferably −10° C. to 30° C., more preferably 5° C. to 10° C.; the reaction time is preferably 1 to 4 hours, more preferably 1.5 to 2 hours; the amount of EDCl is preferably 1.5 to 3 eq, more preferably 1.5 eq; and the amount of DMAP is preferably 0.3 to 1 eq, more preferably 0.5 eq.

Furthermore, the method further comprises selectively removing the allyl group from the compound QT8A to obtain compound QT7A:

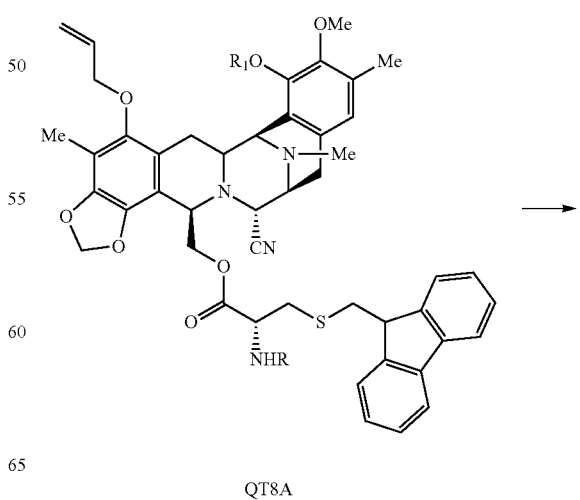

QT8A

27

-continued

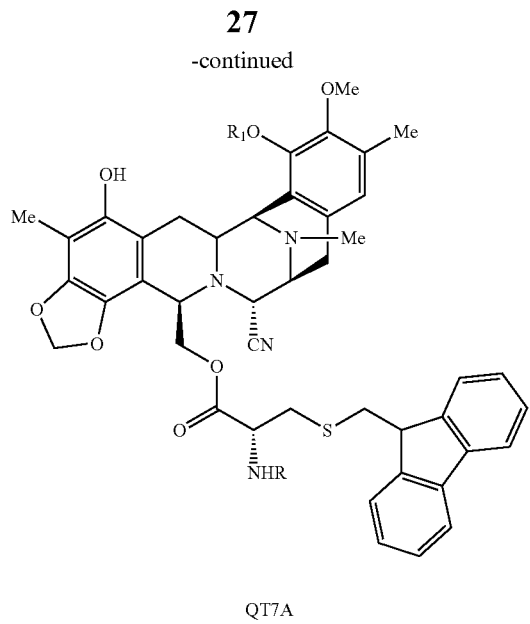

QT7A

28

-continued

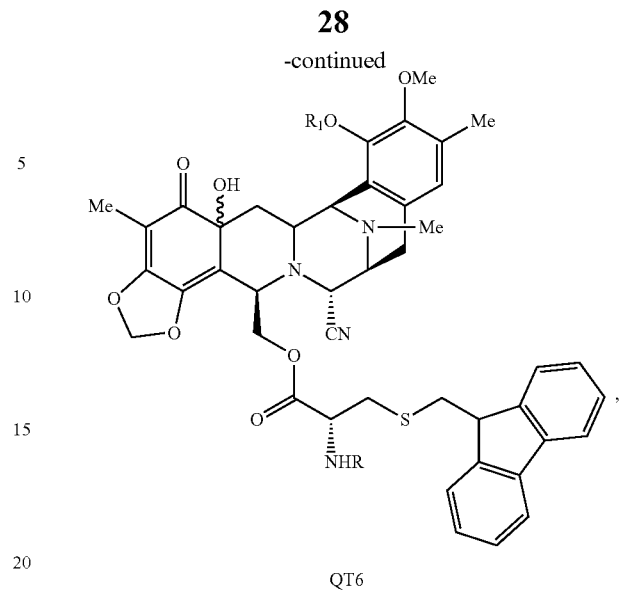

QT6

In a preferred embodiment, in the above-mentioned steps for the conversion of the compound QT8A into the compound QT7A, the reaction temperature is preferably −10° C. to 30° C., more preferably −5° C. to 10° C., and the reaction time is preferably 0.5 to 4 hours, more preferably 1 to 2 hours.

The above-mentioned method for preparing the ecteinascidin compound further comprises subjecting the phenol hydroxyl group of the compound QT7A to oxidization, and selective hydroxylation for conversion into compound QT6:

wherein an oxidizing agent for the oxidation reaction is preferably benzeneseleninic anhydride or 2-iodoxybenzoic acid, more preferably benzeneseleninic anhydride; the molar ratio of the compound QT7A to the oxidizing agent is preferably 0.5 to 2.0 eq, more preferably 0.6 to 0.8 eq, and the reaction temperature is preferably −40° C. to 30° C., more preferably −20° C. to −10° C.; the reaction time is preferably 0.5 to 4 hours, more preferably 1 to 2 hours, and the reaction solvent is preferably dichloromethane, ethyl acetate, tetrahydrofuran or isopropanol.

Furthermore, the above-mentioned method for preparing the ecteinascidin compound further comprises reacting the compound QT6 with a Swern reagent and further with N-tert-butyl-N',N'-tetramethylguanidine to form a 1,4-bridged lactone compound QT5:

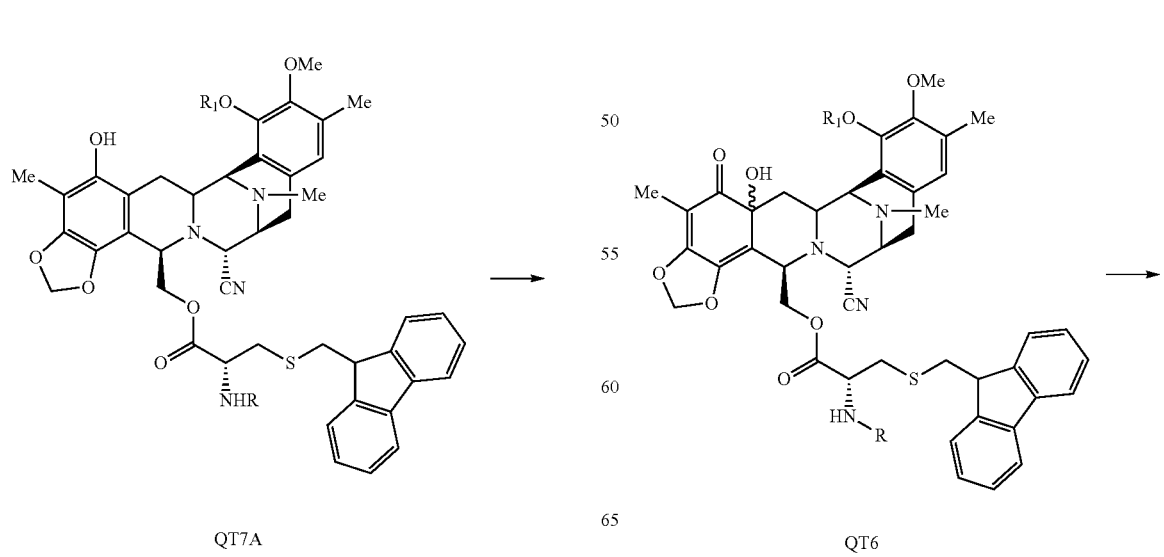

QT7A          QT6

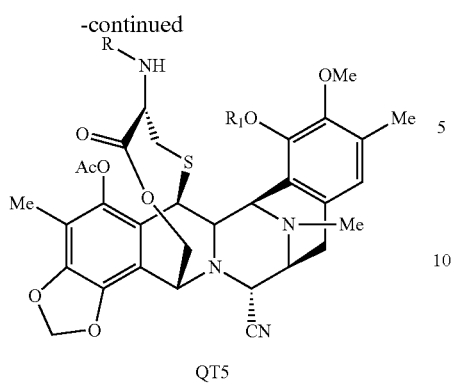

QT5

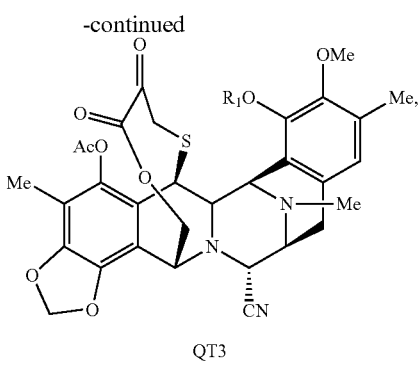

QT3

Furthermore, the above-mentioned method for preparing the ecteinascidin compound further comprises selectively removing amino protecting group R from the compound QT5 to obtain compound QT4:

Furthermore, the above-mentioned method for preparing the ecteinascidin compound further comprises reacting the compound QT3 with 2-[3-hydroxy-4-methoxy-phenyl]ethylamine for conversion into compound QT2, then selectively removing the phenol hydroxyl protecting group RI from the compound QT2 to obtain compound ET770, and optionally converting CN in the compound ET770 into OH to obtain compound ET743:

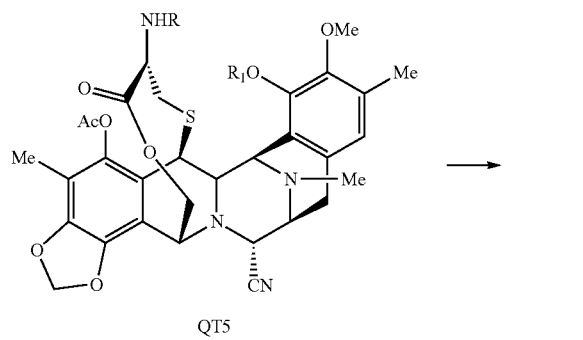

QT5

QT4

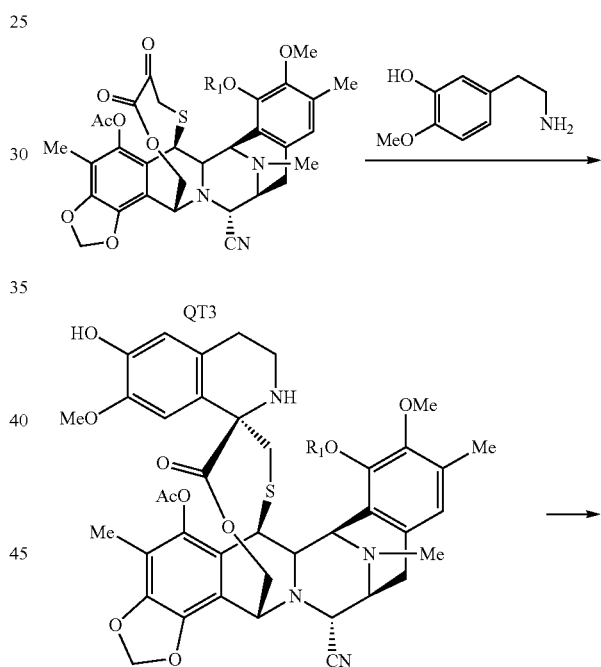

Furthermore, the above-mentioned method for preparing the ecteinascidin compound further comprises converting the compound QT4 into compound QT3 by means of a transamination reaction:

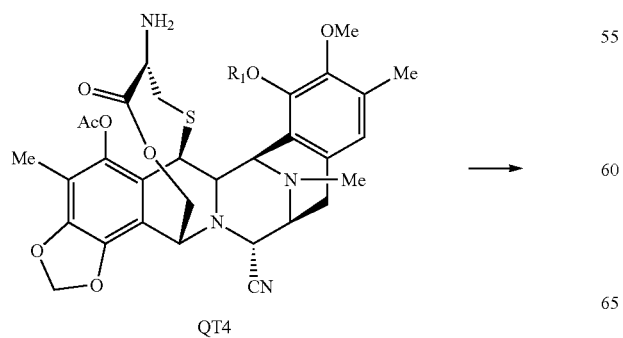

QT4

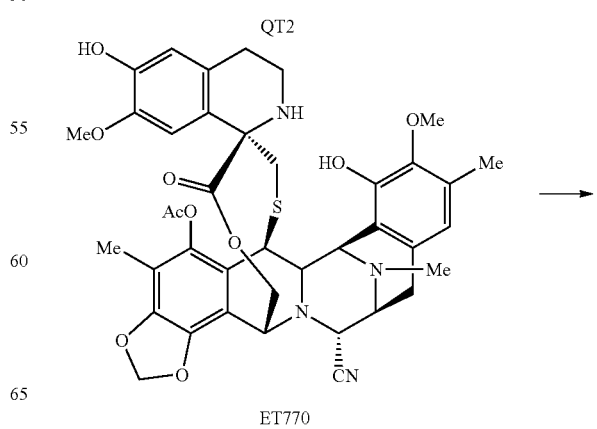

ET770

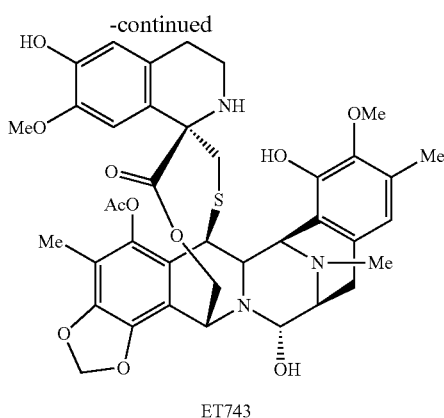

ET743

For the methods for preparing compound QT2 from compound QT3 and for preparing compound ET743 from compound E770, reference can be made to preparation methods disclosed in J. Am. Chem. Soc. 2006, 128, 87-89 or J. Am. Chem. Soc. 1996, 118, 9202-9203.

Furthermore, the above-mentioned method for preparing the ecteinascidin compound further comprises simultaneously removing the amino protecting group R and the hydroxyl protecting group $R_1$ from the compound QT5 to obtain compound QT4A:

the compound QT4A into compound QT3A by means a transamination reaction, and optionally comprises reacting the compound QT3A with 2-[3-hydroxy-4-methoxy-phenyl] ethylamine for conversion into compound ET770, and further converting CN in the compound ET770 into OH to obtain compound ET743:

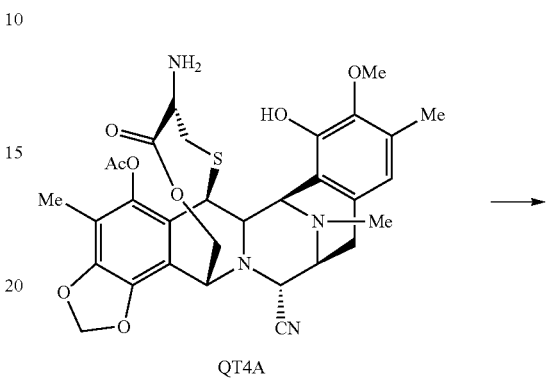

For the method for the reaction in this step, reference can be made to preparation methods disclosed in Eur. J. Org. Chem. 2017, 975-983 and J. Org. Chem, Vol. 68, No. 23, 2003, 8863.

In the above-mentioned method of the present invention, depending on the choice of the specific protecting groups for the phenol hydroxyl group and the cysteine side chain, a plurality of alternative intermediates may be produced, and the total number of synthetic conversions may also vary depending on the selected protecting groups. Generally, where the cysteine side chain protecting group is Boc, the reaction step is correspondingly shorter than where Cbz, Alloc or Troc is used. The reaction schemes and steps are introduced herein for ready understanding by a person skilled in the art.

In particular, in more specific preferred embodiments of the present invention, six methods for preparing ecteinascidin 743 are provided, specifically as shown in routes 1 to 7.

Route 1
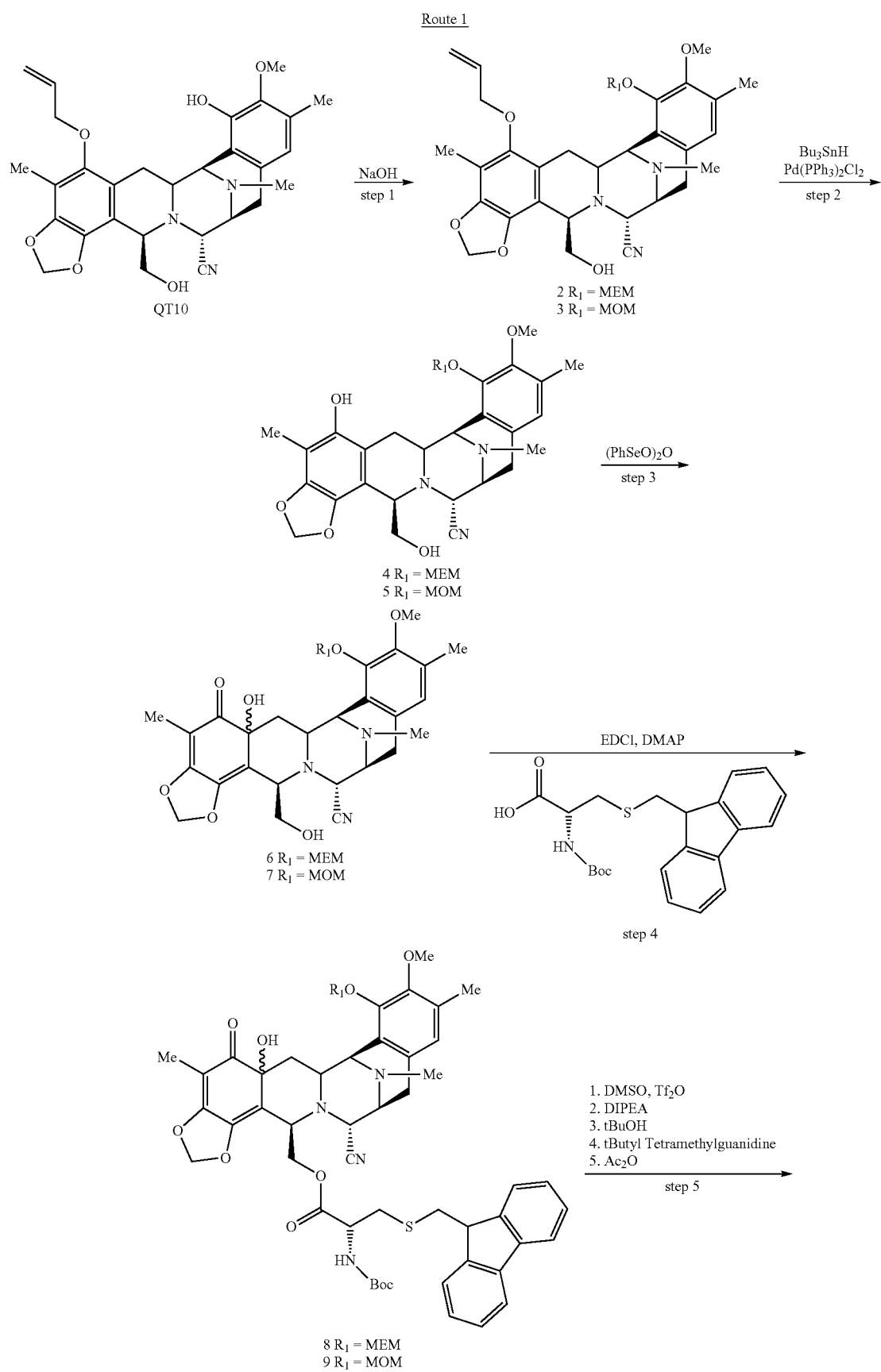

-continued
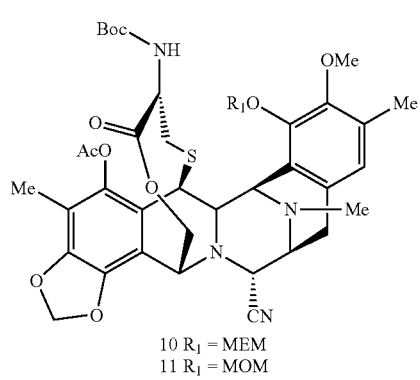
10 R₁ = MEM
11 R₁ = MOM
step 6
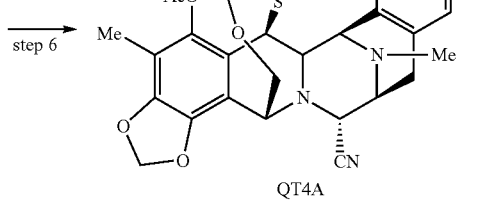
QT4A
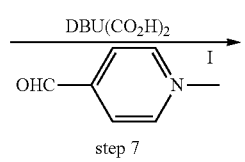
step 7
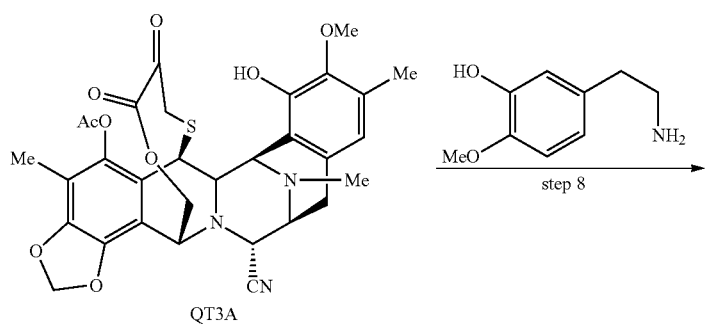
QT3A
step 8
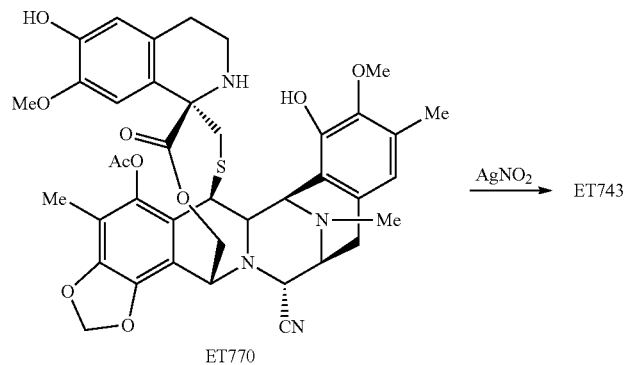
ET770
AgNO₂ → ET743
in which R₁ is MOM or MEM.
Route 2
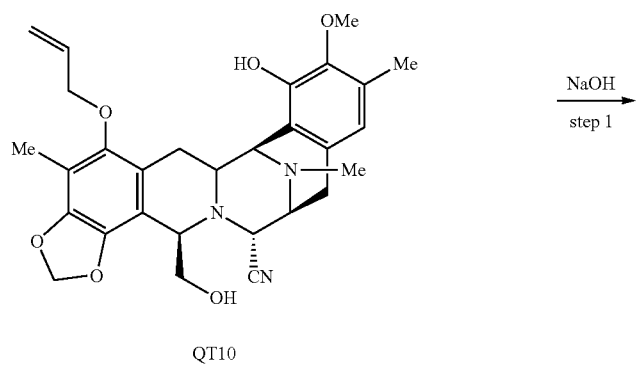
QT10
NaOH
step 1

-continued
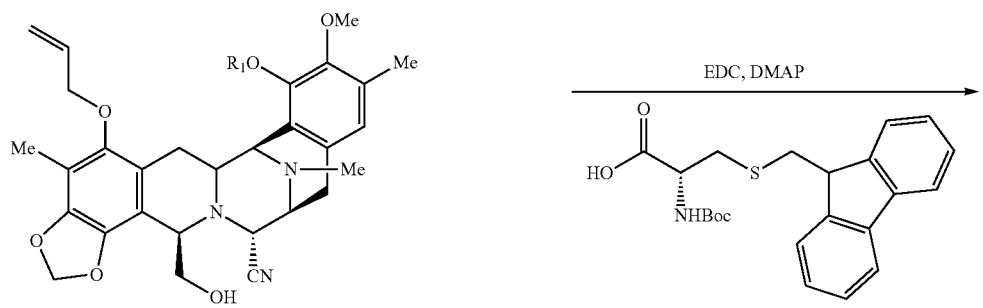
2 R$_1$ = MEM
3 R$_2$ = MOM
step2
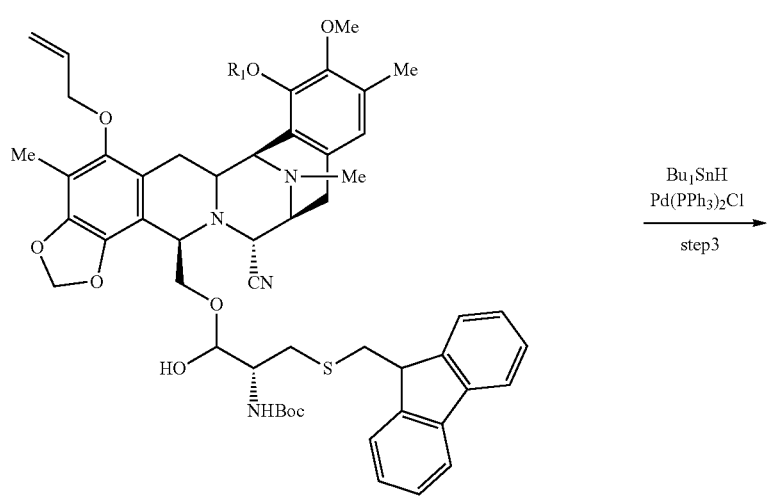
12 R$_1$ = MEM
13 R$_1$ = MOM
step3
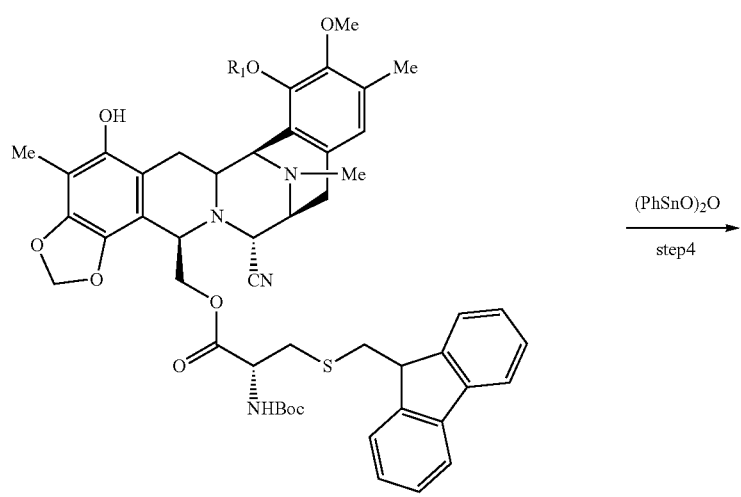
14 R$_1$ = MEM
15 R$_1$ = MOM
step4

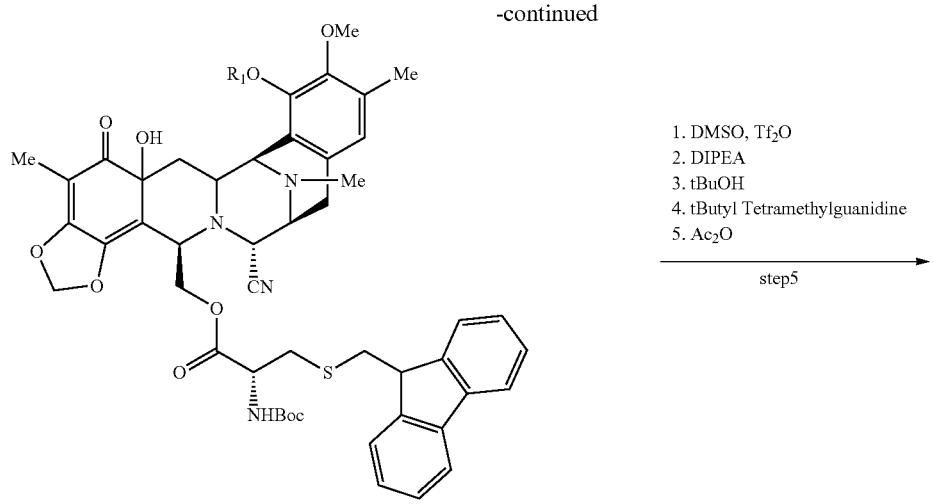
8 R₁ = MEM
9 R₁ = MOM
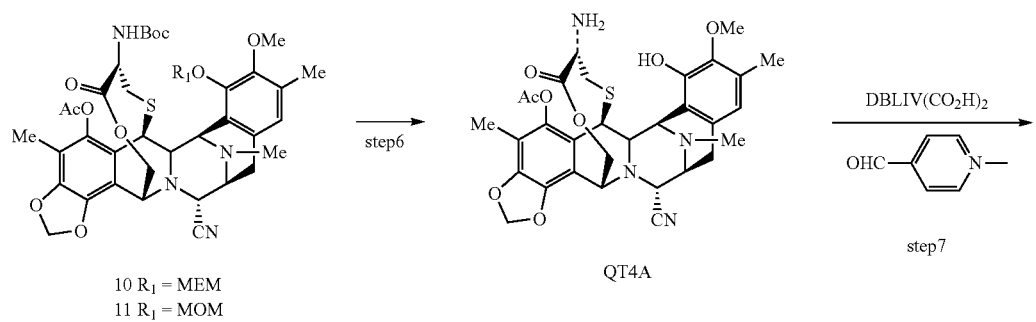
10 R₁ = MEM
11 R₁ = MOM
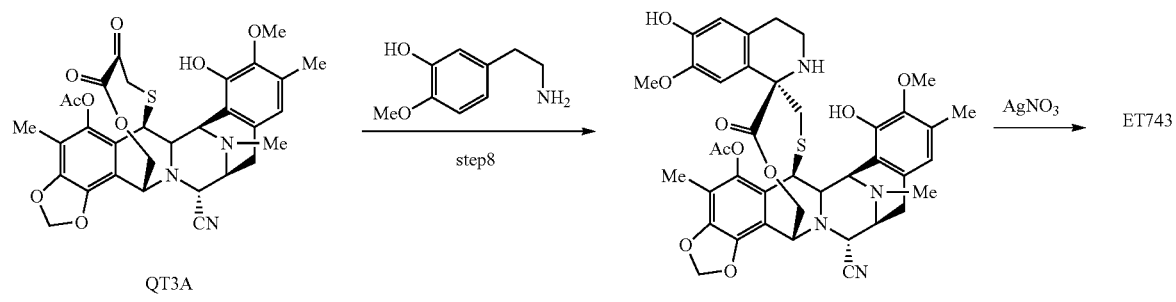
in which R₁ is MOM or MEM.

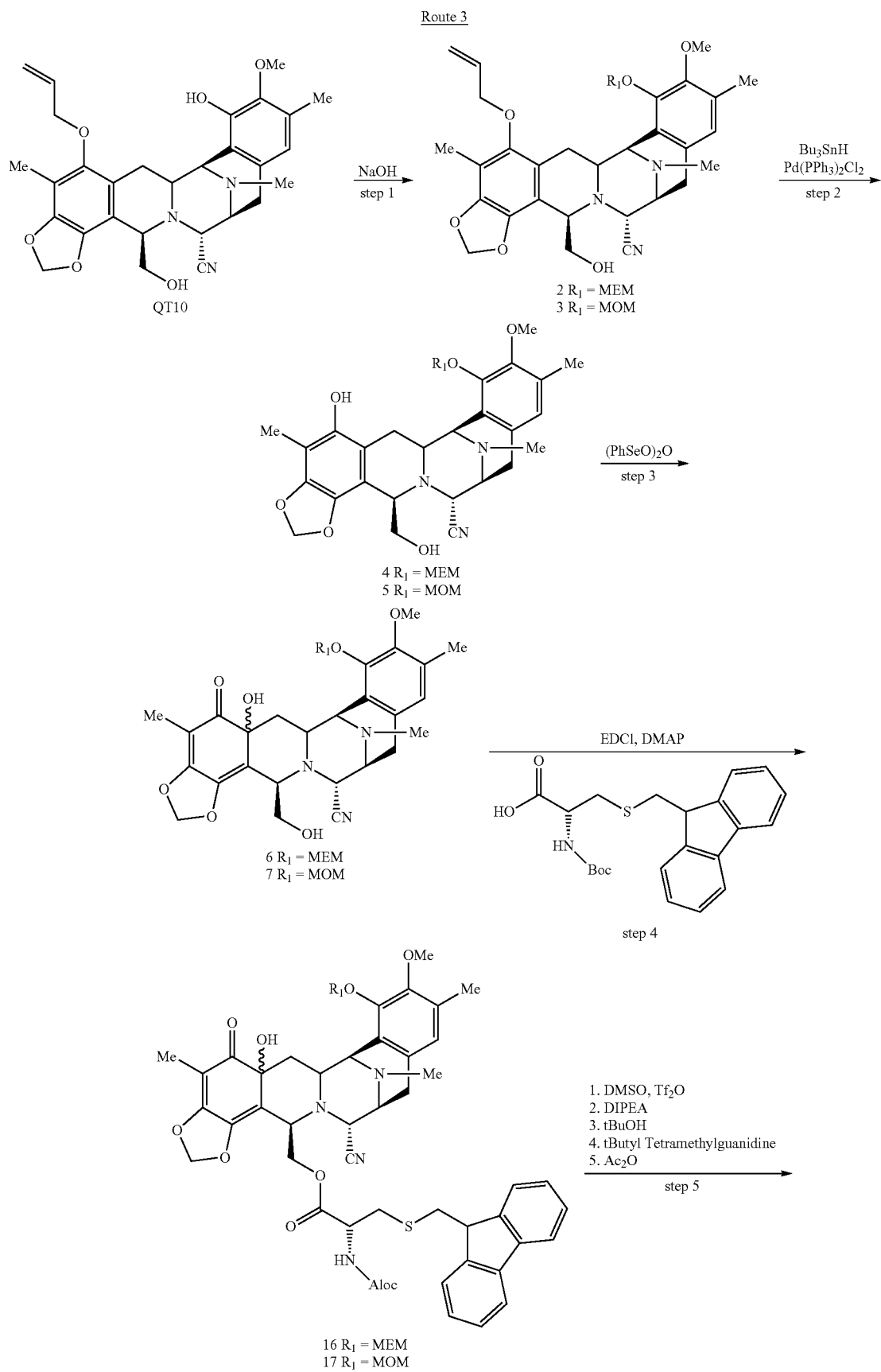

-continued
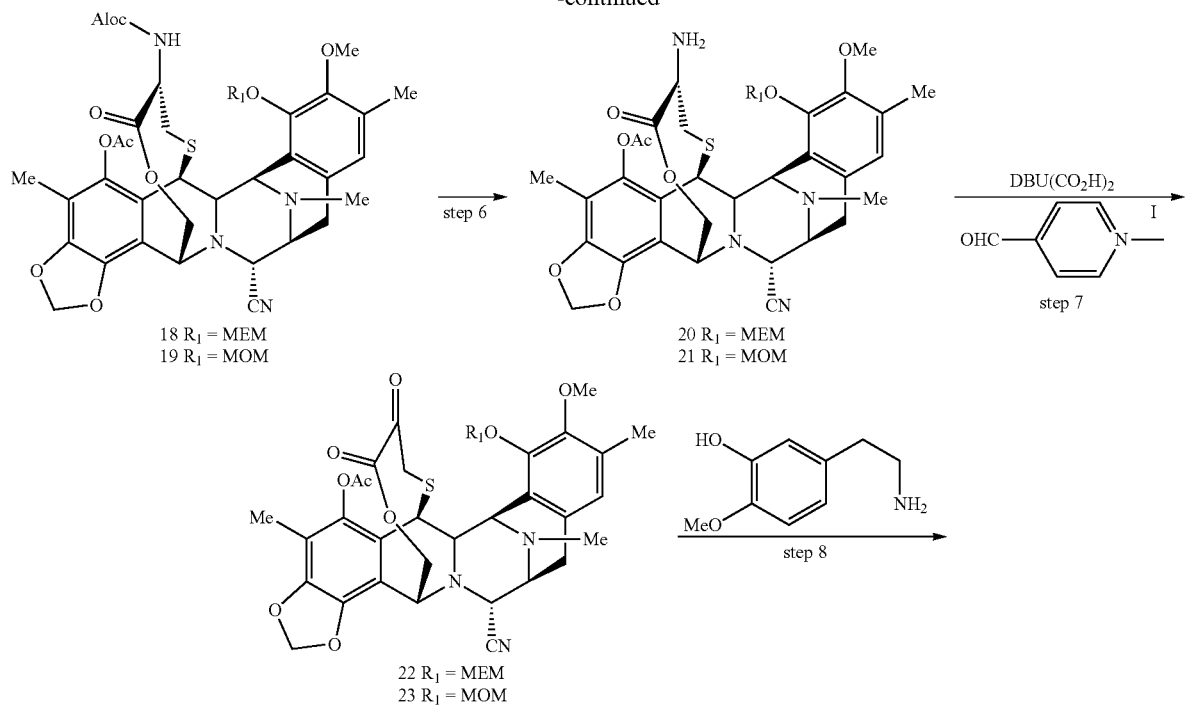
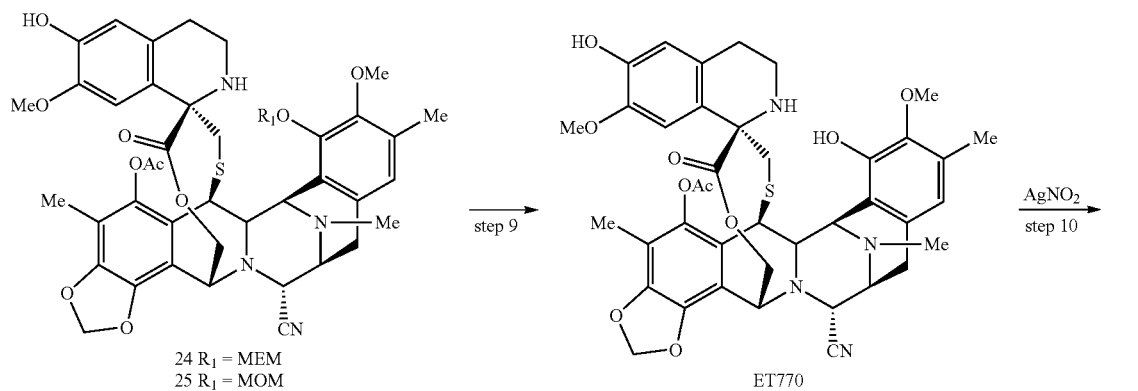
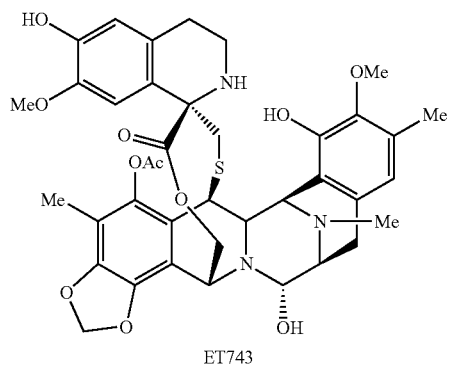
in which R₁ is MOM or MEM.

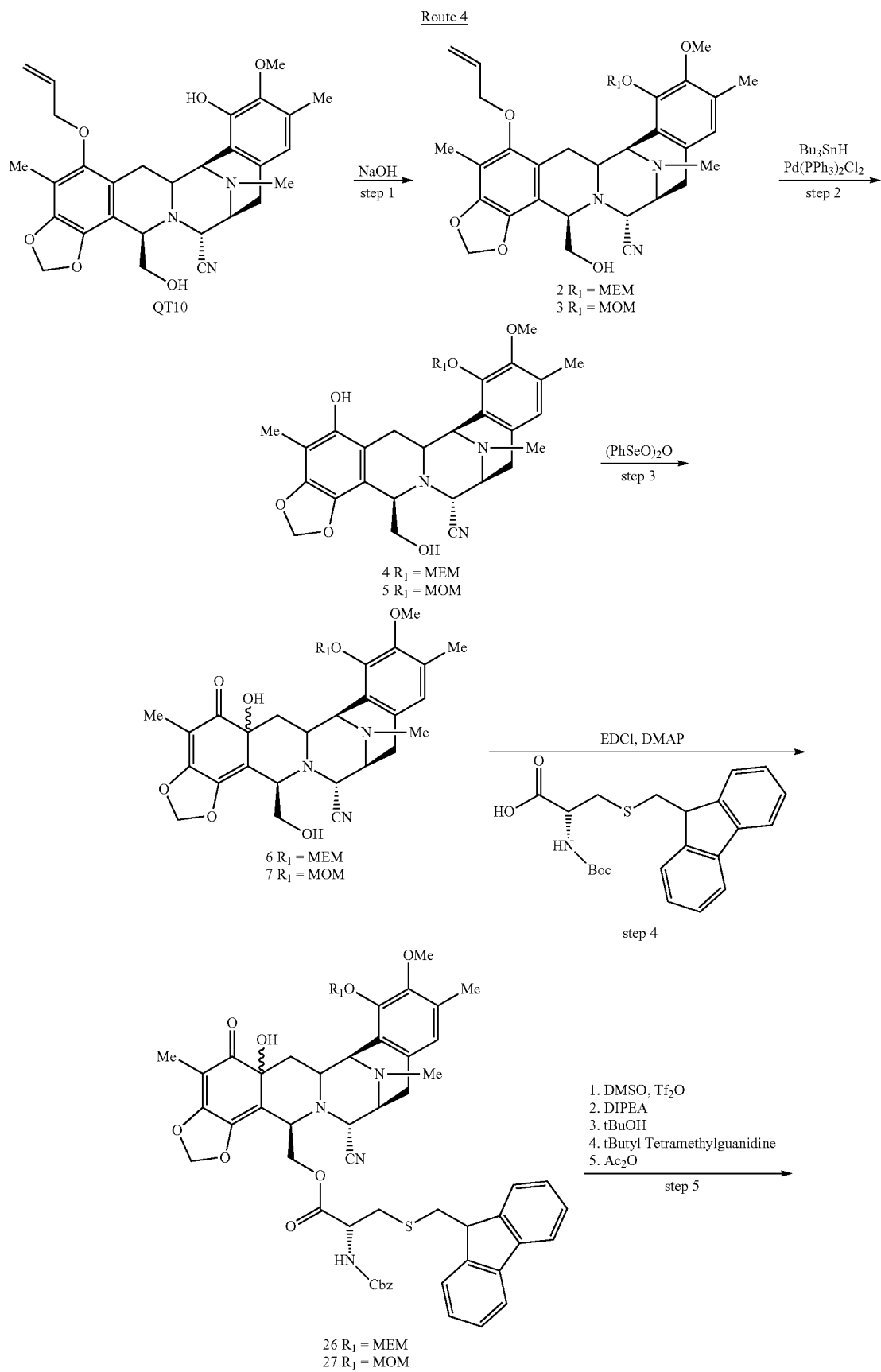
Route 4

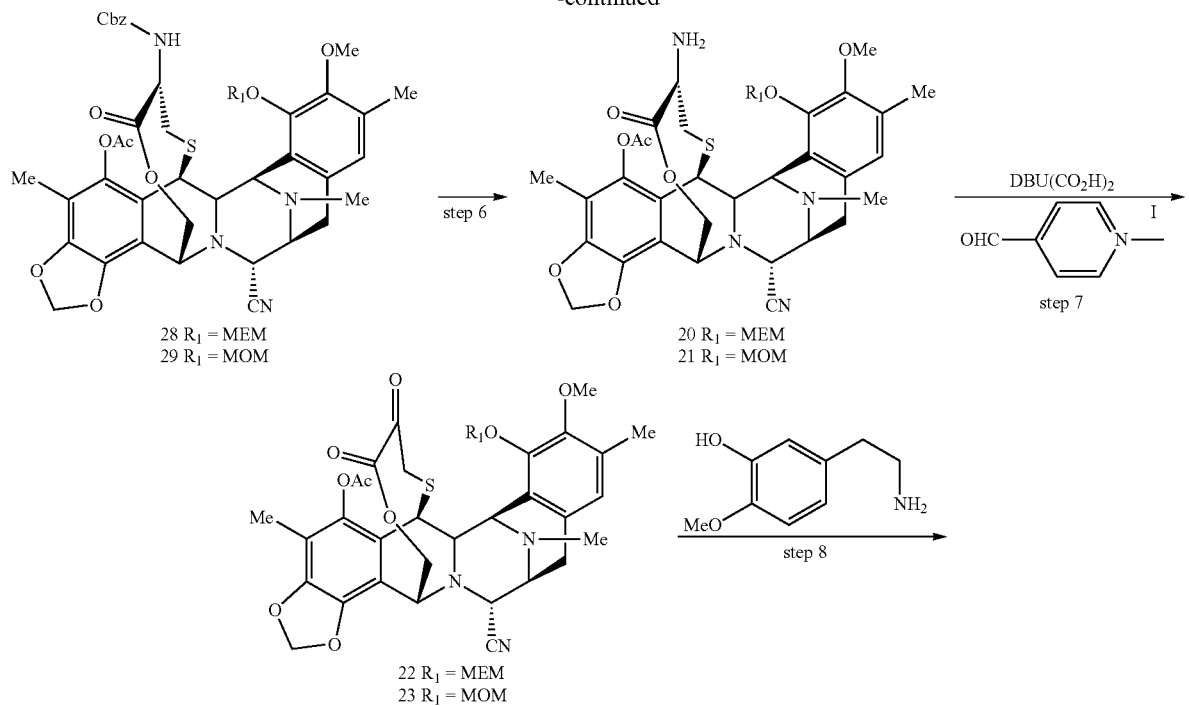
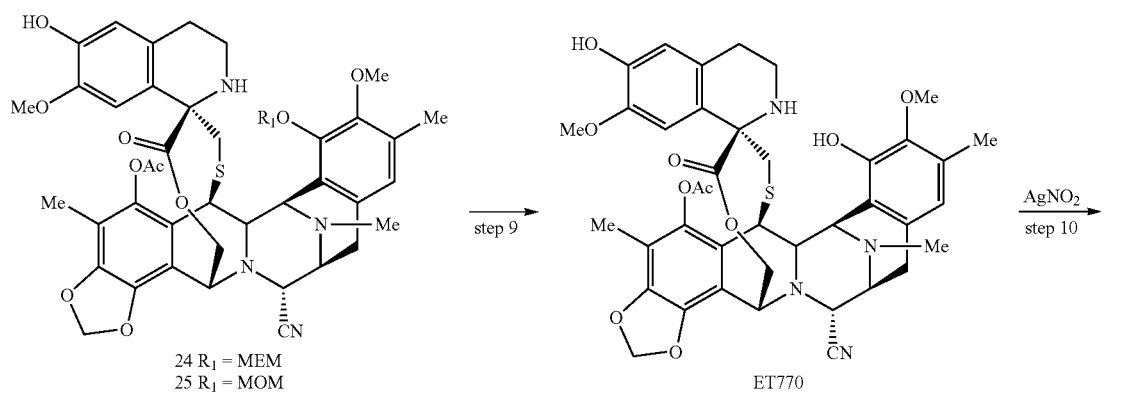
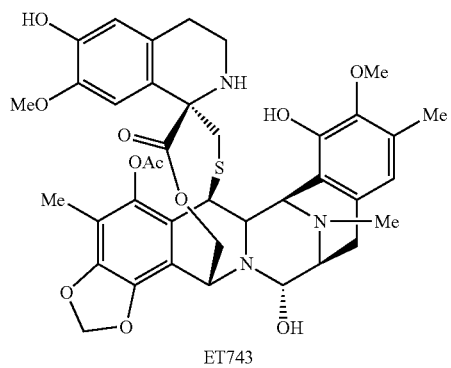
in which R₁ is MOM or MEM.

Route 5
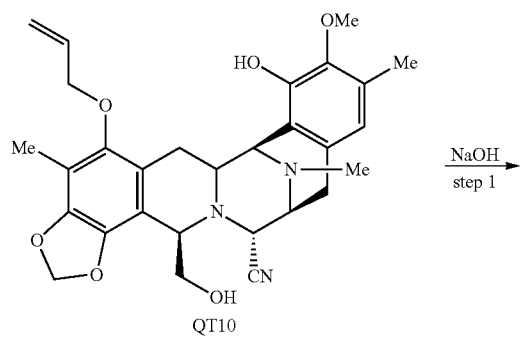
QT10
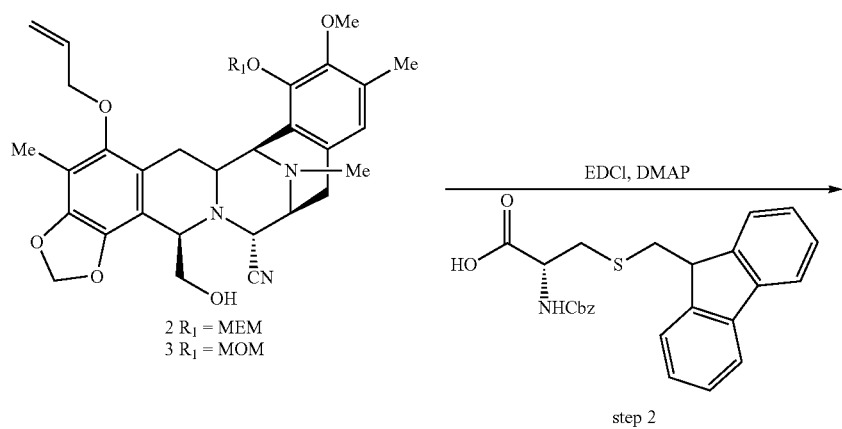
2 R₁ = MEM
3 R₁ = MOM
step 2
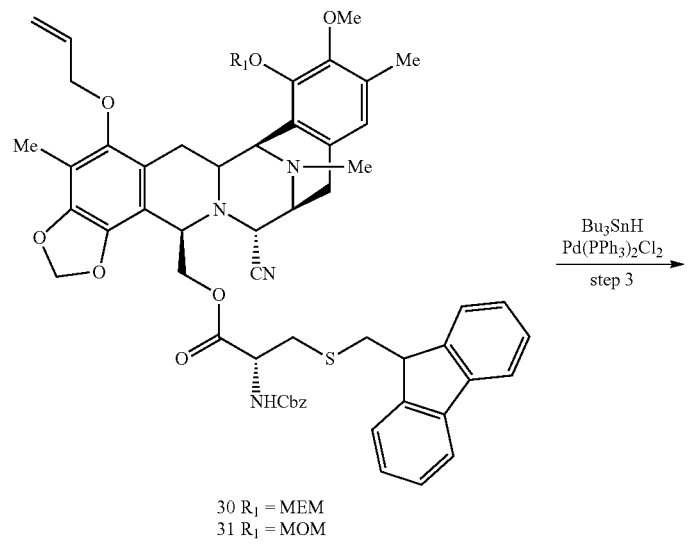
30 R₁ = MEM
31 R₁ = MOM -continued
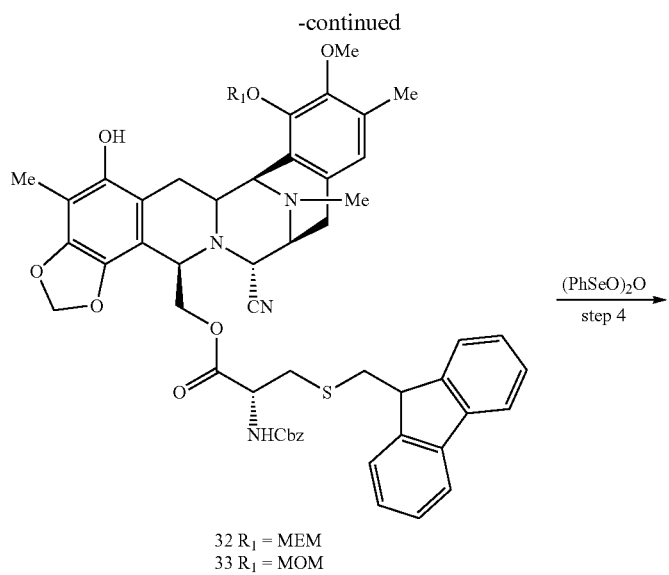
32 R₁ = MEM
33 R₁ = MOM
(PhSeO)₂O, step 4 →
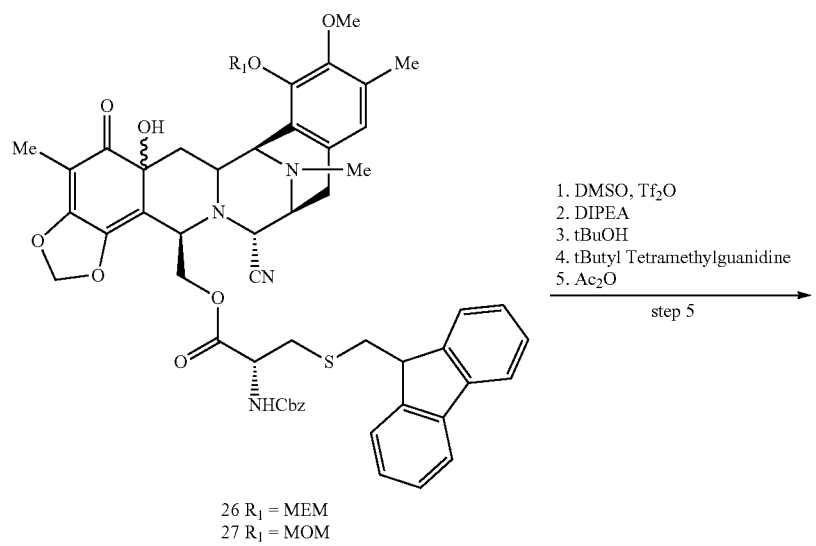
26 R₁ = MEM
27 R₁ = MOM
1. DMSO, Tf₂O
2. DIPEA
3. tBuOH
4. tButyl Tetramethylguanidine
5. Ac₂O
step 5 →
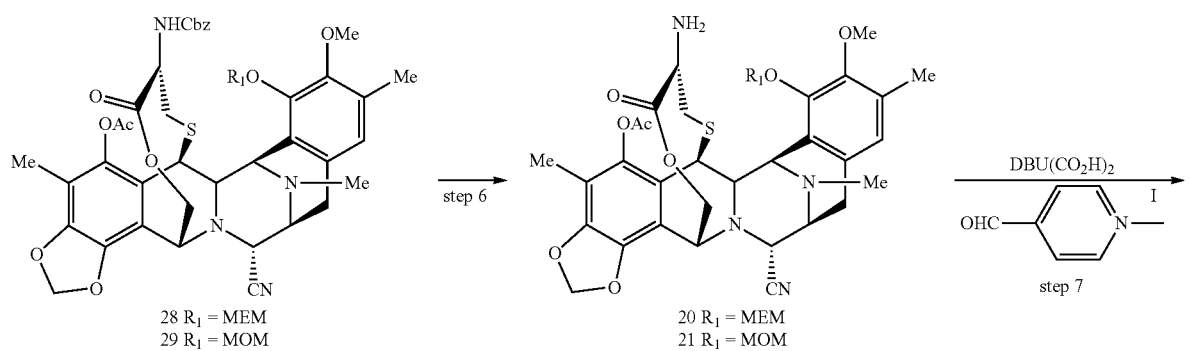
28 R₁ = MEM
29 R₁ = MOM
step 6 →
20 R₁ = MEM
21 R₁ = MOM
DBU(CO₂H)₂, step 7 →

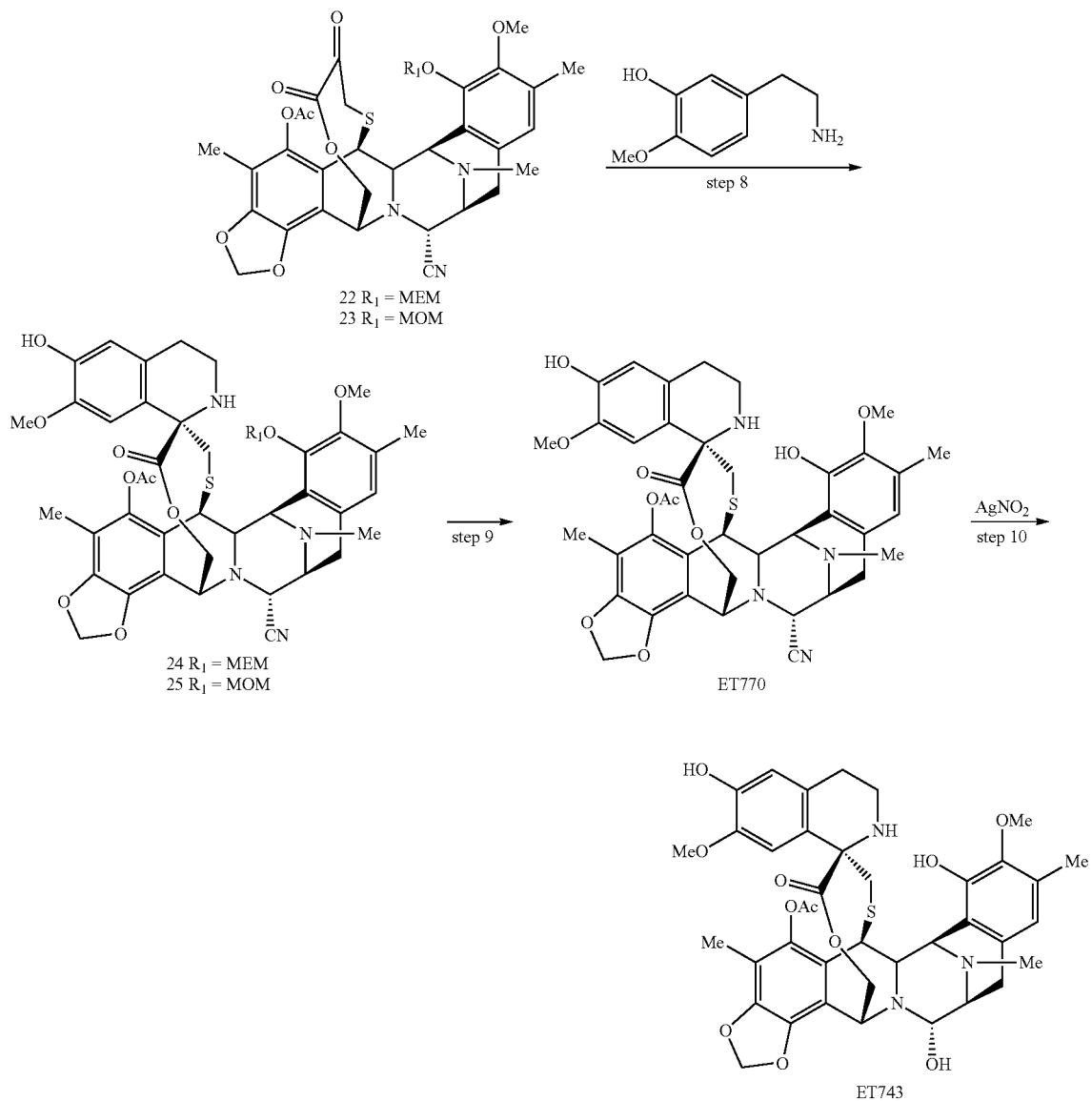
in which $R_1$ is MOM or MEM.
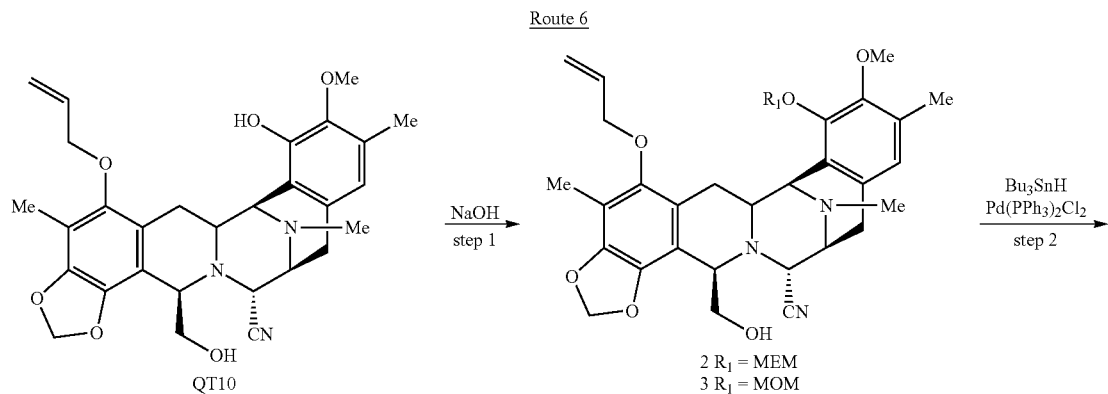

-continued
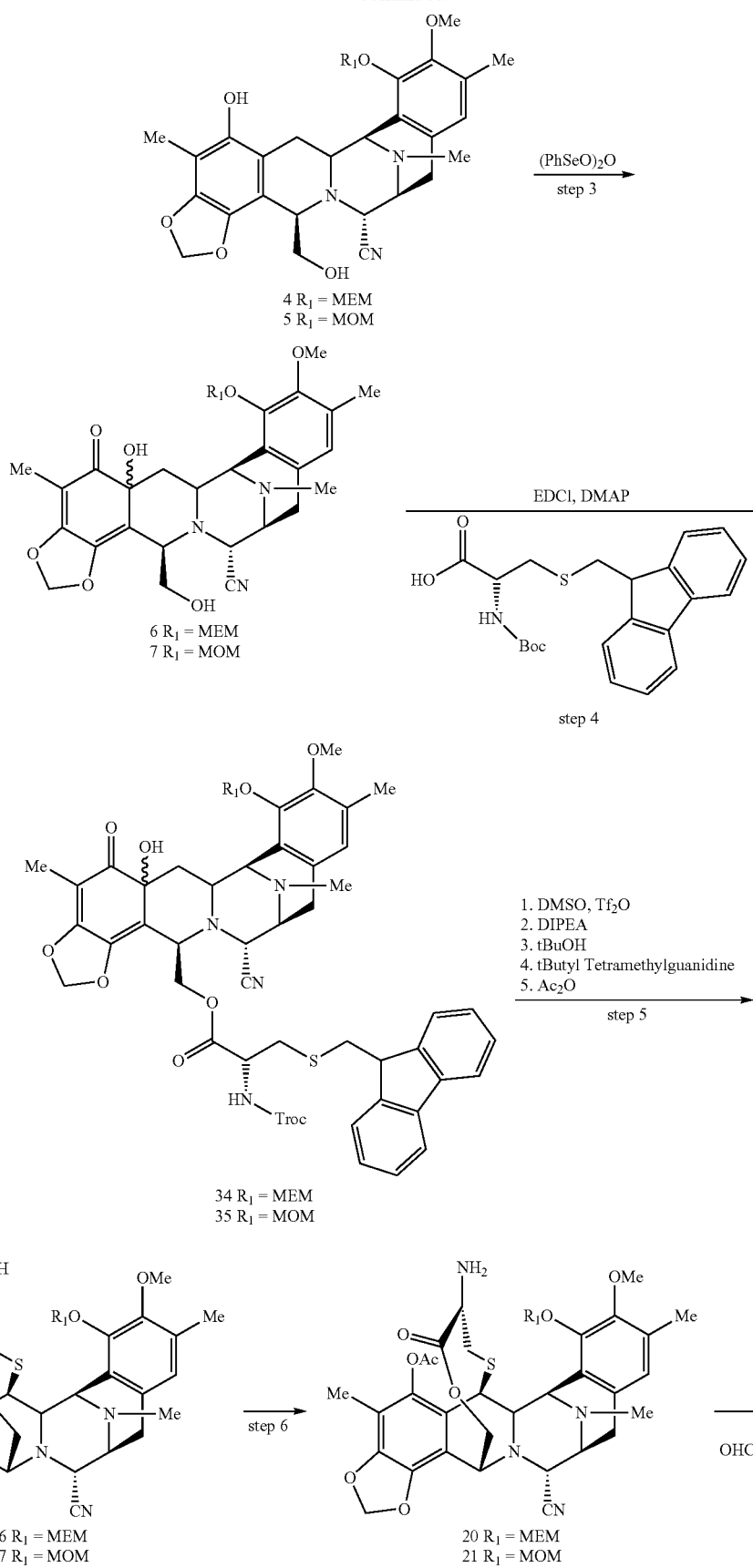

-continued
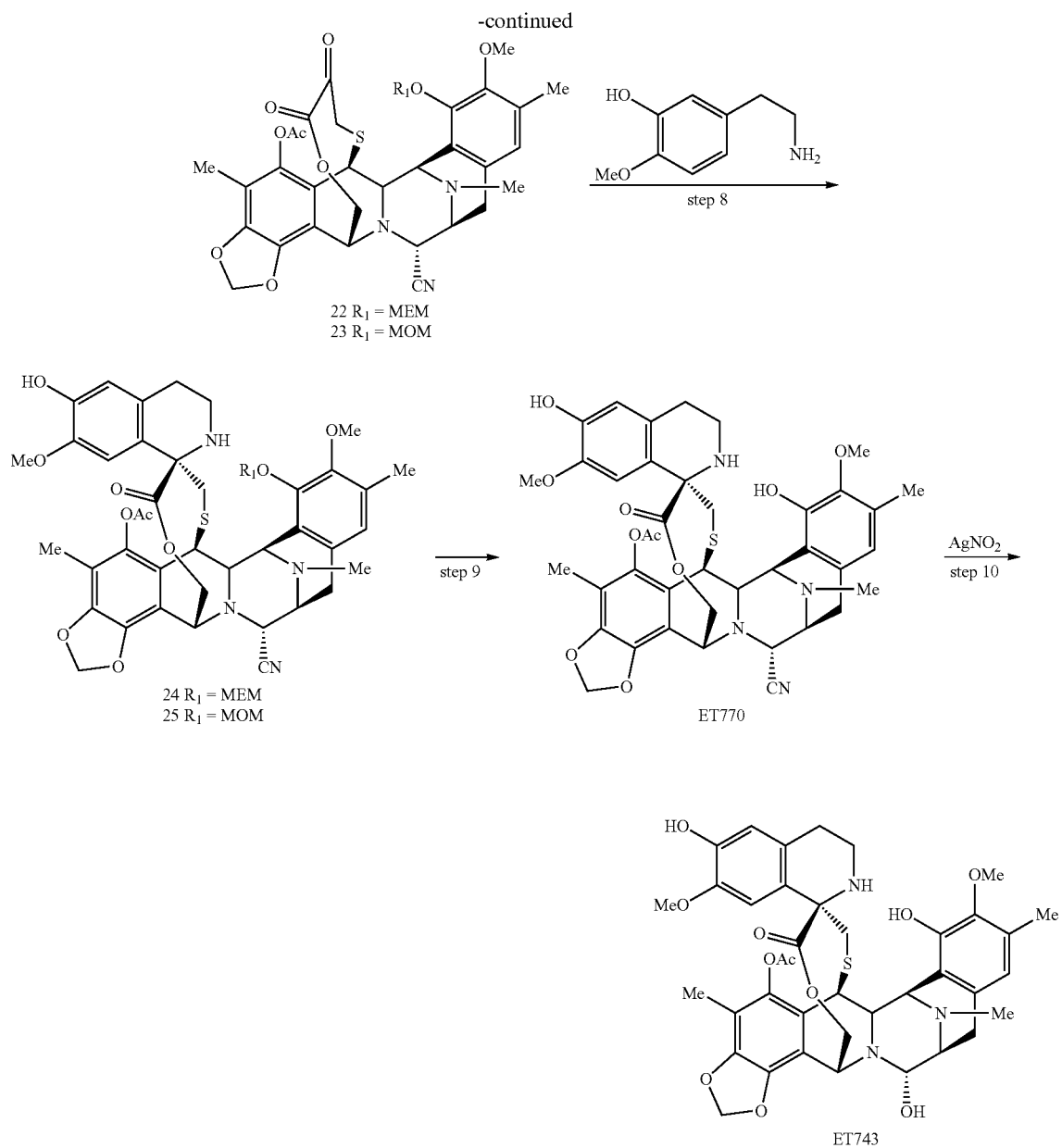
22 R₁ = MEM
23 R₁ = MOM
24 R₁ = MEM
25 R₁ = MOM
ET770
ET743
in which R₁ is MOM or MEM.
Route 7
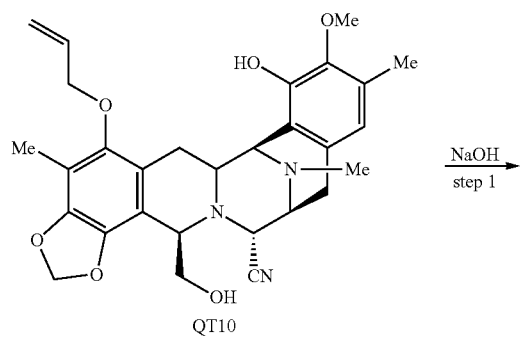
QT10

-continued
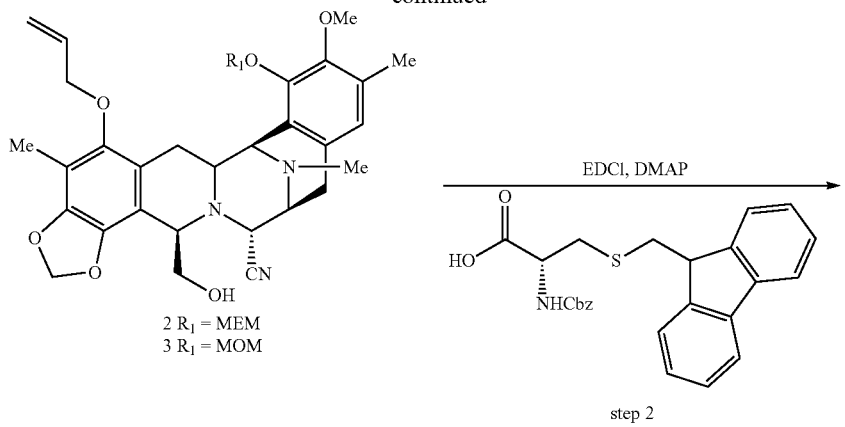
2 R$_1$ = MEM
3 R$_1$ = MOM
step 2
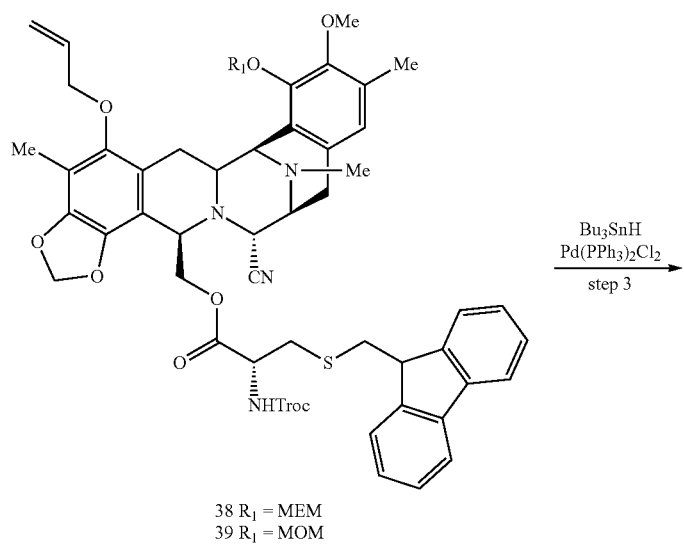
38 R$_1$ = MEM
39 R$_1$ = MOM
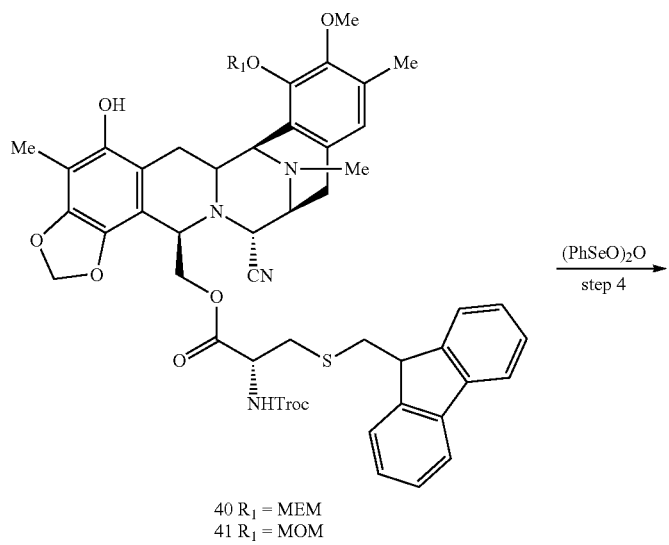
40 R$_1$ = MEM
41 R$_1$ = MOM -continued
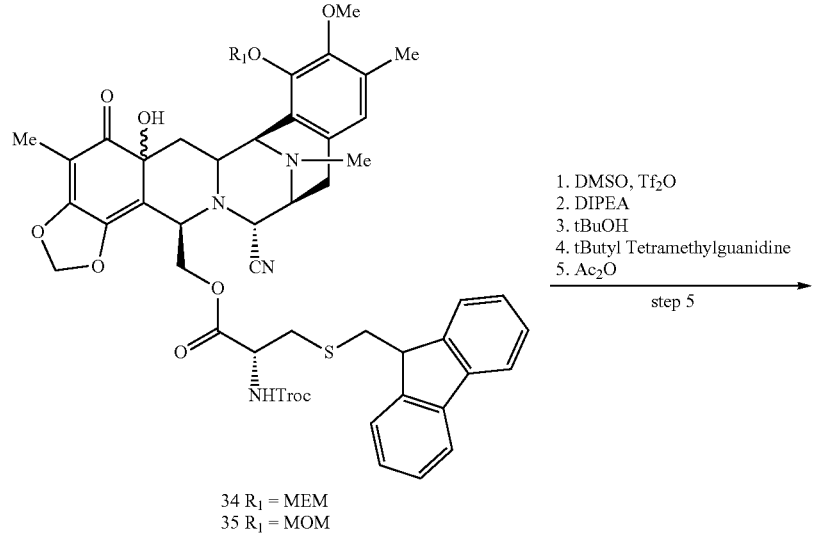
34 R₁ = MEM
35 R₁ = MOM
1. DMSO, Tf₂O
2. DIPEA
3. tBuOH
4. tButyl Tetramethylguanidine
5. Ac₂O
step 5
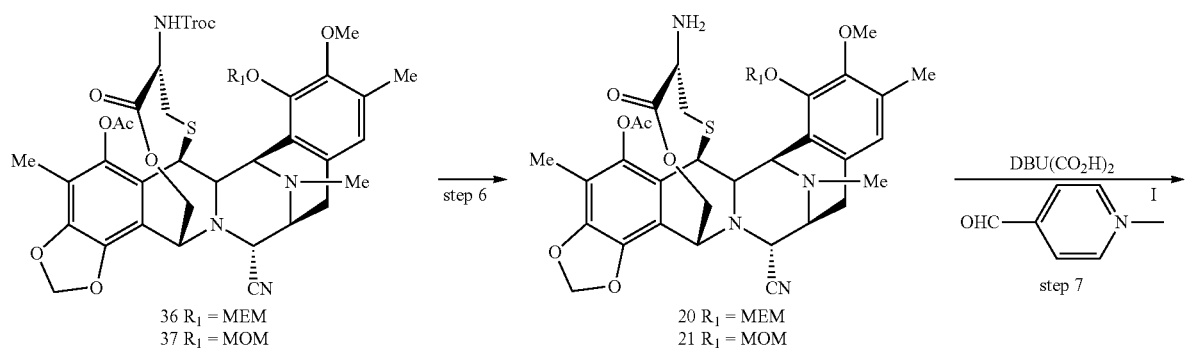
36 R₁ = MEM
37 R₁ = MOM
step 6
20 R₁ = MEM
21 R₁ = MOM
step 7
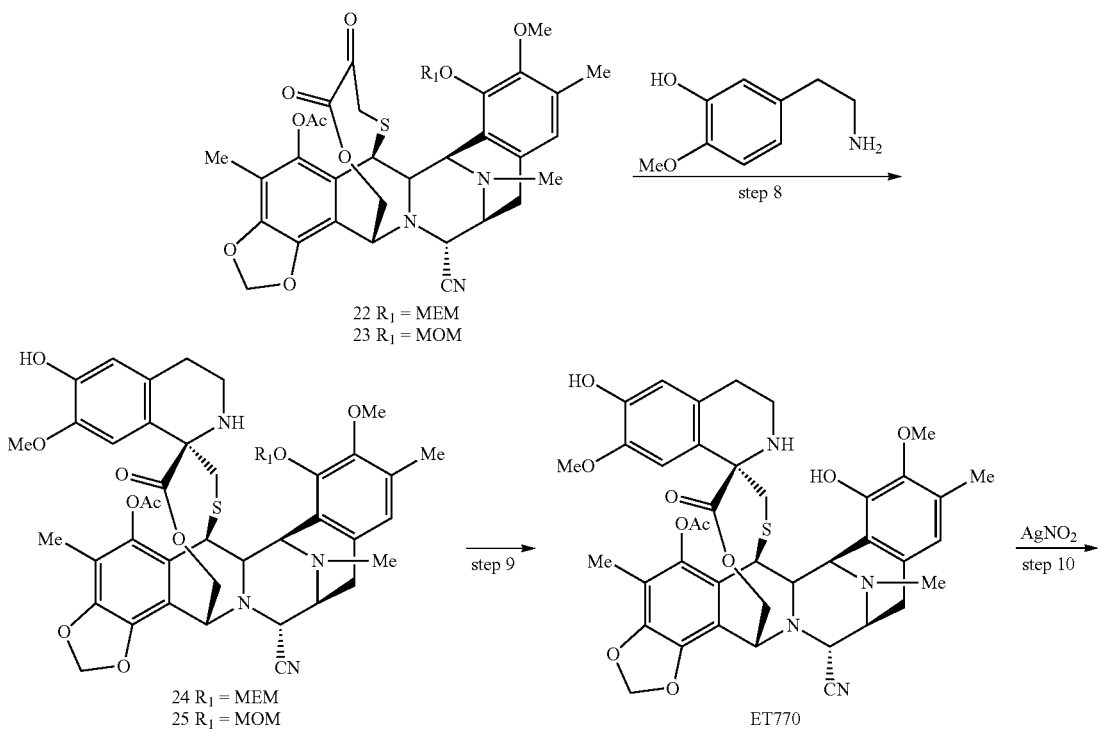
22 R₁ = MEM
23 R₁ = MOM
step 8
24 R₁ = MEM
25 R₁ = MOM
step 9
ET770
step 10

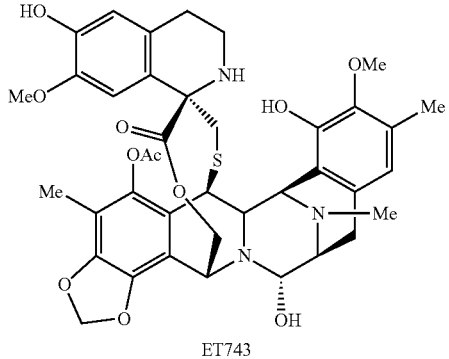 [SMILES: COc1cc2c(cc1O)CCN[C@]21CS[C@@H]2c3c(OC(C)=O)c(C)c4c(c3[C@H](COC1=O)N1C2[C@H]2c3c(cc(C)c(OC)c3O)C[C@@H]([C@@H]1O)N2C)OCO4 ; "ET743"]

ET743 in which R₁ is MOM or MEM.

In addition, the present invention further provides an intermediate having the following structure for preparing an ecteinascidin compound:

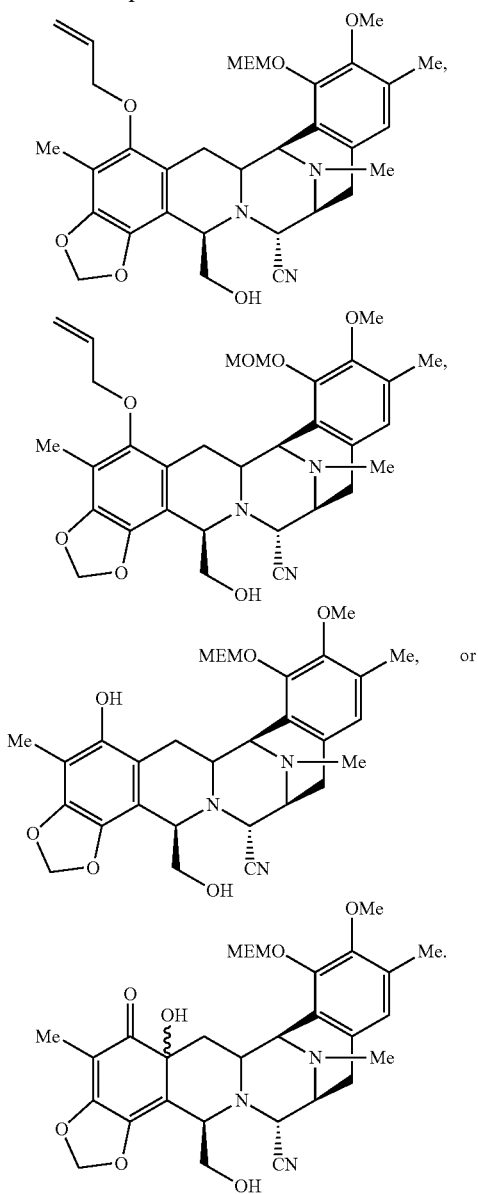

or

An advantage of the present invention is that a new method for preparing compound QT9 and a method for preparing trabectedin from the compound QT9 are provided, wherein in the methods provided by the present invention, a plurality of intermediates such as QT9, QT8, QT7, QT4 and QT5 are all in a solid form and are easy to purify and store; among them, compounds QT9, QT4 and QT5 can all be purified by means of crystallization, with both the yield and purity being very high; in particular, the compound QT9 can be purified by means of crystallization from various solvents; the overall route is very suitable for industrial applications. With regard to the method provided by the present invention, since the reactions for preparing a plurality of intermediates, particularly compounds QT9, QT4 and QT5 in the reaction process have properties of high selectivity, high conversion efficiency, and easy purification, and a plurality of intermediates have higher purities, thereby greatly improving the yields of the reactions in the subsequent steps, thus significantly increasing the overall yield of trabectedin. Furthermore, the defects of a plurality of intermediates for preparing trabectedin being oil and difficult to purify in the prior art are overcome.

Secondly, in the method provided by the present invention, the reaction selectivity for the protection and deprotection of the phenol hydroxyl group and the protection of the primary hydroxyl group are high, and the yield and purity of the product are both significantly improved; particular in the process of the preparation of the compound QT9, the inventors have found through a large number of experimental design studies that where sodium hydroxide or sodium hydride is used as a base in the reaction system, the reaction conversion rate is very high, for example, it may be close to 100%, and the yield of the resulting product QT9 is significantly improved, for example, it may be up to 98%, leading to easy handle after reaction.

Since the reactivities of the phenol hydroxyl group and the primary hydroxyl group are relatively close, when protection is carried out on the phenol hydroxyl group, a side reaction of simultaneously protecting the primary hydroxyl group easily occurs, so that it is usually necessarily for a person skilled in the art to protect the primary hydroxyl group prior to the protection of the phenol hydroxyl group with MEM or MOM, and in the subsequent reaction process, it is further necessarily to remove the protecting group on the primary hydroxyl group, causing the operation to be cumbersome; furthermore, the protecting group on the phenol hydroxyl group is easy to remove during the removal of the primary hydroxyl protecting group, and there are many by-products in the reaction product, thereby resulting in purification difficulties. Compared with the solutions disclosed in the prior art, the present invention directly selectively protects the phenol hydroxyl group without protection on the primary hydroxyl group, thus omitting the process of the two reaction steps of protecting and deprotecting the primary hydroxyl group; furthermore, the reaction selectivity is high, and the double-protected by-product is very few and can be removed by means of recrystallization, which greatly simplifies the operation steps and production cycle, so that it is very suitable for industrialization.

The content and preferred embodiments of the present invention are further explained below in conjunction with specific examples.

5. EXAMPLES

Example 1: Synthesis of Compound 2

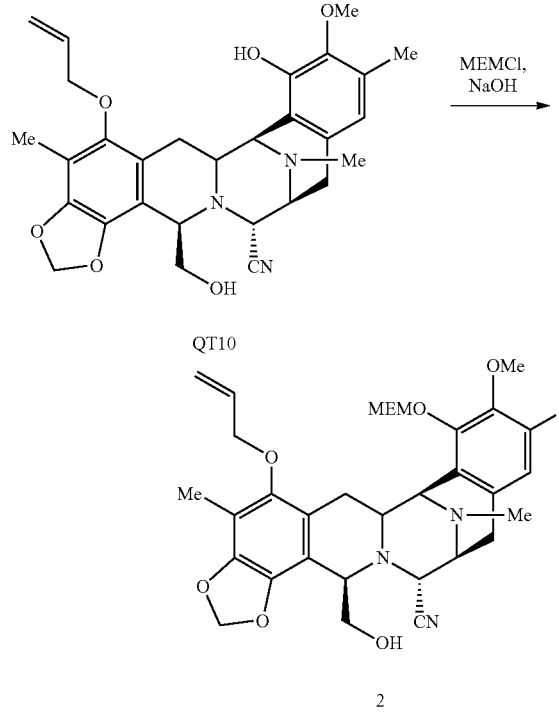

2

To a 1000 ml three-necked flask, 6.9 g of sodium hydroxide and 250 ml of tetrahydrofuran are added, and after the temperature is reduced to 0° C. or less, 59.8 g of compound QT10 is added, and 21.5 g of 2-methoxyethoxymethyl chloride (MEM-Cl) is dropwise added. After the dropwise addition is completed, with the temperature being maintained at 0° C. to 10° C., the reaction is stirred for 4 hours, quenched by adding a saturated ammonium chloride aqueous solution, and extracted with dichloromethane (2×500 ml); the organic layers are combined, dried over anhydrous sodium sulfate, and concentrated in vacuo; and the resulting viscous material is recrystallized from ethyl acetate and n-hexane to obtain 64.2 g of the compound as a white solid, with a yield of 91.8% and HPLC >99%.

$^1$HNMR (400MHZ, CDC$_3$): δ 6.71 (s, 1H), 06.10 (m, 1H), 5.93 (d, J=1.2 Hz, 1H), 5.87 (d, J=1.2 Hz, 1H), 5.44 (dd, J1=1.2 Hz, J2=17.2 Hz, 1H), 5.30 (dd, J1=1.2 Hz, J2=10.4 Hz, 1H), 5.27 (d, J=6 Hz, 1H), 5.18 (d, J=6 Hz, 1H), 4.26 (d, J=2.4 Hz, 1H), 4, 18-4.14 (m, 2H), 4.04 (d, J=2.4 Hz, 1H), 3.99 (t, 2H), 3.86 (m, 1H), 3.66 (s, 3H), 3.64 (m, 1H), 3.60 (t, 2H), 3.42-3.32 (m, 3H), 3.37 (s, 3H), 3.25 (dd, J1=2.8 Hz, J2=16 Hz, 1H), 3.14 (dd, J1=8.4 Hz, J2=17.4 Hz, 1H), 2.53 (d, J=18.4 Hz, 1H), 2.37 (s, 3H), 2.21 (s, 3H), 2.12 (s, 3H), 1.86-1.57 (m, 2H); MS: m/z (607.69), Found: 608.2 (M+H)$^+$.

Example 2: Synthesis of Compound 3

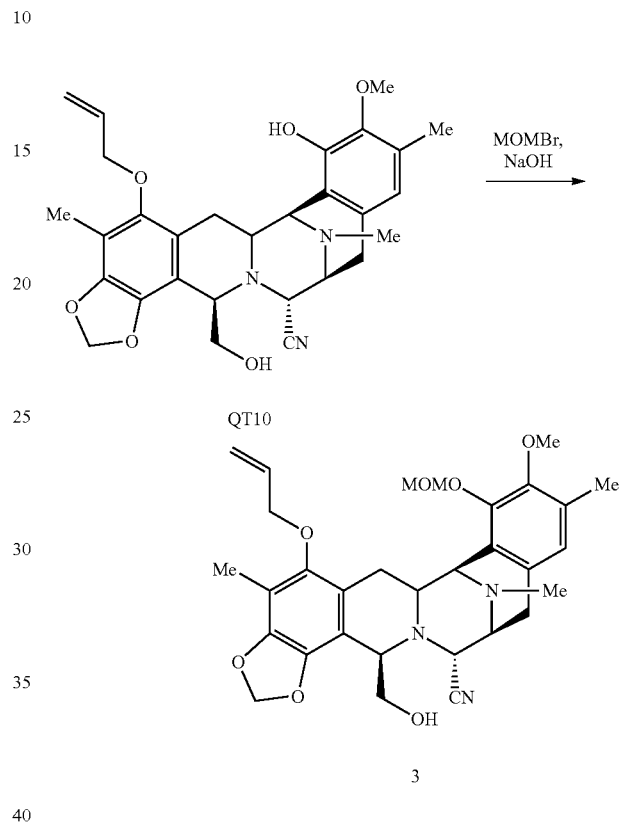

3

To a 500 ml three-necked flask, 1.15 g of sodium hydroxide and 115 ml of tetrahydrofuran are added, and after the temperature is reduced to 0° C. or less, 10.0 g of compound QT10 is added, and 2.41 g of bromomethyl methyl ether (MOM-Br) is dropwise added. After the dropwise addition is completed, with the temperature being maintained at −5° C. to 5° C., the reaction is stirred for 2 hours, quenched by adding a saturated ammonium chloride aqueous solution, and extracted with dichloromethane (2×200 ml); the organic layers are combined, dried over anhydrous sodium sulfate, and concentrated in vacuo; and the resulting foamy solid is recrystallized from ethyl acetate and n-hexane to obtain 9.8 g of the compound as a white solid, with a yield of 90.3% and HPLC >99%.

$^1$HNMR (400MHZ, CDCl$_3$): δ6.72 (s, 1H), 6.16-6.07 (m, 1H), 5.93 (d, J=1.6 Hz, 1H), 5.88 (d, J=1.6 Hz, 1H), 5.44 (dd, J1=1.6 Hz, J2=17.2 Hz, 1H), 5.30 (dq, J1=1.2 Hz, J2=10.4 Hz, 1H), 5.12 (s, 2H), 4.27 (d, J=2.0 Hz, 1H), 4, 12-4.11 (m, 2H), 4.05 (d, J=2.4 Hz, 1H), 3.99 (t, J=3.2 Hz, 2H), 3.71 (s, 3H), 3.68-3.63 (dt, J1=3.2 Hz, J2=10.8 Hz, 1H), 3.59 (s, 3H), 3.49-3.33 (m, 3H), 3.27 (dd, J1=2.8 Hz, J2=16.0 Hz, 1H), 3.16 (dd, J1=7.6 Hz, J2=18.0 Hz, 1H), 2.54 (d, J=18.0 Hz, 1H), 2.37 (s, 3H), 2.22 (s, 3H), 2.12 (s, 3H), 1.86-1.81 (dd, J1=12 Hz, J2=15.6 Hz, 1H), 1.79-1.75 (dd, J1 =2.8 Hz, J2=10.4 Hz, 1H); MS: m/z (563.64), Found: 564.5 (M+H)$^+$.

Example 3: Example 3 Synthesis of Compound 4

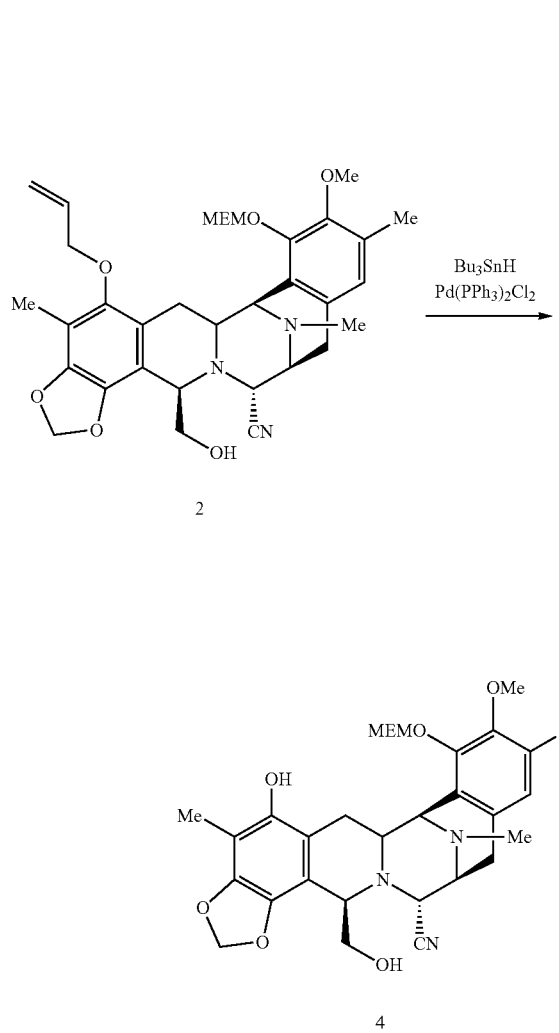

Under argon protection, to a 100 ml three-necked flask, 3.0 g of compound 2, 0.241 g of bis(triphenylphosphine) palladium dichloride, 1.48 g of acetic acid and 60 ml of dichloromethane are added, and 3.57 g of tri-n-butyl tin hydride is added at −15° C. to −10° C.; after the addition is completed, with the temperature being maintained at 0° C. to 5° C., the reaction is stirred for 1 hour, quenched by adding a saturated potassium fluoride aqueous solution and extracted with dichloromethane (2×40 ml); and the organic layers are combined, dried over anhydrous sodium sulfate and concentrated in vacuo to obtain an oil, which is subjected to column chromatography (n-hexane:ethyl acetate=4:1 to 1:1) to obtain 2.76 g of the compound as a white foamy solid, with a yield of 98.5% and HPLC >98%.

$^1$HNMR (400MHZ, CDCl$_3$): δ6.68 (s, 1H), 5.89 (d, J=1.2 Hz, 1H), 5.82 (d, J=1.2 Hz, 1H), 5.44 (dd, J1=1.2 Hz, J2=17.2 Hz, 1H), 5.30 (dd, J1=1.2 Hz, J2=10.4 Hz, 1H), 5.61 (s, 1H), 5.39 (d, J=6 Hz, 1H), 5.27 (d, J=6 Hz, 1H), 4.26 (d, J=2.4 Hz, 1H), 4, 13-4.066 (m, 2H), 3.99-3.93 (m, 2H), 3.69 (s, 3H), 3.68-3.65 (m, 3H), 3.60 (t, 1H), 3.40 (s, 3H), 3.37-3.76 (m, 2H), 3.25 (dd, J=3.2, J2=14.2, 1H), 3.13 (dd, J1=8.4 Hz, J2=18.4 Hz, 1H), 2.53 (d, J=18.0 Hz, 1H), 2.34 (s, 3H), 2.20 (s, 3H), 2.08 (s, 3H), 1.83-1.77 (m, 2H); MS: m/z (567.63), Found: 568.6 (M+H)$^+$.

Example 4: Example 4 Synthesis of Compound 5

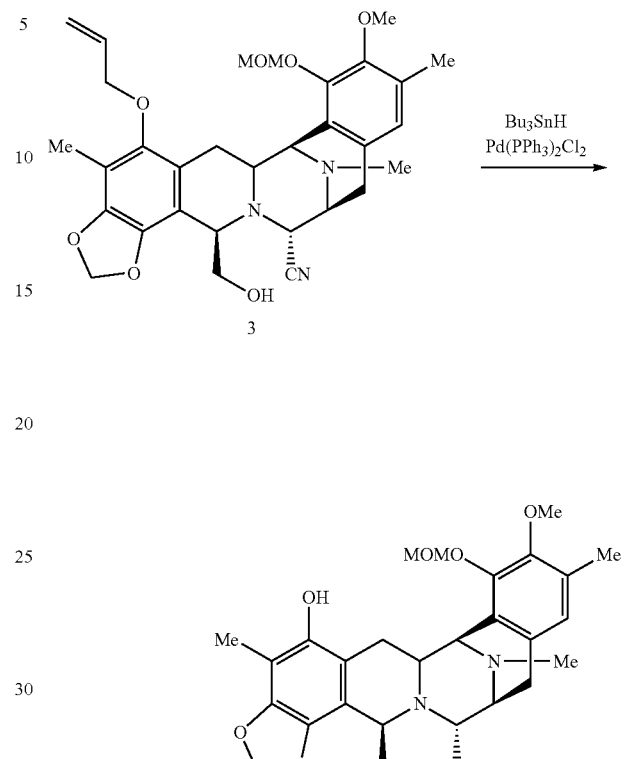

With reference to a similar method to example 3, the compound is prepared from compound 3, with a yield of 97.3% and HPLC >96%.

$^1$HNMR (400MHZ, CDC$_3$): δ6.72 (s, 1H), 6.16-6.07 (m, 1H), 5.93 (d, J=1.6 Hz, 1H), 5.88 (d, J=1.6 Hz, 1H), 5.44 (dd, J1=1.6 Hz, J2=17.2 Hz, 1H), 5.36-5.30 (m, 1H), 5.19 (t, J=6.5 Hz, 1H), 4.28 (d, J=2.4 Hz, 1H), 4.10 (d, J=2.4 Hz, 1H), 4.05-3.98 (m, 1H), 3.70 (dd, J1=5.6 Hz, J2=16.0 Hz, 7H), 3.56 (m, 1H), 3.44-3.36 (m, 2H), 3.18-3.07 (m, 2H), 2.54 (d, J=2.0 Hz, 1H), 2.38 (d, J=5.6 Hz, 3H), 2.25 (d, J=11.2 Hz, 3H), 2.10 (s, 3H), 1.84 (dd, J=15.2 Hz, 2H); MS: m/z (523.58), Found: 524.5 (M+H)$^+$.

Example 5: Example 5 Synthesis of Compound 6

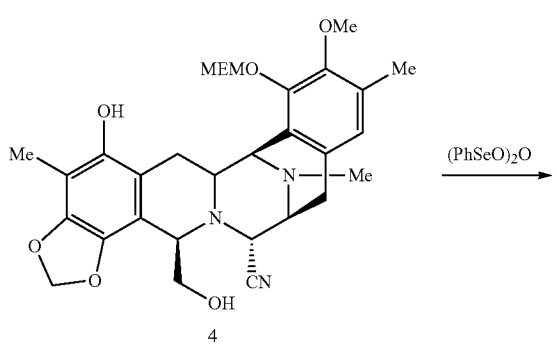

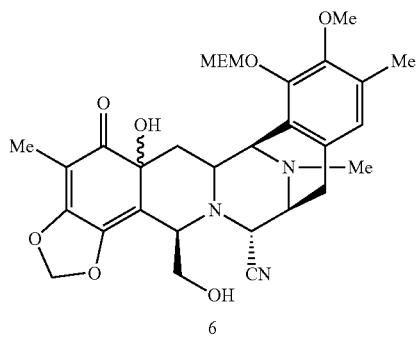

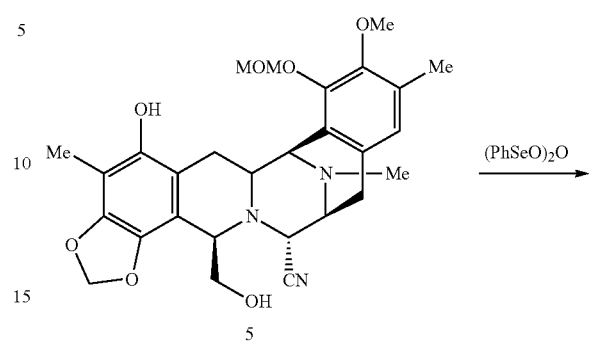

Example 6: Example 6 Synthesis of Compound 7

Under argon protection, to a 250 ml three-necked flask, 2.7 g of compound 4 and 40 ml of dichloromethane are added, and after the temperature is reduced to −40° C. to −35° C., a solution of 1.71 g of benzeneseleninic anhydride in dichloromethane is added; with the temperature being maintained constant, the reaction is stirred for 1 hour, quenched by adding a saturated sodium bicarbonate aqueous solution and allowed for layering; the aqueous layer is extracted with dichloromethane (2×40 ml), and the organic layers are combined, dried over anhydrous sodium sulfate and concentrated in vacuo to obtain an oil, which is subjected to column chromatography (n-hexane:ethyl acetate=4:1 to 1:1) to obtain 2.66 g of the compound as a light yellow solid, with a yield of 95.8% and HPLC >96%.

¹HNMR (400MHZ, CDCl₃): δ6.69, 6.62 (s, 1H), 5.84, 5.74 (s, 2H), 5.26, 5.08 (d, J=1.2 Hz, 1H), 5.15 (d, J=1.5 Hz, 1H), 5.61 (s, 1H), 4.23-3.30 (m, 11H), 3.90, 3.62 (s, 3H), 3.39, 3.36 (s, 3H), 3.024-2.959 (m, 1H), 2.80-2.09 (m, 2H), 2.30, 2.24 (s, 3H), 2.22, 2.19 (s, 3H), 1.80 (s, 3H); MS: m/z (583.63), Found: 584.65 (M+H)⁺.

With reference to a method of example 5, compound 7 is prepared from compound 5 and obtained as a light yellow solid (8.0 g), with a yield of 97.0% and HPLC >96%.

¹HNMR (400MHZ, CDCl₃): δ6.72 (s, 1H), 5.86 (m, 1H), 5.93 (s, 2H), 5.12 (s, 2H), 4.10 (m, 2H), 3.92 (s, 3H), 3.88 (m, 1H), 3.80 (m, 1H), 3.62 (m, 1H), 3.52 (s, 3H), 3.34 (m, 1H), 3.04 (dd, J1=7.6, J2=18.0, 1H), 2.68 (m, 1H), 2.62 (d, J=18, 1H), 2.32 (s, 3H), 2.24 (s, 3H), 2.21 (m, 1H), 2.00 (dd, J1=8.4, J2=15.2, 1H), 1.80 (s, 31H).

Example 7: Example 7 Synthesis of Compound 8

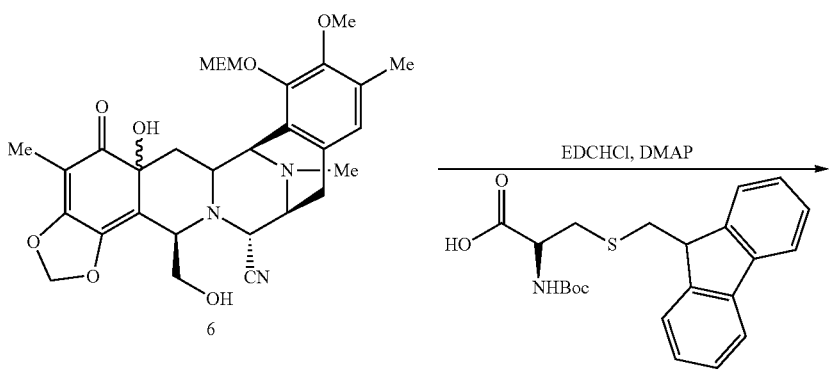

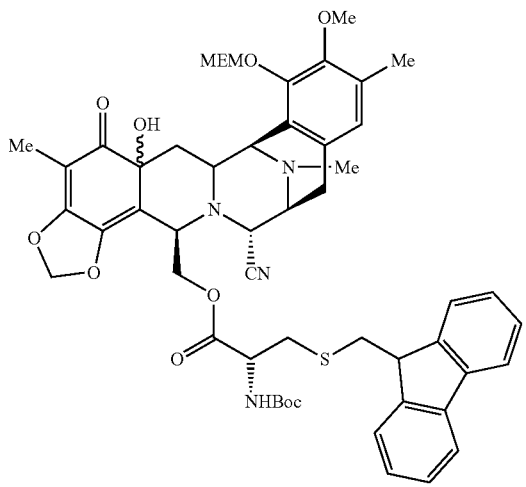

8

2.5 g of compound 6 and 2.57 g of N-tert-butoxycarbonyl-(s)-fluorenylmethyl-L-cysteine are dissolved in dichloromethane, and treated with anhydrous toluene (2×20 ml), and water is azeotropically removed. Under argon protection, the mixture from which water has been removed is dissolved in 50 ml of dichloromethane, transferred to a 250 ml three-necked flask, and cooled to −10° C. or less; 0.262 g of DMAP (2.14 mmol) is added, and a solution of 1.64 g of 1-ethyl-(3-dimethylaminopropyl)carbodiimide hydrochloride (EDC hydrochloride) (8.57 mmol) in dichloromethane is dropwise added; after the dropwise addition is completed, the reaction is stirred at 10° C. to 15° C. for 2 hours, quenched by adding a saturated sodium bicarbonate aqueous solution and allowed for layering; the aqueous layer is extracted with dichloromethane (2×50 ml), and the organic layers are combined, dried over anhydrous sodium sulfate and concentrated in vacuo to obtain an oil, which is subjected to column chromatography (n-hexane:ethyl acetate=4:1 to 1:1) to obtain 3.7 g of the compound as a light yellow solid, with a yield of 89.6%.

$^1$HNMR (400MHZ, CDCl$_3$): δ7.73 (t, J=6.8 Hz, 4H), 7.63 (m, 2H), 7.54 (d, J=7.6 Hz, 2H), 7.40-7.34 (m, 4H), 7.31-7.27 (m, 4H), 6.62 (s, 2H), 5.86 (s, 1H), 5.81 (s, 1H), 5.75 (s, 1H), 5.72 (s, 1H), 5.70 (s, 1H), 5.35 (d, J=6.0 Hz, 1H), 5.22 (d, J=6.0 Hz, 1H), 5.13 (d, J=6.0 Hz, 1H), 4.97 (d, J=6.0, J=8.8 Hz, 1H), 4.43 (m, 2H), 4.20-4.01 (m, 8H), 3.97-3.85 (m, 4H), 3.54 (m, 2H), 3.38 (s, 3H), 3.35 (s, 3H), 3.34-2.91 (m, 8H), 2.60-2.31 (m, 4H), 2.27 (s, 3H), 2.25 (s, 3H), 2.21 (s, 3H), 1.97 (s, 3H), 1.94-1.81 (m, 2H), 1.77 (s, 3H), 1.43 (s, 9H), 1.41 (s, 9H);

MS: m/z (965.12.), Found: 966.25 (M+H)$^+$.

Example 8: Example 8 Synthesis of Compound 9

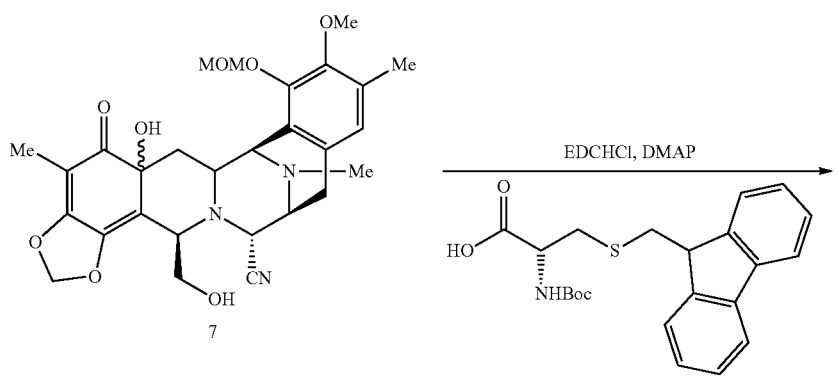

7

-continued

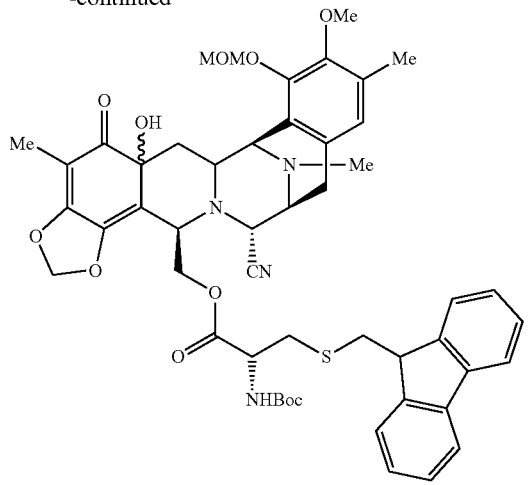

9

1.5 g of compound 7 and 1.67 g of N-tert-butoxycarbonyl-(s)-fluorenylmethyl-L-cysteine are dissolved in dichloromethane, and treated with anhydrous toluene (2×15 ml), and water is azeotropically removed. Under argon protection, the mixture from which water has been removed is dissolved in 30 ml of dichloromethane, transferred to a 100 ml three-necked flask, and cooled to −10° C. or less; 0.17 g of DMAP is added and a solution of 1.07 g of 1-ethyl-(3-dimethylaminopropyl)carbodiimide hydrochloride (EDC hydrochloride) (5.56 mmol) in dichloromethane is dropwise added; after the dropwise addition is completed, the reaction is stirred at 10° C. to 15° C. for 2 hours, quenched by adding a saturated sodium bicarbonate aqueous solution and allowed for layering; the aqueous layer is extracted with dichloromethane (2×30 ml), and the organic layers are combined, dried over anhydrous sodium sulfate and concentrated in vacuo to obtain an oil, which is subjected to column chromatography (n-hexane:ethyl acetate=4:1 to 1:1) to obtain 2.28 g of the compound as a light yellow solid, with a yield of 88.9%.

$^1$HNMR (400MHZ, CDC$_3$): δ7.73-7.61 (m, 4H), 7.63 (m, 2H), 7.37-7.30 (m, 4H), 6.62 (s, 1H), 6.59 (s, 1H), 6.53 (s, 1H), 5.72 (s, 1H), 5.70 (s, 1H), 5.61 (s, 1H), 5.55 (bs, 1H), 5.34 (m, 2H), 5.08 (m, 1H), 5.01 (m, 1H), 4.67 (m, 1H), 4.50 (m, 1H), 4.38 (dd, J1=4.8, J2=12.8, 1H), 4.21 (dd, J1=6.4, J2=12.8, 1H), 4.11 (m, 1H), 4.02 (m, 3H), 3.87 (m, 1H), 3.83 (s, 3H), 3.72 (m, 1H), 3.61 (s, 3H), 3.49 (s, 3H), 3.27 (m, 1H), 3.15 (dd, J1=1.6 Hz, J2=6.0 Hz, 2H), 3.07 (d, J=6.4 Hz, 1H), 2.94 (m, 4H), 2.86 (m, 2H), 2.42 (m, 2H), 2.25 (s, 3H), 2.20 (s, 3H), 2.15 (s, 3H), 2.08 (dd, J1=2.4 Hz, J2 =13.2 Hz, 1H), 1.77 (s, 3H), 1.76 (s, 3H), 1.43 (s, 9H);

MS: m/z (921.06.), Found: 922.35 (M+H)$^+$.

Example 9: Example 9 Synthesis of Compound 10

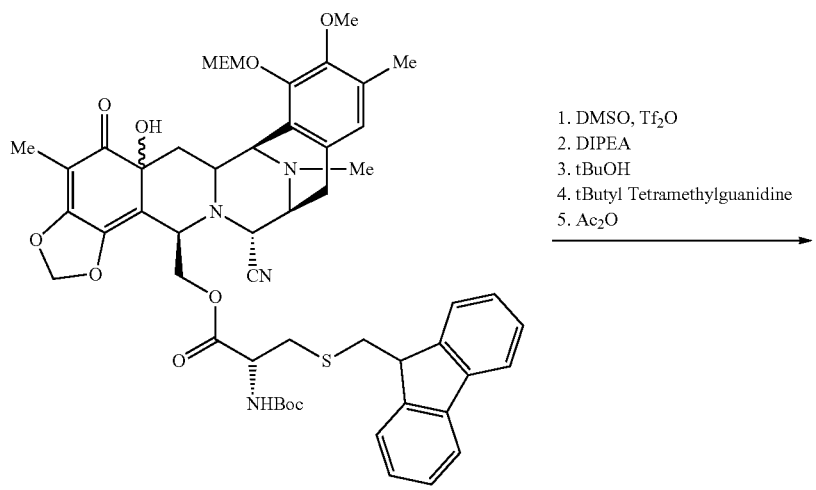

8

1. DMSO, Tf$_2$O
2. DIPEA
3. tBuOH
4. tButyl Tetramethylguanidine
5. Ac$_2$O
→

-continued

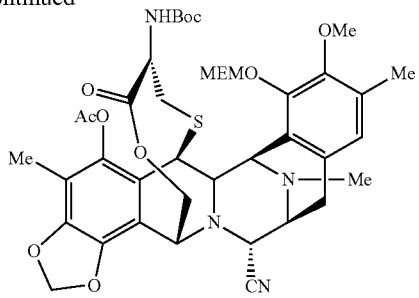

10

Under argon protection, to a 500 ml three-necked flask, 4.1 g of dimethyl sulfoxide and 300 ml of anhydrous dichloromethane are added, and 3.5 g of trifluoromethanesulfonic anhydride is dropwise added at −70° C. to −80° C.; after the dropwise addition is completed, the reaction is stirred for 20 minutes with the temperature being maintained constant, and a solution of 10.0 g of compound 8 in dichloromethane is dropwise added, with the internal temperature being controlled to not exceed −70° C. during the dropwise addition; after the dropwise addition is completed, the temperature is raised to −45° C. to −40° C. for 1 h of reaction, and 13.40 g of diisopropylethylamine is dropwise added; after the dropwise addition is completed, the temperature is slowly returned to 0° C. and then reduced to −15° C. or less and 3.45 g of tert-butanol (46.55 mmol) is dropwise added; the mixture is stirred for 10 minutes and a solution of 17.8 g of 2-tert-butyl-1,1,3,3-tetramethylguanidine in dichloromethane is dropwise added; the temperature is slowly raised to 0° C. and then reduced to −10° C. or less, 13.22 g of acetic anhydride is slowly dropwise added; and after the dropwise addition is completed, a reaction is carried out for 15 minutes with the temperature being maintained constant, quenched by adding a saturated ammonium chloride aqueous solution and allowed for layering, and the aqueous layer is extracted with 250 ml of dichloromethane. The organic layers are combined, washed with a saturated sodium bicarbonate aqueous solution and a saturated sodium chloride aqueous solution respectively, concentrated and subjected to column chromatography (n-hexane:ethyl acetate=5:1 to 1:1) to obtain an off-white foamy solid, which is recrystallized from ethyl acetate and n-hexane to obtain 6.26 g of the compound as a white powdery solid, with a yield of 74.5% and HPLC >96%.

$^1$HNMR (400MHZ, CDCl$_3$): δ6.78 (s, 1H), 6.09 (d, J=1.2 Hz, 1H), 5.99 (d, J=1.2 Hz, 1H), 5.33 (d, J=6.0 Hz, 1H), 5.20 (d, J=5.6 Hz, 1H), 5.03 (d, J=11.6 Hz, 1H), 4.64 (d, J=9.6 Hz, 1H), 4.51 (bs, 1H), 4.35 (d, J=4.8 Hz, 1H), 4.29-4.12 (m, 4H), 3.920 (m, 2H), 3.76 (s, 3H), 3.59-3.57 (t, J=4.8 Hz, 2H), 3.43-3.39 (m, 2H), 3.37 (s, 3H), 2.92-2.90 (m, 2H), 2.31-2.04 (m, 2H), 2.28 (s, 3H), 2.21 (s, 3H), 2.08 (s, 3H), 2.03 (s, 3H), 1.45 (s, 9H);

MS: m/z (810.91), Found: 811.60 (M+H)$^+$.

Example 10: Example 10 Synthesis of Compound 11

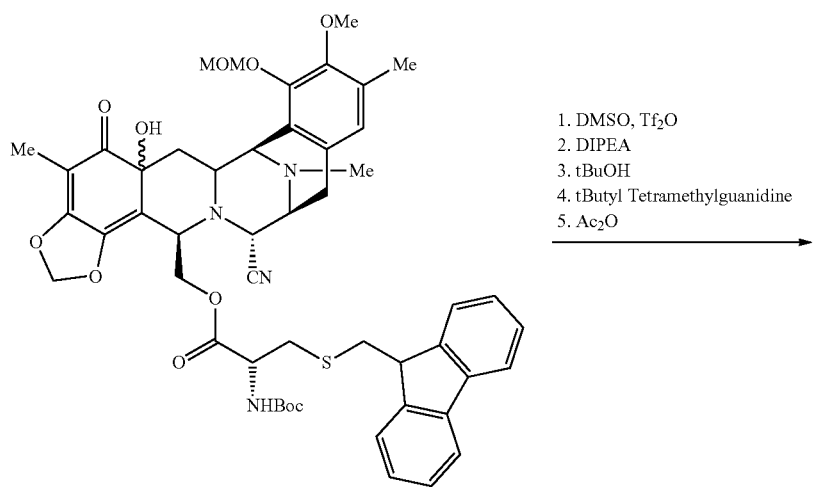

1. DMSO, Tf$_2$O
2. DIPEA
3. tBuOH
4. tButyl Tetramethylguanidine
5. Ac$_2$O

9

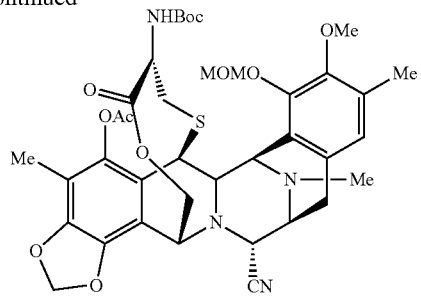

11

With reference to a similar method to example 9, the compound is prepared and obtained as a white powdery solid, with a yield of 72.7% and HPLC >96%.

¹HNMR (400MHZ, CDCl₃): δ6.78 (s, 1H), 6.09 (d, J=1.2 Hz, 1H), 5.99 (d, J=1.2 Hz, 1H), 5.20 (d, J=5.6 Hz, 1H), 5.14 (d, J=5.6 Hz, 1H), 5.03 (d, J=11.6 Hz, 1H), 4.64 (d, J=9.6 Hz, 1H), 4.51 (s, 1H), 4.33 (d, J=4.8 Hz, 1H), 4.29-4.17 (m, 4H), 3.76 (s, 3H), 3.57 (s, 3H), 3.42 (m, 2H), 2.93 (m, 2H), 2.35 (m, 1H), 2.31 (s, 3H), 2.28 (s, 3H), 2.21 (s, 3H), 2.09 (m, 1H), 2.05 (s, 3H), 1.45 (s, 9H); MS: m/z (766.86), Found: 767.50 (M+H)⁺.

Example 11: Example 11 Synthesis of Compound QT4A

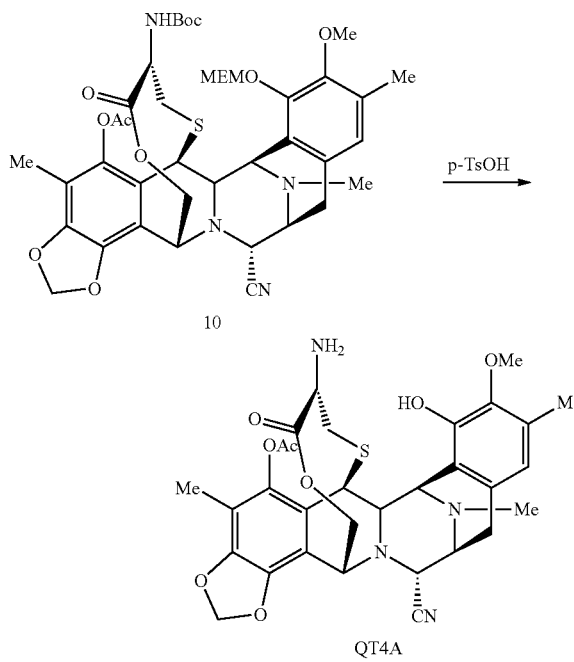

Under argon protection, to a 500 ml three-necked flask, 6.0 g of compound 10 and 300 ml of trichloromethane are added, and after the temperature is reduced to 0° C., 7.65 g of anhydrous p-toluenesulfonic acid is added; and after the addition is completed, the reaction is stirred for 44 hours with the temperature being maintained at 20° C. to 25° C. After the temperature is reduced to 10° C., the reaction is quenched by adding a saturated sodium bicarbonate aqueous solution, and the pH is adjusted to about 8; the resultant is allowed for layering; the aqueous layer is extracted with dichloromethane (2×50 ml), and the organic layers are combined, concentrated and subjected to column chromatography (n-hexane:ethyl acetate=2:1 to 1:2) followed by recrystallization from ethyl acetate and n-hexane to obtain 4.37 g of the compound as a white solid, with a yield of 94.9% and HPLC >96%.

¹HNMR (400MHZ, CDCl₃): δ6.52 (s, 1H), 6.07 (d, J=1.2 Hz, 1H), 5.99 (d, J=1.2 Hz, 1H), 5.73 (bs, 1H), 5.02 (d, J=11.6 Hz, 1H), 4.54 (bs, 1H), 4.25 (d, J=3.2 Hz, 2H), 4.18 (d, J=2.8 Hz, 1H), 4.14 (dd, J1=2.0 Hz, J2=11.6 Hz, 1H), 3.78 (s, 3H), 3.42-3.39 (m, 2H), 3.27 (t, J=6.8 Hz, 1H), 2.91 (m, 2H), 2.21-2.18 (m, 2H), 2.30 (s, 3H), 2.28 (s, 3H), 2.18 (s, 3H), 2.03 (s, 3H); MS: m/z (622.69), Found: 623.25 (M+H)⁺.

Example 12: Example 12 Synthesis of Compound QT4A

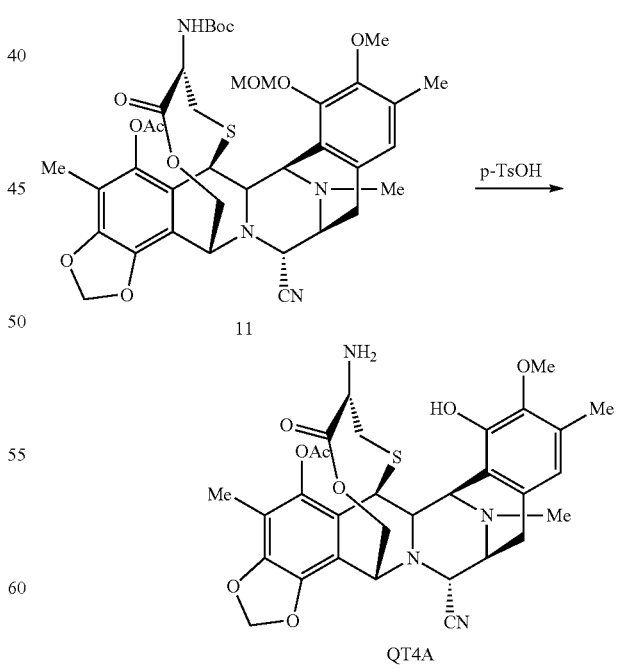

With reference to a similar method to example 11, compound QT4A is prepared from compound 11, with a yield of 94.8%. ¹HNMR (400MHZ, CDC₃): 56.52 (s, 1H), 6.07 (d, J=1.2 Hz, 1H), 5.99 (d, J=1.2 Hz, 1H), 5.73 (bs, 1H), 5.02 (d, J=11.6 Hz, 1H), 4.54 (bs, 1H), 4.25 (d, J=3.2 Hz, 2H), 4.18 (d, J=2.8 Hz, 1H), 4.14 (dd, J1=2.0 Hz, J2=11.6 Hz, 1H), 3.78 (s, 3H), 3.42-3.39 (m, 2H), 3.27 (t, J=6.8 Hz, 1H), 2.91 (m, 2H), 2.21-2.18 (m, 2H), 2.30 (s, 3H), 2.28 (s, 3H), 2.18 (s, 3H), 2.03 (s, 3H); MS: m/z (622.69), Found: 623.25 (M+H)$^+$.

Example 13: Example 13 Synthesis of Compound QT3A

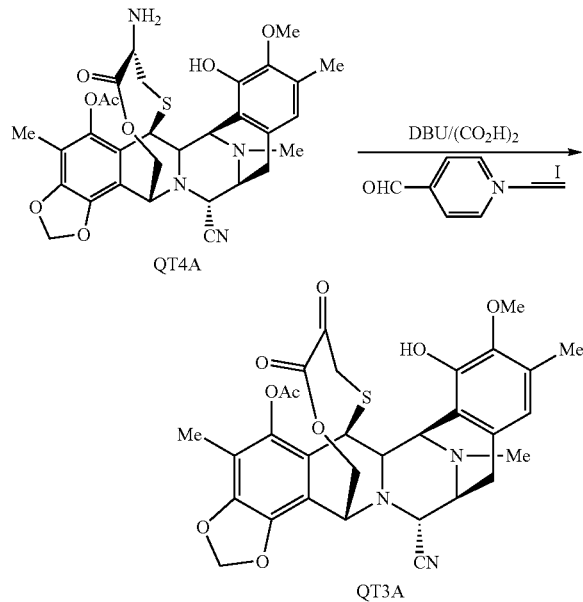

According to methods known in the art, such as a method disclosed in example 20 of WO 2001087895, QT3A is prepared from QT4A, with a yield of 64.1%.

$^1$HNMR (400MHZ, CDCl$_3$): δ6.49 (s, 1H), 6.11 (d, J=1.2 Hz, 1H), 6.02 (d, J=1.2 Hz, 1H), 5.70 (s, 1H), 5.10 (d, J=11.6 Hz, 1H), 4.66 (bs, 1H), 4.39 (s, 1H), 4.27 (d, J=4 Hz, 1H), 4.23 (dd, J1 =1.2 Hz, J2=11.2 Hz, 1H), 4.16 (d, J=2.4 Hz, 1H), 3.75 (s, 3H), 3.55 (d, J=5.2 Hz, 1H), 3.43 (d, J=8.8 Hz, 1H), 2.93-2.82 (m, 2H), 2.72 (d, J=17.6 Hz, 1H), 2.58 (dd, J=10.0 Hz, 1H), 2.32 (s, 3H), 2.24 (s, 3H), 2.14 (s, 3H), 2.04 (s, 3H);

MS: m/z (621.66), Found: 622.30 (M+1).

Example 14: Example 14 Synthesis of Compound ET770

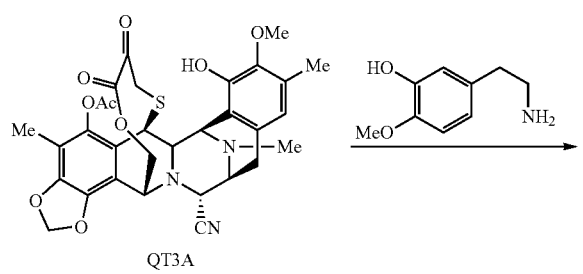

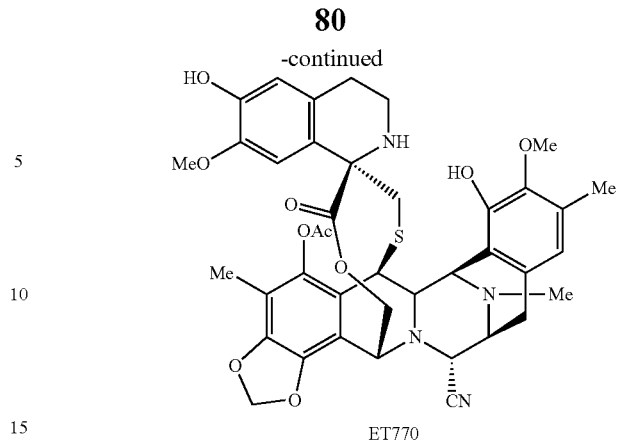

With reference to methods known in the art, such as a method disclosed in example 21 of WO 2001087895, ET770 is prepared from QT3A, with a yield of 93% and HPLC >99%.

$^1$HNMR (400MHZ, CDC$_3$): δ6.59 (s, 1H), 6.47 (s, 1H), 6.44 (s, 1H), 6.05 (d, J=1.2 Hz, 1H), 5.98 (d, J=1.2 Hz, 1H), 5.75 (s, 1H), 5.44 (bs, 1H), 5.03 (d, J=11.6 Hz, 1H), 4.57 (bs, 1H), 4.32 (s, 1H), 4.28 (d, J=4.8 Hz, 1H), 4.18 (d, J=2.8 Hz, 1H), 4.13 (dd, J1=2.0 Hz, J2=11.6 Hz, 1H), 3.79 (s, 3H), 3.62 (s, 3H), 3.51 (d, J=5.2 Hz, 1H), 3.42 (m, 1H), 3.12 (m, 1H), 2.95 (m, 2H), 2.79 (m, 1H), 2.60 (m, 1H), 2.49 (m, 1H), 2.36-2.11 (m, 2H), 2.32 (s, 3H), 2.26 (s, 3H), 2.19 (s, 3H), 2.04 (s, 3H); MS: m/z (770.85), Found: 771.50 (M+H)$^+$.

Example 15: Example 15 Synthesis of Compound ET743

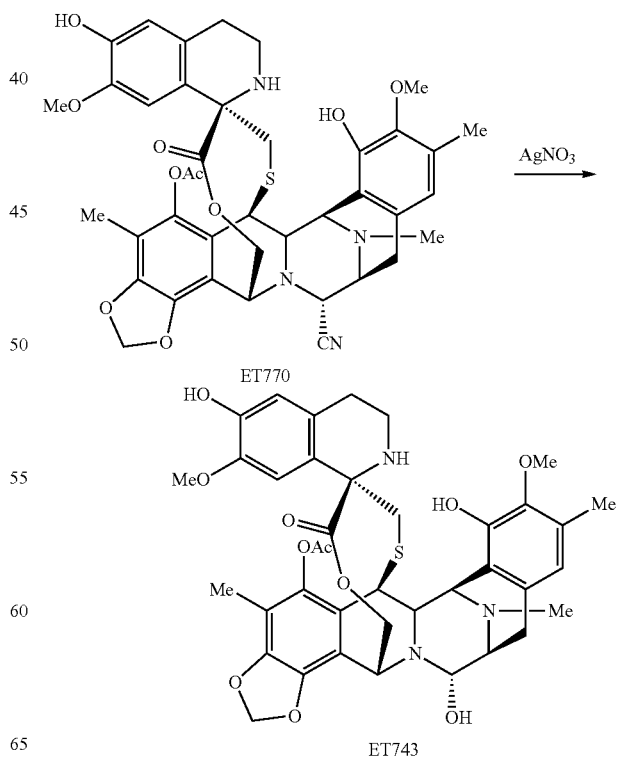

Under argon protection, to a 250 ml three-necked flask, 2.5 g of compound ET770, 11.02 g of silver nitrate, 50 ml of acetonitrile and 37.5 ml of deionized water are added, and the mixture is stirred at 20° C. to 25° C. for 2 hours away from light and filtered over diatomaceous earth; the filtrate is added to a mixed solution of 200 ml of a saturated sodium bicarbonate aqueous solution and 100 ml of a saturated sodium chloride aqueous solution; after a large amount of white solid sufficiently precipitates out, the mixture is filtered over diatomaceous earth, and the filter cake is washed with dichloromethane; after layering, the aqueous layer is extracted with dichloromethane (3×100 ml), and the organic layers are combined, washed sequentially with a saturated sodium chloride aqueous solution, an ammonium chloride-aqueous ammonia buffer (pH 8-9) and a saturated sodium chloride aqueous solution, dried over anhydrous sodium sulfate, concentrated under reduced pressure, and recrystallized from dichloromethane and n-pentane to obtain 2.35 g of the compound as a white crystalline powder, with a yield of 95.1% and HPLC >99%.

¹HNMR (400MHZ, CDCl₃): δ6.60 (s, 1H), 6.46 (s, 1H), 6.45 (s, 1H), 6.02 (d, J=0.8 Hz, 1H), 5.94 (d, J=0.8 Hz, 1H), 5.69 (s, 1H), 5.41 (bs, 1H), 5.14 (d, J=10.8 Hz, 1H), 4.81 (s, 1H), 4.47 (bs, 1H), 4.41 (bs, 1H), 4.16 (d, J=4.0 Hz, 1H), 4.05 (dd, J1=2.0 Hz, J2=11.2 Hz, 1H), 3.79 (s, 3H), 3.61 (s, 3H), 3.58 (d, J=4.8 Hz, 1H), 3.22 (m, 1H), 3.13 (m, 1H), 2.88-2.77 (m, 3H), 2.60 (m, 1H), 2.50 (m, 1H), 2.37-2.13 (m, 2H), 2.32 (s, 3H), 2.26 (s, 3H), 2.17 (s, 3H), 2.04 (s, 3H); MS: m/z (761.84), Found: 762.25 (M+H)⁺.

Example 16: Example 16 Synthesis of Compound 12

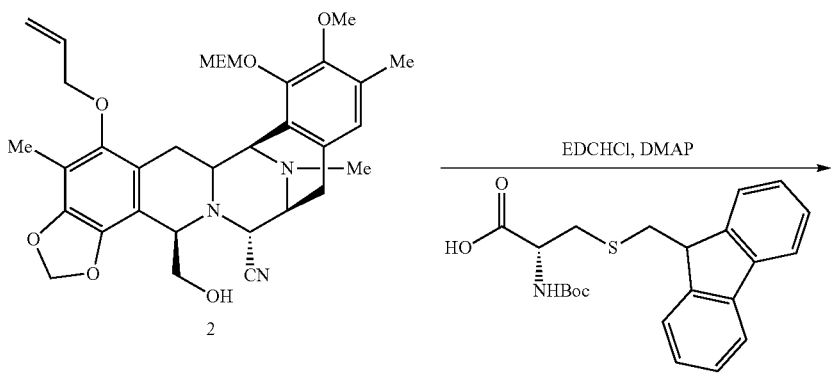

2

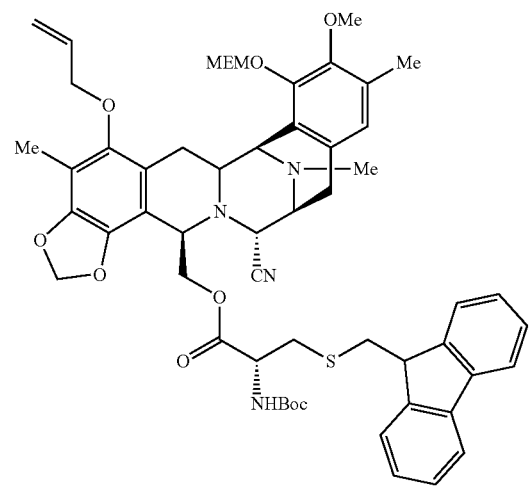

12

5.0 g of compound 2 and 4.93 g of N-tert-butoxycarbonyl-(s)-fluorenylmethyl-L-cysteine are dissolved in dichloromethane, and treated with anhydrous toluene (2×50 ml), and water is azeotropically removed. Under argon protection, the mixture from which water has been removed is dissolved in 100 ml of dichloromethane, transferred to a 250 ml three-necked flask, and cooled to −10° C. or less; 0.502 g of DMAP is added, and a solution of 3.15 g of 1-ethyl-(3-dimethylaminopropyl)carbodiimide hydrochloride (EDC hydrochloride) in dichloromethane is dropwise added; after the dropwise addition is completed, the reaction is stirred at 10° C. to 15° C. for 2 hours, quenched by adding a saturated sodium bicarbonate aqueous solution and allowed for layering; the aqueous layer is extracted with dichloromethane (2×100 ml), and the organic layers are combined, dried over anhydrous sodium sulfate and concentrated in vacuo to obtain an oil, which is subjected to column chromatography (n-hexane:ethyl acetate=4:1 to 2:1) to obtain 7.90 g of the compound as a white foamy solid, with a yield of 97.1% and HPLC >96%.

$^1$HNMR (400MHZ, CDCl$_3$): δ7.73-7.70 (m, 2H), 7.61 (dd, J1=7.6 Hz, J2=15.6 Hz, 2H), 7.37 (m, 2H), 7.29-7.26 (m, 2H), 6.62 (s, 1H), 6.08-5.99 (m, 1H), 5.91 (d, J=1.2 Hz, 1H), 5.80 (d, J=1.2 Hz, 1H), 5.37 (dd, J1=1.6, J2=17.2 Hz), 5.24 (d, J=6.0 Hz, 1H), 5.14 (d, J=6.0 Hz), 5.04 (brd, J =8.8 Hz, 1H), 4.28 (m, 2H), 4.17-3.92 (m, 8H), 3.85 (m, 1H), 3.69 (s, 3H), 3.57 (m, 2H), 3.38 (s, 3H), 3.37-3.16 (m, 3H), 2.98-2.93 (m, 3H), 2.61 (m, 2H), 2.29 (s, 3H), 2.20 (s, 3H), 2.03 (s, 3H), 1.75 (dd, J1=11.6, J2=15.6 Hz, 1H), 1.44 (s, 9H);

[0163] MS: m/z (989.18), Found: 990.0 (M+H)$^+$.

Example 17: Example 17 Synthesis of Compound 13

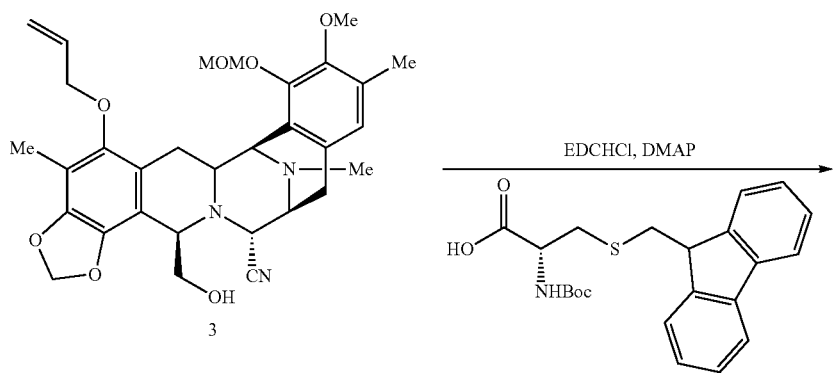

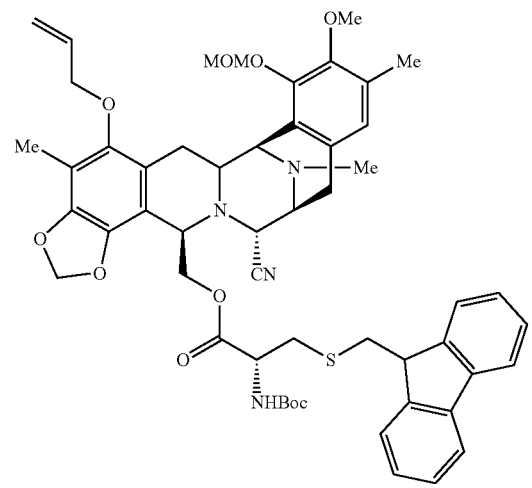

13

With reference to a similar method to example 16, compound 13 is prepared and obtained as a white foamy solid, with a yield of 97.4% and HPLC >95%.

MS: m/z (945.13), Found: 946.50 (M+H)+.

Example 18: Example 18 Synthesis of Compound 14

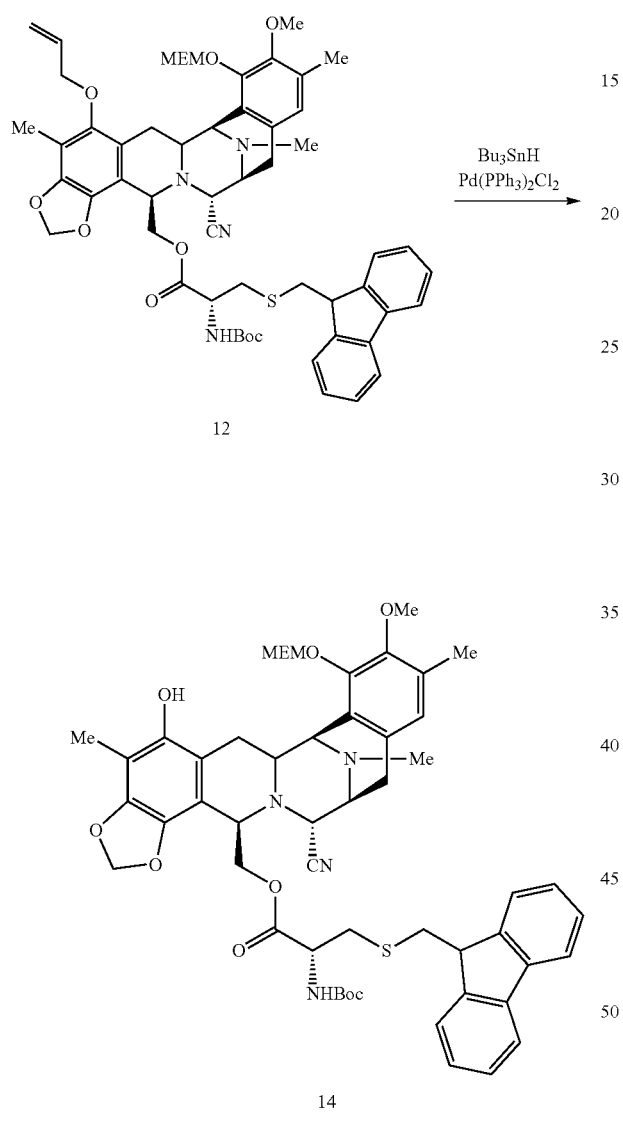

Under argon protection, to a 250 ml three-necked flask, 7.5 g of compound 12, 0.37 g of bis(triphenylphosphine) palladium dichloride, 2.28 g of acetic acid and 150 ml of dichloromethane are added, and 5.50 g of tri-n-butyl tin hydride is added at −15° C. to −10° C.; after the addition is completed, with the temperature being maintained at 0° C. to 5° C., the reaction is stirred for 1 hour, quenched by adding a saturated potassium fluoride aqueous solution and extracted with dichloromethane (2×100 ml); and the organic layers are combined, dried over anhydrous sodium sulfate and concentrated in vacuo to obtain an oil, which is subjected to column chromatography (n-hexane:ethyl acetate=4:1 to 1:1) to obtain 7.0 g of the compound as a white foamy solid, with a yield of 97.3% and HPLC >96%. MS: m/z (949.12), Found: 950.0 (M+H)+.

With reference to a similar method to example 18, compound 40 is prepared from compound 38, and compound 41 is prepared from compound 39.

With reference to a similar method to example 18, compound 33 is prepared from compound 31 and obtained as a white foamy solid, with a yield of 95.2%. MS: m/z (939.08), Found: 940.0 (M+H)+.

Example 19: Example 19 Synthesis of Compound 15

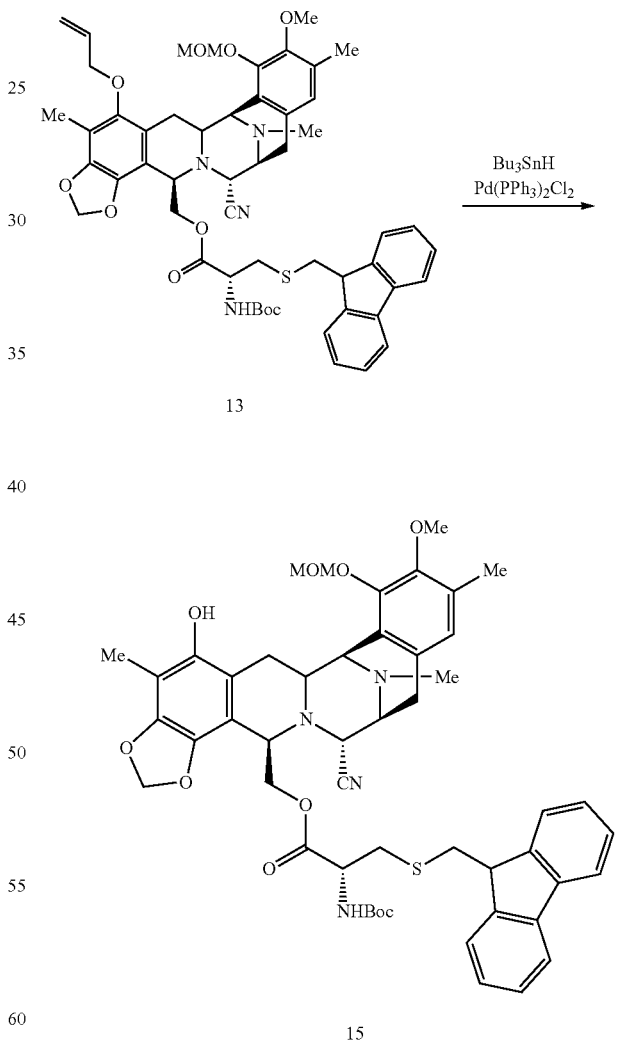

With reference to a method of example 19, compound 15 is prepared and obtained as a white foamy solid, with a yield of 96.1%.

MS: m/z (905.07), Found: 906.35 (M+H)+.

Example 20: Example 20 Synthesis of Compound 8

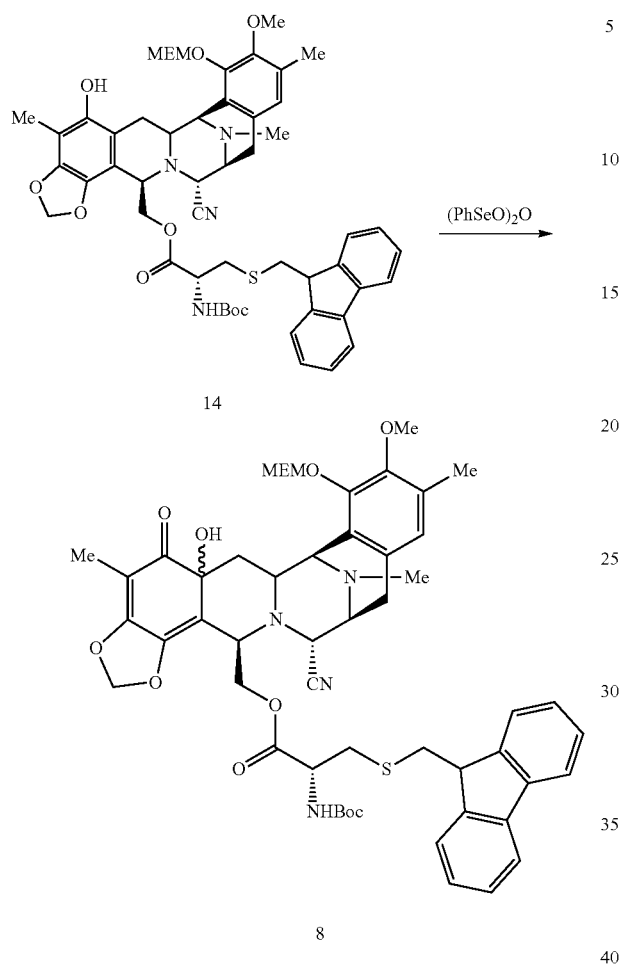

Under argon protection, to a 500 ml three-necked flask, 6.0 g of compound 14 (6.32 mmol) and 120 ml of dichloromethane are added; after the temperature is reduced to −40° C. to −35° C., a solution of 2.28 g of benzeneseleninic anhydride (6.33 mmol) in dichloromethane is added; with the temperature being raised to −20° C. to −15° C., the reaction is stirred for 1 hour, quenched by adding a saturated sodium bicarbonate aqueous solution and allowed for layering; the aqueous layer is extracted with dichloromethane (2×100 ml), and the organic layers are combined, dried over anhydrous sodium sulfate and concentrated in vacuo to obtain an oil, which is subjected to column chromatography (n-hexane:ethyl acetate=4:1 to 1:1) to obtain 5.9 g of the compound as a light yellow solid, with a yield of 96.7% and HPLC >96%.

$^1$HNMR (400MHZ, CDCl$_3$): δ7.73 (t, J=6.8 Hz, 4H), 7.63 (m, 2H), 7.54 (d, J=7.6 Hz, 2H), 7.40-7.34 (m, 4H), 7.31-7.27 (m, 4H), 6.62 (s, 2H), 5.86 (s, 1H), 5.81 (s, 1H), 5.75 (s, 1H), 5.72 (s, 1H), 5.70 (s, 1H), 5.35 (d, J=6.0 Hz, 1H), 5.22 (d, J=6.0 Hz, 1H), 5.13 (d, J=6.0 Hz, 1H), 4.97 (d, J=6.0, J=8.8 Hz, 1H), 4.43 (m, 2H), 4.20-4.01 (m, 8H), 3.97-3.85 (m, 4H), 3.54 (m, 2H), 3.38 (s, 3H), 3.35 (s, 3H), 3.34-2.91 (m, 8H), 2.60-2.31 (m, 4H), 2.27 (s, 3H), 2.25 (s, 3H), 2.21 (s, 3H), 1.97 (s, 3H), 1.94-1.81 (m, 2H), 1.77 (s, 3H), 1.43 (s, 9H), 1.41 (s, 9H);

MS: m/z (965.12), Found: 966.25 (M+H)$^+$.

With reference to a similar method, compound 34 is prepared from compound 40; and compound 35 is prepared from compound 41.

With reference to a similar method to example 20, compound 26 is prepared from compound 32 and obtained as a light yellow solid, with a yield of 95.6%. MS: m/z (999.13), Found: 1000.05 (M+H)$^+$.

With reference to a similar method to example 20, compound 27 is prepared from compound 33 and obtained as a light yellow solid, with a yield of 96.9%. MS: m/z (955.08.), Found: 956.0 (M+H)$^+$.

Example 21: Example 21 Synthesis of Compound 9

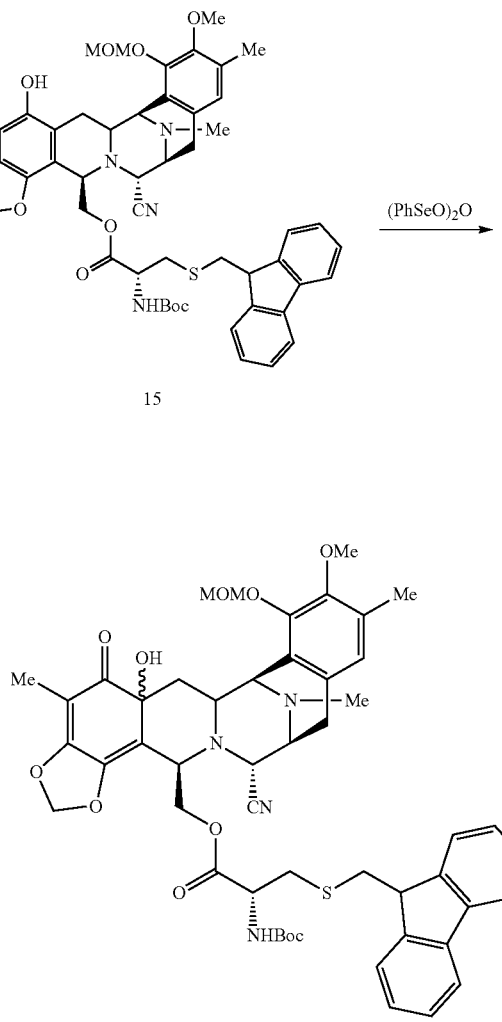

With reference to a similar method to example 20, compound 9 is prepared and obtained as a light yellow solid, with a yield of 98.3% and HPLC >98%.

MS: m/z (921.06.), Found: 922.35 (M+H)$^+$.

Example 22: Example 22 Synthesis of Compound 16

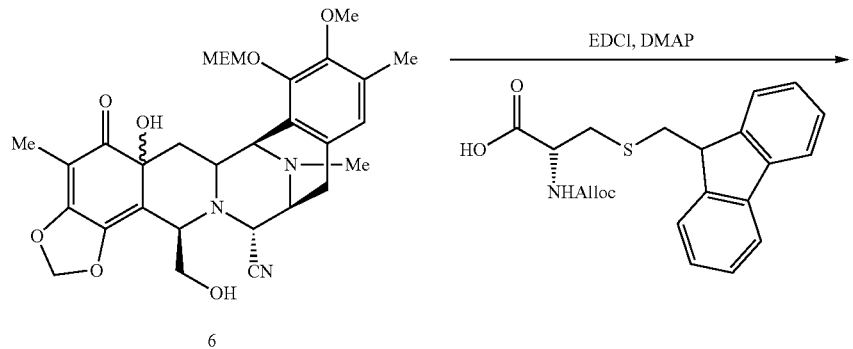

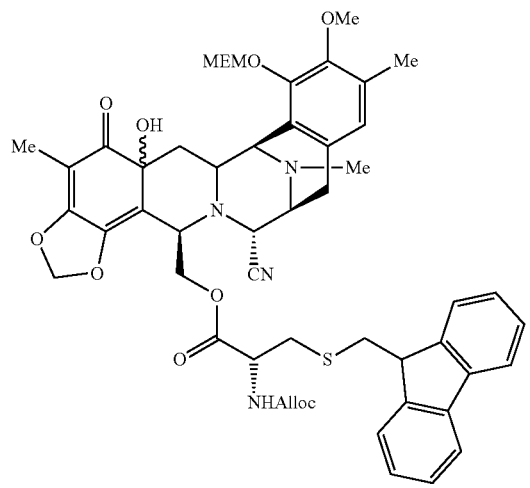

16

2.5 g of compound 6 (4.28 mmol) and 2.47 g of N-(allyloxycarbonyl)-S-(fluorenylmethyl)-L-cysteine (6.44 mmol) are dissolved in dichloromethane, and treated with anhydrous toluene (2×20 ml), and water is azeotropically removed. Under argon protection, the mixture from which water has been removed is dissolved in 50 ml of dichloromethane, transferred to a 250 ml three-necked flask, and cooled to −10° C. or less; 0.262 g of DMAP (2.14 mmol) is added, and a solution of 1.64 g of 1-ethyl-(3-dimethylaminopropyl)carbodiimide hydrochloride (EDC hydrochloride) (8.57 mmol) in dichloromethane is dropwise added; after the dropwise addition is completed, the reaction is stirred at 10° C. to 15° C. for 2 hours, quenched by adding a saturated sodium bicarbonate aqueous solution and allowed for layering; the aqueous layer is extracted with dichloromethane (2×50 ml), and the organic layers are combined, dried over anhydrous sodium sulfate, and concentrated in vacuo to obtain an oil, which is subjected to column chromatography (n-hexane:ethyl acetate=4:1 to 1:1) to obtain 3.6 g of the compound as a light yellow solid, with a yield of 88.6%, wherein compound 16 is a mixture of two isomers.

$^1$HNMR (400MHZ, CDCl$_3$): δ7.74 (m, 4H), 7.63 (m, 4H), 7.38 (m, 4H), 7.29 (m, 4H), 6.61 (s, 1H), 6.54 (s, 1H), 5.89 (m, 2H), 5.72 (s, 1H), 5.70 (s, 1H), 5.69 (s, 1H), 5.62 (s, 1H), 5.55 (m, 1H), 5.32 (d, J=15.2 Hz, 1H), 5.23 (d, J=6.0 Hz, 1H), 5.22 (d, J=10.4, 1H), 5.14 (d, J=6.0 Hz, 1H), 5.13 (d, J=6.0 Hz, 1H), 5.07 (d, J=6.4 Hz, 1H), 4.67 (m, 1H), 4.56 (m, 4H), 4.51 (m, 1H), 4.38 (dd, J1=4.4, J2=12.8, 1H), 4.22 (dd, J1=6.0 Hz, J2=11.2 Hz, 1H), 4.14-3.88 (m, 12H), 3.83 (s, 3H), 3.79-3.69 (m, 4H), 3.61 (s, 3H), 3.56 (m, 4H), 3.39 (s, 3H), 3.36 (s, 3H), 3.23 (m, 2H), 3.15 (dd, J=6.0 Hz, 2H), 3.07 (d, J=6.0 Hz, 2H), 3.00-2.81 (m, 6H), 2.46-2.34 (m, 4H), 2.25 (s, 3H), 2.20 (s, 3H), 2.15 (s, 3H), 2.08 (m, 1H), 1.83 (dd, J1=9.6 Hz, J2=15.2 Hz, 1H), 1.78 (s, 3H), 1.77 (s, 3H);

MS: m/z (949.07), Found: 950.0 (M+H)$^+$.

Example 23: Example 23 Synthesis of Compound 17

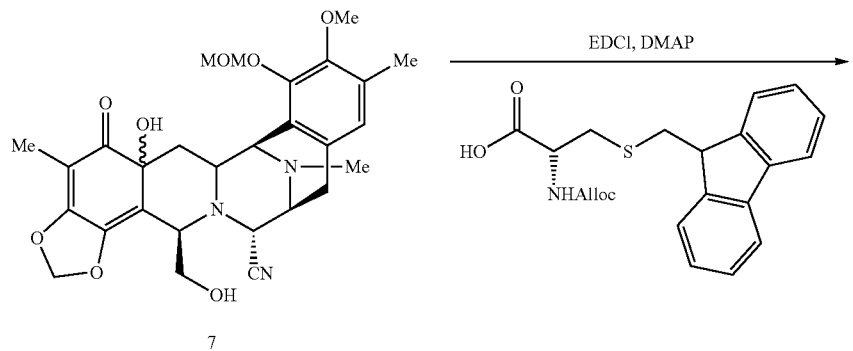

7

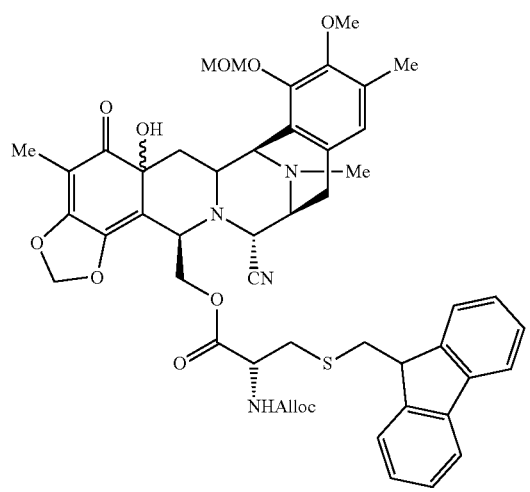

17

With reference to a similar method to example 22, compound 17 is prepared and obtained as a light yellow solid, with a yield of 87.4%.

$^1$HNMR (400MHZ, CDCl$_3$): δ7.75 (m, 2H), 7.62 (m, 2H), 7.40 (m, 2H), 7.30 (m, 2H), 6.63 (s, 11H), 5.89 (m, 11H), 5.74 (s, 11H), 5.71 (s, 11H), 5.52 (d, J=8.4 Hz, 11H), 5.32 (d, J=16.8 Hz, 1H), 5.22 (d, J=10.0 Hz, 1H), 5.10 (m, 2H), 4.57 (m, 2H), 4.50 (m, 1H), 4.23 (dd, J1=6.0 Hz, J2=11.2 Hz, 1H), 4.04 (m, 1H), 4.00 (dd, J1=2.4 Hz, J2=13.2 Hz, 1H), 3.93 (m, 1H), 3.84 (s, 3H), 3.49 (s, 3H), 3.24 (m, 1H), 3.08 (m, 3H), 2.95 (m, 3H), 2.44 (d, J=18.0 Hz, 1H), 2.36 (dd, J1=5.6 Hz, J2=15.2 Hz, 1H), 2.25 (s, 3H), 2.20 (s, 3H), 1.83 (dd, J1=9.6 Hz, J2=15.2 Hz, 1H), 1.78 (s, 3H); MS: m/z (905.02.), Found: 906.0 (M+H)$^+$.

Example 24: Example 24 Synthesis of Compound 18

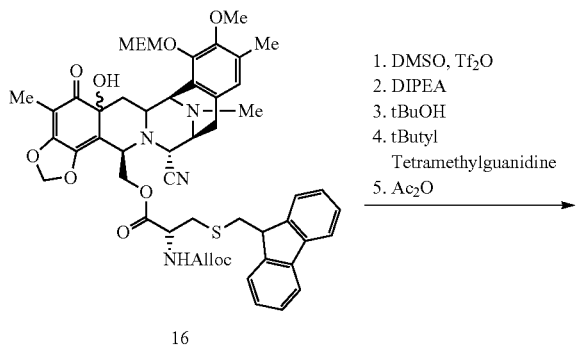

16

1. DMSO, Tf$_2$O
2. DIPEA
3. tBuOH
4. tButyl Tetramethylguanidine
5. Ac$_2$O

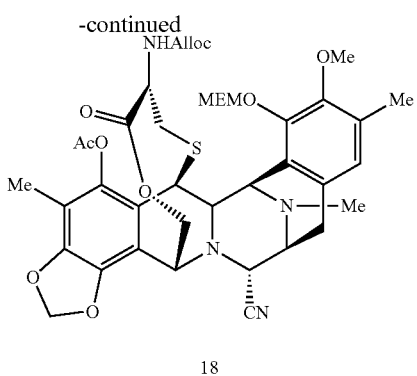

18

Under argon protection, to a 250 ml three-necked flask, 1.32 g of dimethyl sulfoxide (16.89 mmol) and 100 ml of anhydrous dichloromethane are added, and 1.24 g of trifluoromethanesulfonic anhydride (4.40 mmol) is dropwise added at −70° C. to −80° C.; after the dropwise addition is completed, the reaction is stirred for 20 minutes with the temperature being maintained constant, and a solution of 3.2 g of compound 16 (3.37 mmol) in dichloromethane is dropwise added, with the internal temperature being controlled to not exceed −70° C. during the dropwise addition; after the dropwise addition is completed, the temperature is raised to −45° C. to −40° C. for 50 minutes of reaction, and 4.36 g of diisopropylethylamine (33.73 mmol) is then dropwise added; after the dropwise addition is completed, the temperature is slowly raised to 0° C. and then reduced to −15° C. or less, and 1.12 g of tert-butanol (15.11 mmol) is dropwise added; the mixture is stirred for 10 minutes with the temperature being maintained constant, and a solution of 5.78 g of 2-tert-butyl-1,1,3,3-tetramethylguanidine (33.74 mmol) in dichloromethane is dropwise added; the temperature is slowly raised to 0° C. and then reduced to −10° C. or less, 4.30 g of acetic anhydride (42.54 mmol) is slowly dropwise added; and after the dropwise addition is completed, a reaction is carried out for 15 minutes with the temperature being maintained constant, quenched by adding a saturated ammonium chloride aqueous solution and allowed for layering, and the aqueous layer is extracted with 100 ml of dichloromethane. The organic layers are combined, washed with a saturated sodium bicarbonate aqueous solution and a saturated sodium chloride aqueous solution respectively, concentrated and subjected to column chromatography (n-hexane:ethyl acetate=5:1 to 1:1) to obtain 2.0 g of the compound as an off-white foamy solid, with a yield of 74.6% and HPLC >96%.

¹HNMR (400MHZ, CDCl₃): δ6.78 (s, 1H), 6.07 (d, J=1.2 Hz, 11H), 5.98 (d, J=1.2 Hz, 1H), 5.92 (m, 1H), 5.32 (d, J=6.0 Hz, 1H), 5.31 (dd, J1=1.5 Hz, J2=16.8 Hz, 1H), 5.23 (dd, J1=1.6 Hz, J2=10.4 Hz, 1H), 5.19 (d, J=5.6 Hz, 1H), 5.01 (d, J=11.6 Hz, 1H), 4.81 (d, J=9.6 Hz, 1H), 4.53-4.51 (m, 3H), 4.35-4.27 (m, 2H), 4.24 (s, 1H), 4.18-4.13 (m, 2H), 3.943.84 (m, 2H), 3.73 (s, 3H), 3.58 (t, J=4.8 Hz, 2H), 3.43-3.37 (m, 2H), 3.36 (s, 31H), 2.92 (m, 2H), 2.27 (s, 3H), 2.26 (s, 3H), 2.20 (s, 3H), 2.36-2.06 (m, 2H), 2.02 (s, 3H); MS: m/z (794.97), Found: 795.55 (M+H)⁺.

Example 25: Example 25 Synthesis of Compound 19

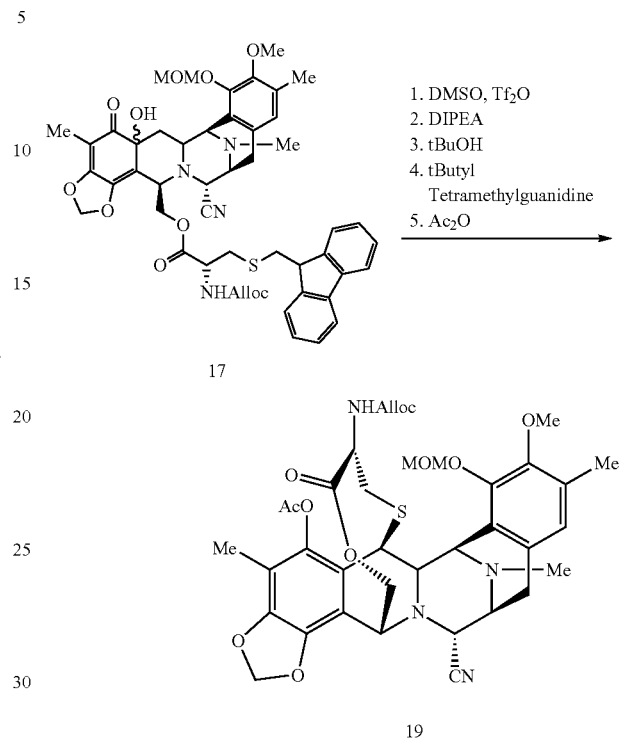

With reference to a similar method to example 24, compound 19 is prepared and obtained as an off-white foamy solid, with a yield of 74.3%.

¹HNMR (400MHZ, CDCl₃): δ 6.80 (s, 1H), 6.09 (d, J=1.2 Hz, 1H), 6.00 (d, J=1.2 Hz, 1H), 5.93 (m, 1H), 5.32 (dd, J1=1.2 Hz, J2=16.8 Hz, 1H), 5.23 (d, J=10.0 Hz, 1H), 5.22 (d, J=5.6 Hz, 1H), 5.14 (d, J=5.2 Hz, 1H), 5.03 (d, J=13.2 Hz, 1H), 4.83 (d, J=9.6 Hz, 1H), 4.52 (m, 3H), 4.31 (m, 2H), 4.24 (s, 1H), 4.16 (m, 2H), 3.74 (s, 3H), 3.56 (s, 3H), 3.45 (m, 1H), 3.40 (m, 1H), 2.92 (m, 1H), 2.29 (s, 3H), 2.28 (s, 3H), 2.22 (s, 3H), 2.13 (m, 1H), 2.03 (s, 31H); MS: m/z (750.81), Found: 751.50 (M+H)⁺.

Example 26: Example 26 Synthesis of Compound 20

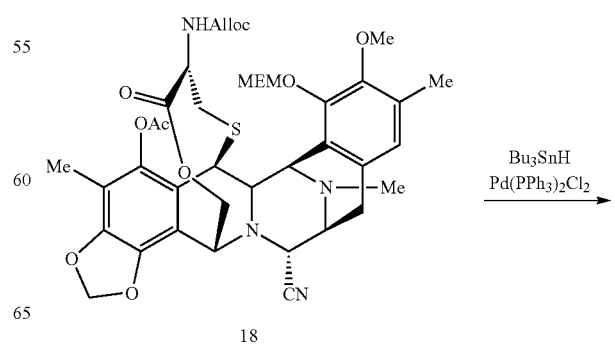

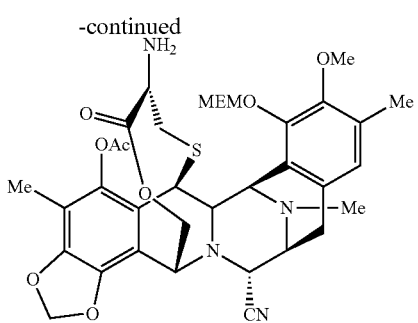

20

Under argon protection, to a 50 ml three-necked flask, 1.0 g of compound 18 (1.89 mmol), 0.14 g of bis(triphenylphosphine)palladium dichloride (0.20 mmol), 0.68 g of acetic acid (11.32 mmol) and 15 ml of dichloromethane are added, and 1.64 g of tri-n-butyl tin hydride (5.65 mmol) is added at −15° C. to −10° C.; after the addition is completed, with the temperature being maintained at 0° C. to 5° C., the reaction is stirred for 1 hour, quenched by adding a saturated potassium fluoride aqueous solution and extracted with dichloromethane (2×20 ml); and the organic layers are combined, dried over anhydrous sodium sulfate and concentrated in vacuo to obtain an oil, which is subjected to column chromatography (dichloromethane:methanol=50:1 to 10:1) to obtain 1.28 g of the compound as a white foamy solid, with a yield of 95.4% and HPLC >95%; MS: m/z (710.79), Found: 711.55 (M+H)⁺.

Example 27: Example 27 Synthesis of Compound 21

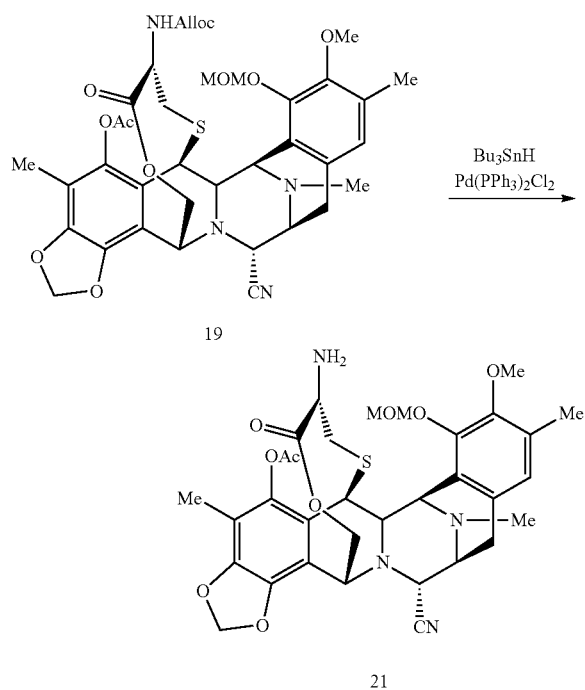

With reference to a similar method to example 26, compound 21 is prepared and obtained as a white solid, with a yield of 96.8% and HPLC >95%.

¹HNMR (400MHZ, CDCl₃): δ6.73 (s, 1H), 6.08 (d, J=1.2 Hz, 1H), 5.99 (d, J=1.2 Hz, 1H), 5.93 (m, 1H), 5.21 (d, J=3.6 Hz, 1H), 5.14 (d, J=3.6 Hz, 1H), 5.02 (d, J=12.0 Hz, 1H), 4.51 (m, 1H), 4.34 (d, J=4.8 Hz, 1H), 4.27 (s, 1H), 4.20 (d, J=3.2, 1H), 4.13 (d, J=12 Hz, 1H), 3.79 (s, 3H), 3.57 (s, 3H), 3.45 (d, J=4.8 Hz, 1H), 3.41 (m, 1H), 3.31 (m, 1H), 2.92 (m, 2H), 2.29 (s, 3H), 2.25 (s, 3H), 2.19 (s, 3H), 2.16 (m, 1H), 2.04 (s, 3H).

Example 28: Example 28 Synthesis of Compound 22

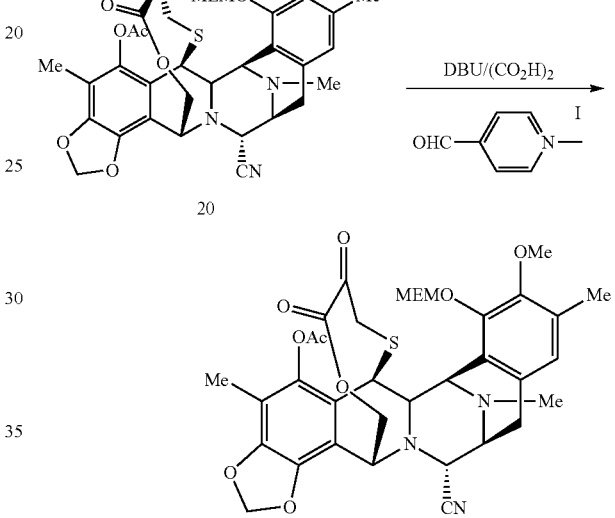

Under argon protection, 4.20 g of compound N-methylpyridine-4-carbaldehyde iodide (16.86 mmol), 40 ml of anhydrous DMF and 2 g of a molecular sieve are added to a 250 ml three-necked flask; the temperature is reduced to −5° C., and a solution of 1.2 g of compound 20 (1.69 mmol) in dichloromethane (60 ml) is dropwise added; after the dropwise addition is completed, the mixture is stirred for 5.5 hours with the temperature being maintained at 15° C. to 20° C. The temperature is reduced to −5° C., and 0.031 g of DBU (0.204 mmol) is added; and the mixture is stirred for 10 minutes, and 40 ml of a saturated oxalic acid aqueous solution is dropwise added; after the dropwise addition is completed, the mixture is stirred for 4 hours with the temperature being maintained at 15° C. to 20° C.; the temperature is reduced to 0° C., and 40 ml of a saturated potassium bicarbonate aqueous solution is added; the mixture is allowed for layering; the aqueous layer is extracted with dichloromethane (2×60 ml), and the organic layers are combined, concentrated and subjected to column chromatography (dichloromethane:methanol=50:1 to 10:1) to obtain a white solid, with a yield of 73.2% and HPLC >96%. MS: m/z (709.76), Found: 710.45 (M+H)⁺.

Example 29: Example 29 Synthesis of Compound 23

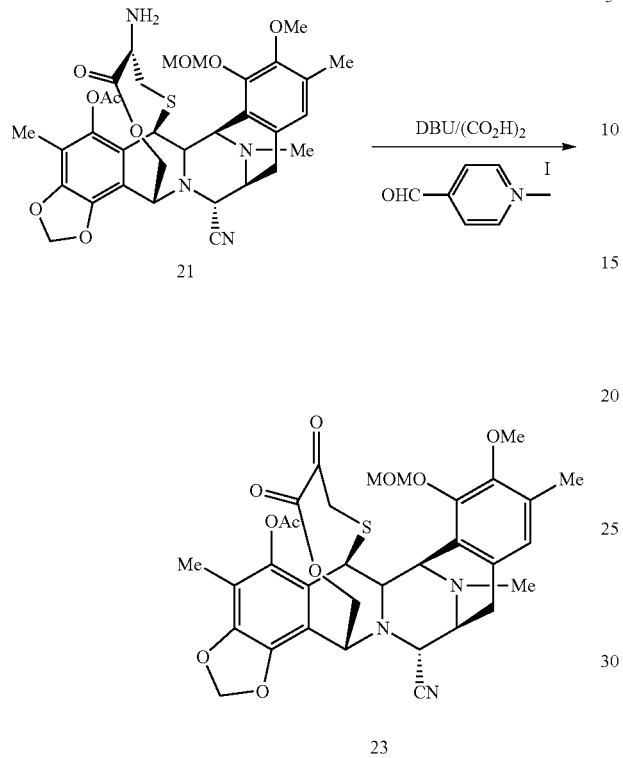

With reference to the method of example 28, compound 23 is prepared and obtained as a white solid, with a yield of 69.6% and HPLC >96%.

$^1$HNMR (400MHZ, CDCl$_3$): δ6.70 (s, 1H), 6.12 (d, J=1.6 Hz, 1H), 6.03 (d, J=1.6 Hz, 1H), 5.20 (d, J=5.6 Hz, 1H), 5.13 (d, J=5.6 Hz, 1H), 5.10 (d, J=12.0 Hz, 1H), 4.68 (m, 1H), 4.40 (s, 1H), 4.38 (dd, J1=2.0 Hz, J2=5.2 Hz, 1H), 4.22 (dd, J1=2.0 Hz, J2=10.8 Hz, 1H), 4.18 (d, J=2.8 Hz, 1H), 3.75 (s, 3H), 3.58 (m, 1H), 3.57 (s, 3H), 3.44 (m, 2H), 2.90 (m, 1H), 2.82 (d, J=13.2 Hz, 1H), 2.71 (d, J=17.2 Hz, 1H), 2.32 (s, 3H), 2.22 (s, 3H), 2.17 (m, 1H) 2.16 (s, 3H), 2.05 (s, 3H); MS: m/z (665.71), Found: 666.35 (M+H)$^+$.

Example 30: Example 30 Synthesis of Compound 24

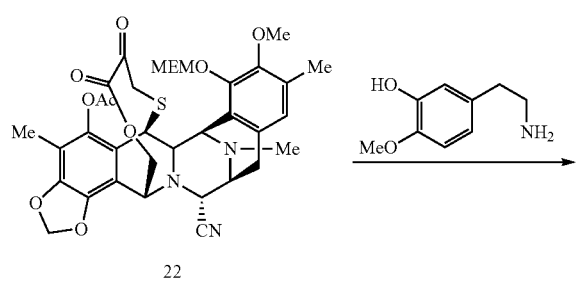

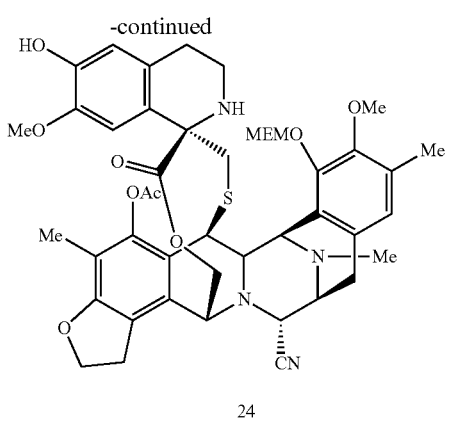

Under argon protection, 0.6 g of compound 22 (0.845 mmol), 2.0 g of silica gel (400 mesh), 0.57 g of 3-hydroxy-4-methoxyphenethylamine (3.41 mmol) and 30 ml of anhydrous ethanol are added to a 100 ml three-necked flask; the mixture is stirred at 20° C. to 25° C. for 18 hours, concentrated under reduced pressure to remove ethanol and subjected to column chromatography (dichloromethane:methanol=50:1 to 10:1) to obtain 0.67 g of compound as a white solid, with a yield of 92.5%.

MS: m/z (856.98), Found: 857.65 (M+H)$^+$.

Example 31: Example 31 Synthesis of Compound 25

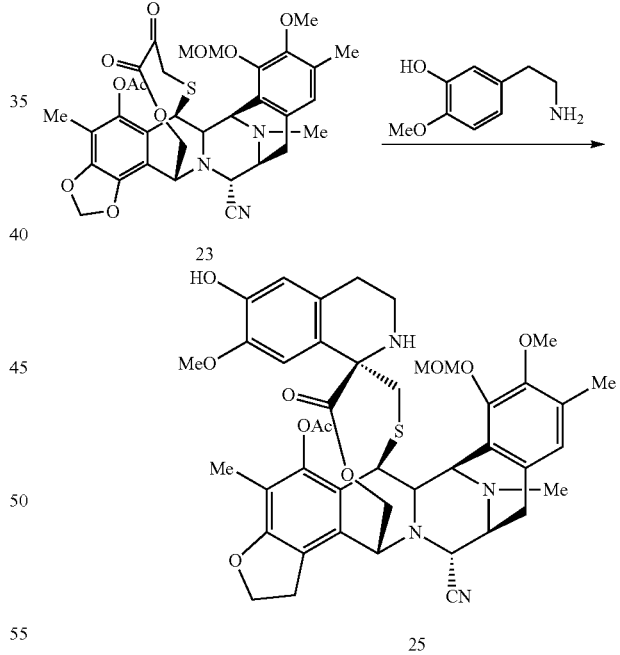

With reference to a similar method to example 30, compound 25 is prepared, with a yield of 91.4%.

$^1$HNMR (400MHZ, CDCl$_3$): δ6.86 (s, 1H), 6.52 (s, 1H), 6.51 (s, 1H), 6.12 (d, J=1.2 Hz, 1H), 6.06 (d, J=1.2 Hz, 1H), 5.26 (d, J=5.6 Hz, 1H), 5.22 (d, J=5.6 Hz, 1H), 5.06 (d, J=11.6 Hz, 1H), 4.62 (m, 1H), 4.42 (d, J=5.6 Hz, 1H), 4.36 (3, 1H), 4.25 (d, J=2.8 Hz, 1H), 4.19 (dd, J1=2.4 Hz, J2=11.2 Hz, 1H), 3.84 (s, 3H), 3.69 (s, 3H), 3.63 (s, 3H), 3.55 (m, 1H), 3.48 (m, 1H), 3.42 (m, 1H), 3.12 (m, 1H), 3.00 (m, 2H), 2.85 (m, 1H), 2.76 (dd, J1=6.8 Hz, J2=13.6 Hz, 1H), 2.62

(m, 2H), 2.45 (m, 2H), 2.34 (s, 31H), 2.31 (s, 3H), 2.25 (s, 3H), 2.09 (s, 3H); [0228] MS: m/z (812.93), Found: 813.70 (M+H)⁺.

Example 32: Example 32 Synthesis of Compound ET770

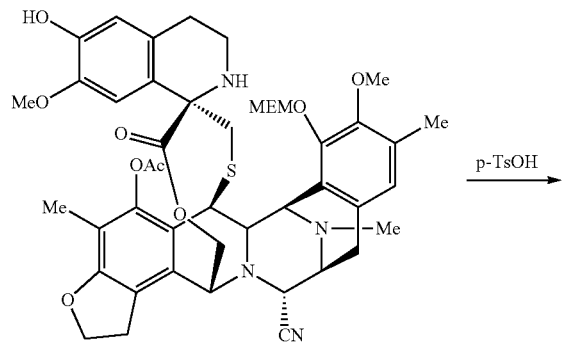

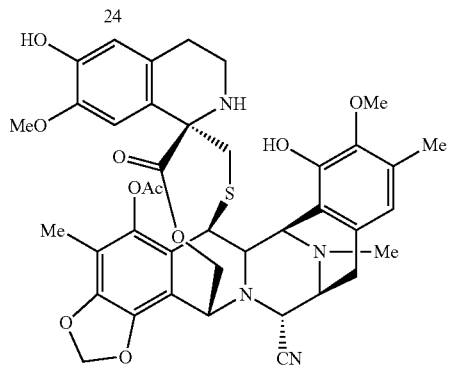

Under argon protection, to a 100 ml three-necked flask, 0.5 g of compound 24 and 25 ml of dichloromethane are added, and after the temperature is reduced to 0° C., 0.30 g of anhydrous p-toluenesulfonic acid is added; and after the addition is completed, the mixture is stirred for 12 hours with the temperature being maintained at 20° C. to 25° C. After the temperature is reduced to 10° C., the reaction is quenched by adding a saturated sodium bicarbonate aqueous solution, and the pH is adjusted to about 8; the resultant is allowed for layering; the aqueous layer is extracted with dichloromethane (2×20 ml), and the organic layers are combined, concentrated and subjected to column chromatography (dichloromethane:methanol=50:1 to 10:1) to obtain 0.42 g of the compound as a white solid, with a yield of 93.4% and HPLC >99%. MS: m/z (770.85), Found: 771.50 (M+H)⁺.

Example 33: Example 33 Synthesis of Compound ET770

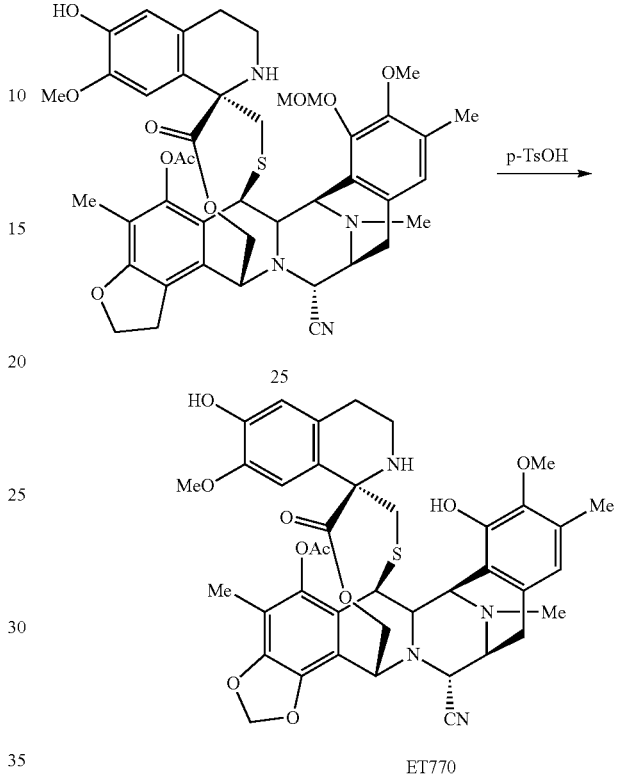

With reference to the method of example 32, compound ET770 is prepared, with a yield of 92.8% and HPLC >99%.
¹HNMR (400MHZ, CDCl₃): δ6.59 (s, 1H), 6.47 (s, 1H), 6.44 (s, 1H), 6.05 (d, J=1.2 Hz, 1H), 5.98 (d, J=1.2 Hz, 1H), 5.75 (s, 1H), 5.44 (bs, 1H), 5.03 (d, J=11.6 Hz, 1H), 4.57 (bs, 1H), 4.32 (s, 1H), 4.28 (d, J=4.8 Hz, 1H), 4.18 (d, J=2.8 Hz, 1H), 4.13 (dd, J1=2.0 Hz, J2=11.6 Hz, 1H), 3.79 (s, 3H), 3.62 (s, 3H), 3.51 (d, J=5.2 Hz, 1H), 3.42 (m, 1H), 3.12 (m, 1H), 2.95 (m, 21H), 2.79 (m, 1H), 2.60 (m, 1H), 2.49 (m, 1H), 2.36-2.11 (m, 2H), 2.32 (s, 3H), 2.26 (s, 3H), 2.19 (s, 3H), 2.04 (s, 3H); MS: m/z (770.85), Found: 771.50 (M+H)⁺.

Example 34: Example 34 Synthesis of Compound 26

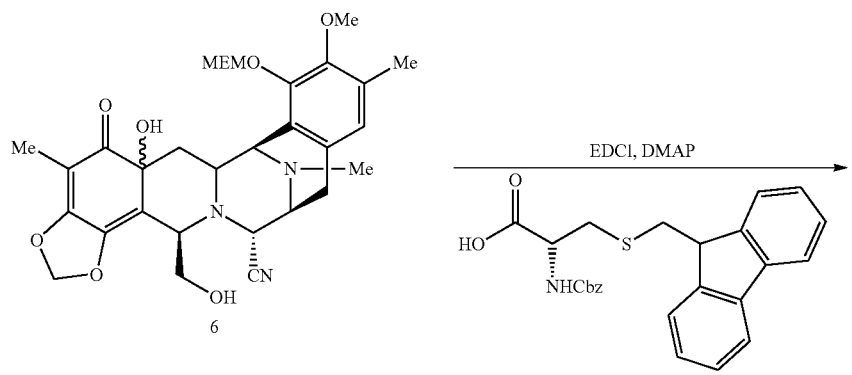

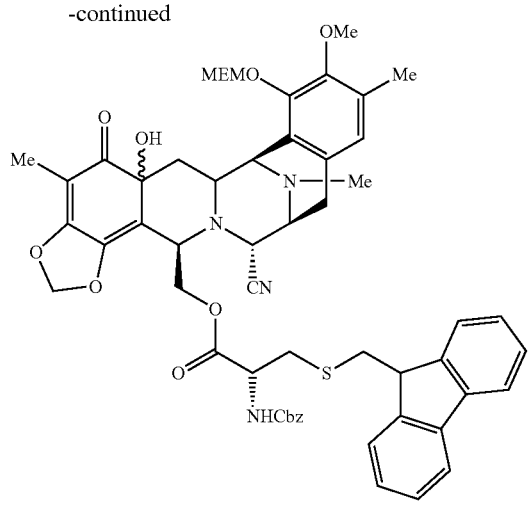

26

With reference to a similar method to example 7, wherein the N-tert-butoxycarbonyl-(s)-fluorenylmethyl-L-cysteine in the method of example 7 is replaced by N-benzyloxycarbonyl-(s)-fluorenylmethyl-L-cysteine, compound 26 is prepared and obtained as a light yellow solid, with a yield of 93.5% and HPLC >96%.

$^1$HNMR (400MHZ, CDCl$_3$): δ7.73 (d, J=7.6 Hz, 2H), 7.63 (d, J=7.6 Hz, 2H), 7.40-7.29 (m, 9H), 6.59 (s, 1H), 6.52 (s, 1H), 5.68 (s, 1H), 5.66 (s, 1H), 5.58 (s, 1H), 5.56 (s, 1H), 5.23 (d, J=6.0 Hz, 1H), 5.15-5.05 (m, 4H), 4.76-4.68 (m, 1H), 4.64-4.55 (m, 1H), 4.40 (m, 1H), 4.15-3.68 (m, 8H), 3.60 (s, 3H), 3.57 (s, 3H), 3.39 (s, 3H), 3.36 (s, 3H), 3.25-2.78 (m, 7H), 2.38-2.24 (m, 2H), 2.20 (s, 3H), 2.18 (s, 3H), 2.15 (s, 3H), 2.09 (m, 11H), 2.04 (s, 3H), 1.77 (s, 3H), 1.58 (s, 3H); MS: m/z (999.13), Found: 1000.05 (M+H)$^+$.

Example 35: Example 35 Synthesis of Compound 27

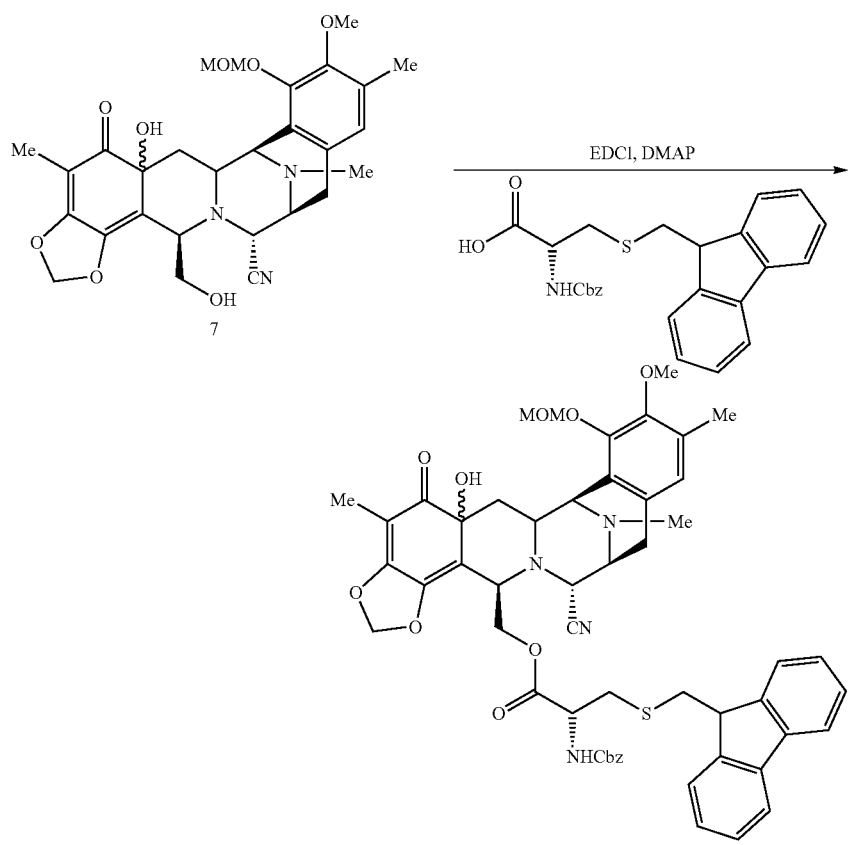

27

With reference to a similar method to example 8, wherein the N-tert-butoxycarbonyl-(s)-fluorenylmethyl-L-cysteine in the method of example 8 is replaced by N-benzyloxycarbonyl-(s)-fluorenylmethyl-L-cysteine, compound 27 is prepared and obtained as a light yellow solid, with a yield of 90.4%.

¹HNMR (400MHZ, CDCl₃): δ7.73 (d, J=7.6 Hz, 2H), 7.59 (m, 2H), 7.40-7.28 (m, 9H), 6.60 (s, 1H), 5.69 (s, 1H), 5.65 (s, 1H), 5.54 (d, J=7.6 Hz, 1H), 5.11-5.08 (m, 4H), 4.52 (m, 1H), 4.21-3.90 (m, 6H), 3.83 (s, 3H), 3.49 (s, 3H), 3.21 (d, J=6.4, 1H), 3.09-2.90 (m, 6H), 2.41 (d, J=18.0 Hz, 1H), 2.34-2.31 (m, 1H), 2.25 (s, 3H), 2.19 (s, 3H) 1.88-1.83 (m, 1H), 1.77 (s, 3H); MS: m/z (955.08.), Found: 956.0 (M+H)⁺.

Example 36: Example 36 Synthesis of Compound 28

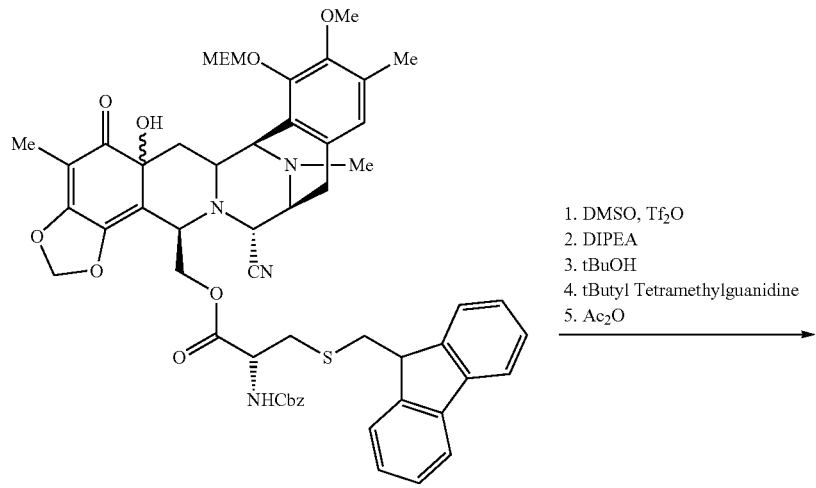

1. DMSO, Tf₂O
2. DIPEA
3. tBuOH
4. tButyl Tetramethylguanidine
5. Ac₂O

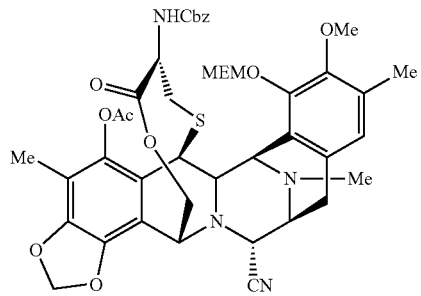

Under argon protection, to a 250 ml three-necked flask, 1.37 g of dimethyl sulfoxide and 140 ml of anhydrous dichloromethane are added, and 1.48 g of trifluoromethanesulfonic anhydride (5.25 mmol) is dropwise added at −70° C. to −80° C.; after the dropwise addition is completed, the reaction is stirred for 20 minutes with the temperature being maintained constant, and a solution of 3.5 g of compound 26 (3.50 mmol) in dichloromethane is dropwise added, with the internal temperature being controlled to not exceed −70° C. during the dropwise addition; after the dropwise addition is completed, the temperature is raised to −45° C. to −40° C. for 50 minutes of reaction, and 4.53 g of diisopropylethylamine (35.05 mmol) is then dropwise added; after the dropwise addition is completed, the temperature is slowly raised to 0° C. and then reduced to −15° C. or less, and 1.17 g of tert-butanol (15.78 mmol) is added; the mixture is stirred for 10 minutes with the temperature being maintained constant, and a solution of 6.0 g of 2-tert-butyl-1, 1,3,3-tetramethylguanidine (35.03 mmol) in dichloromethane is added; the temperature is slowly raised to 0° C. and then reduced to −10° C. or less, and 4.47 g of acetic anhydride (44.22 mmol) is slowly dropwise added; and after the dropwise addition is completed, a reaction is carried out for 15 minutes with the temperature being maintained constant, quenched by adding a saturated ammonium chloride aqueous solution and allowed for layering, and the aqueous layer is extracted with 100 ml of dichloromethane. The organic layers are combined, washed with a saturated sodium bicarbonate aqueous solution and a saturated sodium chloride aqueous solution respectively, concentrated and subjected to column chromatography (n-hexane:ethyl acetate=5:1 to 3:1) to obtain a white powdery solid, with a yield of 77.4% and HPLC >95%.

¹HNMR (400MHZ, CDCl₃): δ7.37 (m, 5H), 6.66 (s, 1H), 6.09 (s, 1H), 5.99 (s, 1H), 5.30 (d, J=5.6 Hz, 1H), 5.17 (d, J=6.0 Hz, 1H), 5.06 (d, J=7.6 Hz, 1H), 5.00 (s, 1H), 4.83 (d, J=9.2 Hz, 1H), 4.50 (s, 1H), 4.34-4.17 (m, 7H), 3.90-3.87 (m, 2H), 3.66 (s, 3H), 3.65-3.56 (m, 2H), 3.37 (s, 3H), 2.90 (m, 2H), 2.28 (s, 3H), 2.18 (s, 3H), 2.15-2.04 (m, 2H), 2.03 (s, 3H), 1.99 (s, 3H; MS: m/z (844.93), Found: 845.75 (M+H)⁺.

Example 37: Example 37 Synthesis of Compound 29

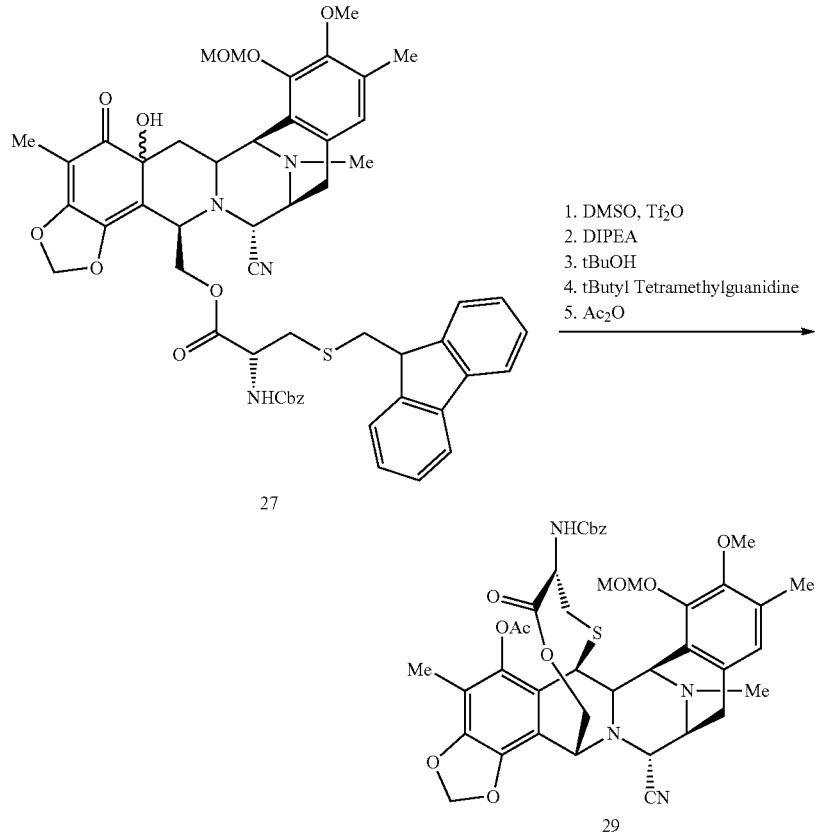

With reference to a similar method to example 36, compound 29 is prepared and obtained as a white powdery solid, with a yield of 72.6%.

$^1$HNMR (400MHZ, CDC$_3$): δ7.37 (m, 5H), 6.67 (s, 1H), 6.08 (d, J=1.2, 1H), 5.99 (d, J=1.2 Hz, 1H), 5.19-5.00 (m, 4H), 4.82 (d, J=9.2 Hz, 1H), 4.49 (s, 1H), 4.32-4.15 (m, 5H), 3.66 (s, 3H), 3.55 (s, 3H), 3.44 (d, J=4.8 Hz, 1H), 3.39 (d, J=6.0 Hz, 1H), 2.90 (m, 2H), 2.28 (s, 3H), 2.19 (s, 3H), 2.15-2.07 (m, 2H), 2.03 (s, 3H), 1.99 (s, 3H); MS: m/z (800.87), Found: 801.50 (M+H)$^+$.

Example 38: Example 38 Synthesis of Compound 20

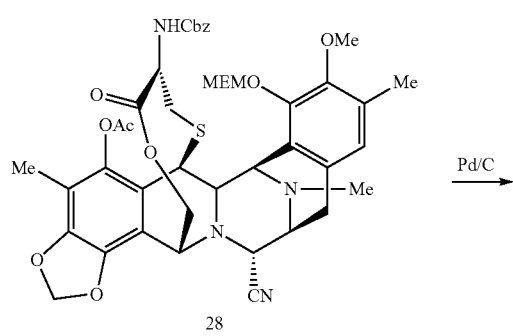

-continued

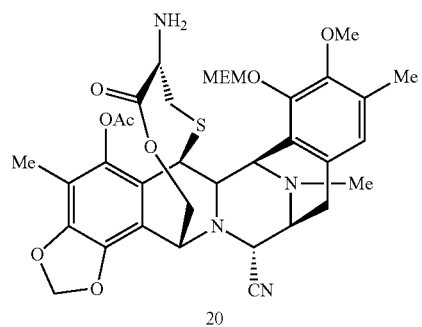

Under argon protection, 1.5 g of compound 28 (1.78 mmol), 30 ml of methanol and 1.0 ml of formic acid are added to a 100 ml three-necked flask; the temperature is reduced to 0° C. to 5° C., and 0.4 g of 10% Pd/C is added in three portions; after the addition is completed, the mixture is stirred for 1.5 hours with the temperature being maintained constant, filtered, dissolved by adding 100 ml of dichloromethane, washed sequentially with a saturated sodium bicarbonate aqueous solution and a saturated sodium chloride aqueous solution, dried over anhydrous sodium sulfate, concentrated and subjected to column chromatography (dichloromethane:methanol=50:1 to 10:1) to obtain 1.1 g of the compound as a white foamy solid, with a yield of 87.2% and HPLC >96%. MS: m/z (710.79), Found: 711.55 (M+H)⁺.
Example 39: Example 39 Synthesis of Compound 21
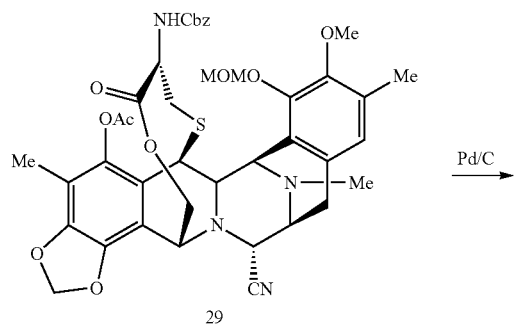
29
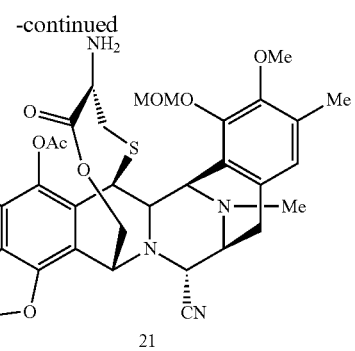
21
With reference to a similar method to example 38, compound 21 is prepared and obtained as a white foamy solid, with a yield of 86.1% and HPLC >95%.
MS: m/z (666.74), Found: 667.65 (M+H)⁺.
Example 40: Example 40 Synthesis of Compound 30
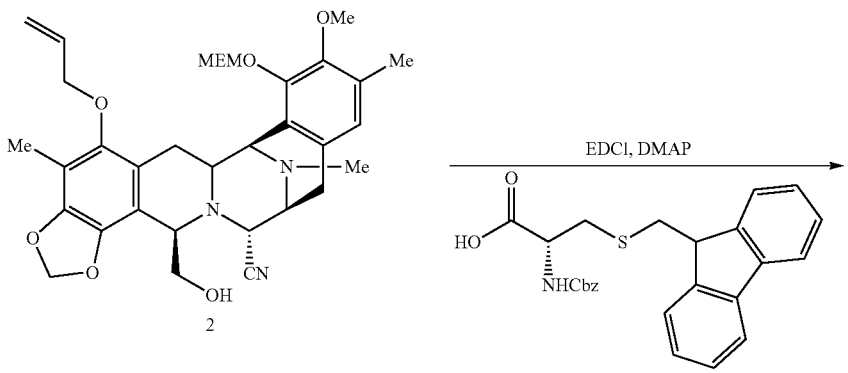
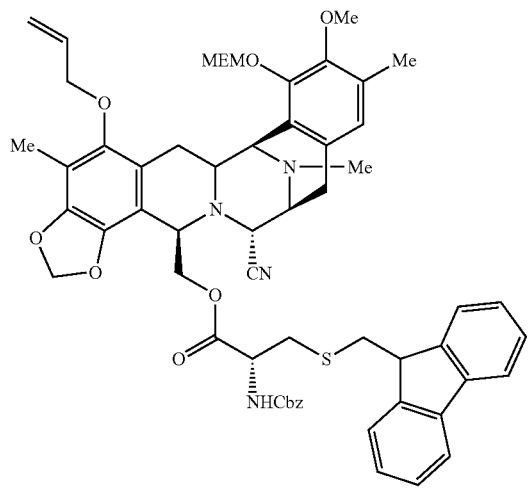
30

With reference to a similar method to example 16, wherein the N-tert-butoxycarbonyl-(s)-fluorenylmethyl-L-cysteine in the method of example 16 is replaced by N-benzyloxycarbonyl-(s)-fluorenylmethyl-L-cysteine, 8.2 g of compound 30 is prepared and obtained as a white foamy solid, with a yield of 97.4%. MS: m/z (1023.20), Found: 1024.0 (M+H)$^+$.

With reference to a similar method, compound 38 and compound 39 are prepared.

Example 41: Example 41 Synthesis of Compound 31

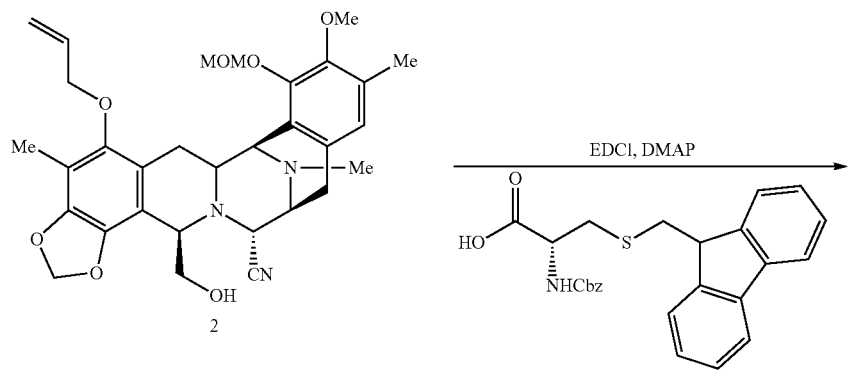

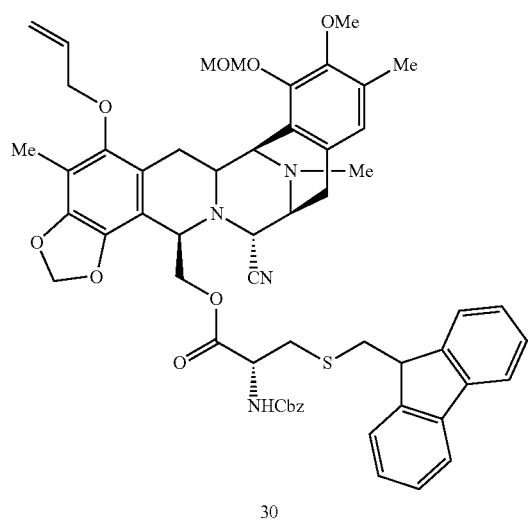

With reference to a similar method to example 16, compound 30 is prepared and obtained as a white foamy solid, with a yield of 94.4%.

MS: m/z (979.15), Found: 980.0 (M+H)$^+$.

Example 42: Example 42 Synthesis of Compound 32
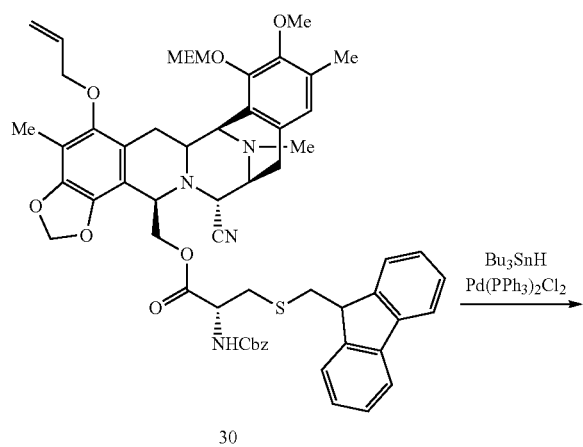
30
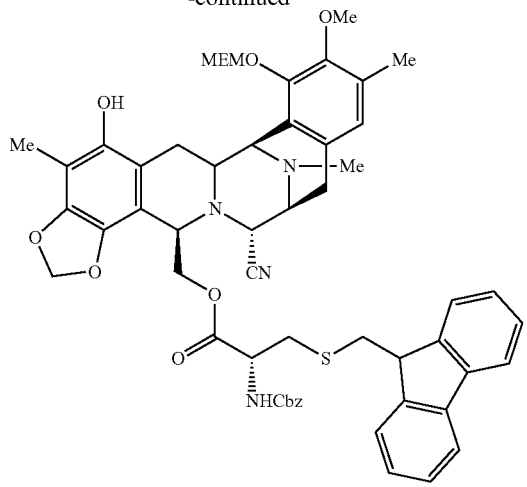
32
With reference to a similar method to example 18, compound 32 is prepared and obtained as a white foamy solid, with a yield of 93.6%.
$^1$HNMR (400MHZ, CDCl$_3$): δ7.71 (d, J=7.2, 2H), 7.59 (d, J=7.6 Hz, 1H), 7.53 (d, J=7.6 Hz, 11H), 7.41-7.23 (m, 9H), 6.60 (s, 1H), 5.87 (bs, 2H), 5.74 (s, 1H), 5.40 (d, J=6.4 Hz, 1H), 5.33 (d, J=6.0 Hz, 1H), 5.18 (d, J=9.2 Hz, 1H), 5.09 (d, J=12 Hz, 11H), 4.97 (d, J=12 Hz, 11H), 4.56 (dd, J1=3.2 Hz, J2=11.2 Hz, 1H), 4.19 (d, J=2.0 Hz, 1H), 4.16-3.87 (m, 9H), 3.6 (s, 3H), 3.38 (s, 3H), 3.32-3.20 (m, 3H), 2.96-2.87 (m, 3H), 2.62-2.54 (m, 2H), 2.28 (s, 3H), 2.19 (s, 3H), 1.97 (s, 3H), 1.82 (dd, J1=13.2 Hz, J2=15.6 Hz, 1H).
Example 43: Example 43 Synthesis of Compound 34
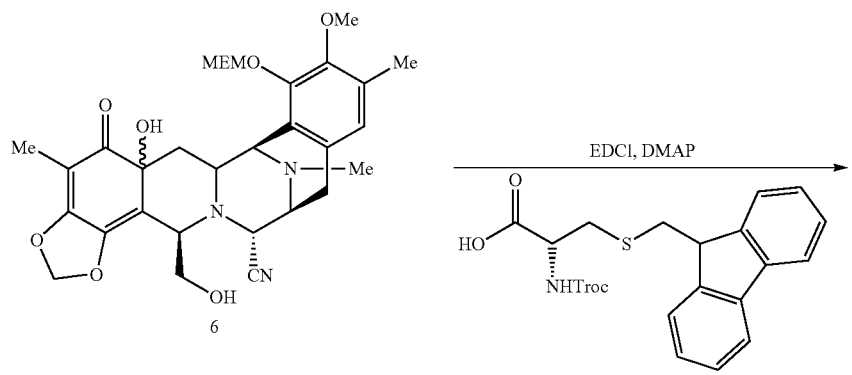

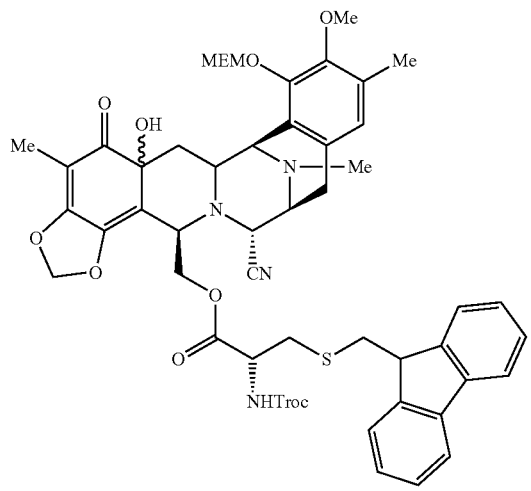

34

2.5 g of compound 6 (4.28 mmol) and 3.3 g of N-(2,2,2)-trichloroethyloxycarbonyl-(s)-fluorenylmethyl-L-cysteine (6.95 mmol) are dissolved in dichloromethane, and treated with anhydrous toluene (2×20 ml), and water is azeotropically removed. Under argon protection, the mixture from which water has been removed is dissolved in 50 ml of dichloromethane, transferred to a 250 ml three-necked flask, and cooled to −10° C. or less; 0.262 g of DMAP (2.14 mmol) is added, and a solution of 1.64 g of 1-ethyl-(3-dimethylaminopropyl)carbodiimide hydrochloride (EDC hydrochloride) (8.57 mmol) in dichloromethane is dropwise added; after the dropwise addition is completed, the reaction is stirred at 10° C. to 15° C. for 2 hours, quenched by adding a saturated sodium bicarbonate aqueous solution and allowed for layering; the aqueous layer is extracted with dichloromethane (2×50 ml), and the organic layers are combined, dried over anhydrous sodium sulfate, and concentrated in vacuo to obtain an oil, which is subjected to column chromatography (n-hexane:ethyl acetate=4:1 to 1:1) to obtain 3.8 g of the compound as a light yellow solid, with a yield of 85.3%. MS: m/z (1040.40), Found: 1040.25 (M+H)$^+$.

Example 44: Example 44 Synthesis of Compound 35

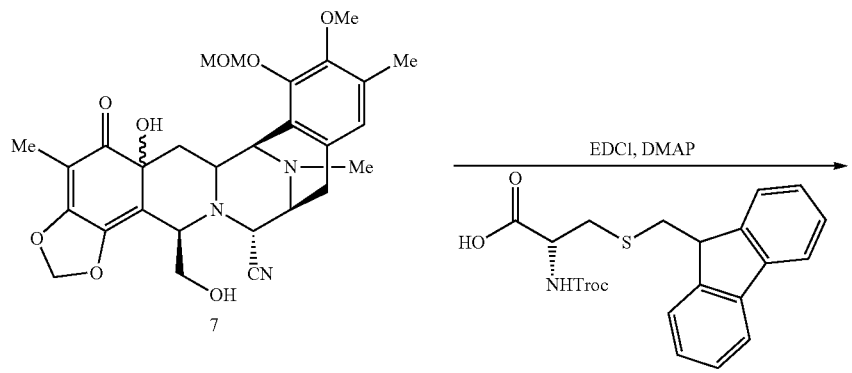

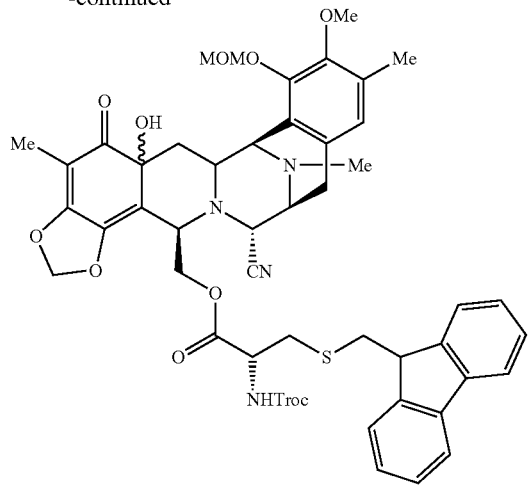
35
With reference to a similar method to example 43, compound 35 is prepared from compound 7 and obtained as a light yellow solid, with a yield of 96.7%.
$^1$HNMR (400MHZ, CDCl$_3$): δ 7.76 (m, 4H), 7.65 (m, 4H), 7.39 (m, 4H), 7.29 (m, 4H), 6.62 (s, 1H), 6.55 (s, 1H), 5.79-5.63 (m, 6H), 5.09 (s, 1H), 5.02 (d, J=6.0, 1H), 4.99 (d, J=6.0 Hz, 1H), 4.80-4.63 (m, 6H), 4.60 (m, 1H), 4.50 (m, 1H), 4.38 (dd, J1=7.6, J2=12.8 Hz, 1H), 4.27 (dd, J1=7.6, J2=12.8, 1H), 4.16-3.90 (m, 1 OH), 3.84 (s, 3H), 3.62 (s, 3H), 3.50 (s, 3H), 3.33-2.83 (m, 14H), 2.45-2.18 (m, 2H), 2.21 (s, 6H), 2.17 (s, 6H), 1.77 (s, 6H), 1.67 (m, 2H).
Example 45: Example 45 Synthesis of Compound 37
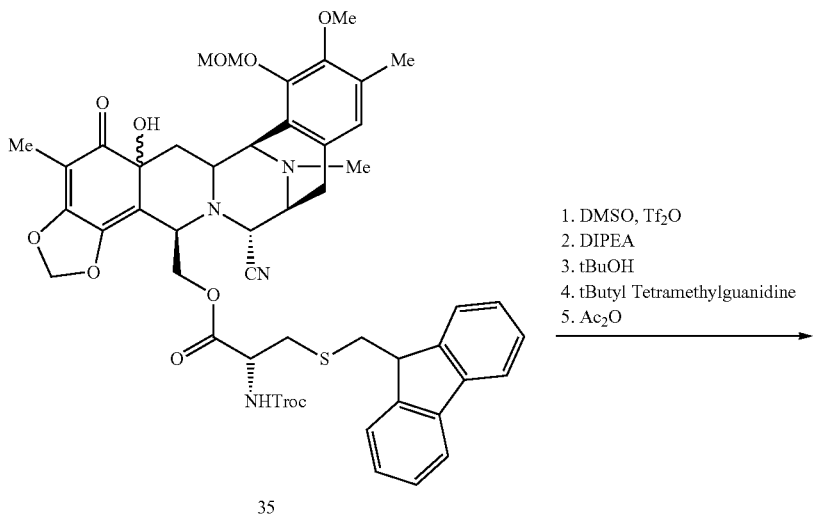
35
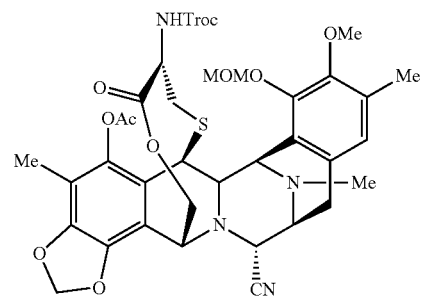
37

Under argon protection, to a 100 ml three-necked flask, 0.85 g of dimethyl sulfoxide (10.86 mmol) and 60 ml of anhydrous dichloromethane are added, and 0.80 g of trifluoromethanesulfonic anhydride (2.82 mmol) is added at −70° C. to −80° C.; after the dropwise addition is completed, the reaction is stirred for 20 minutes with the temperature maintained constant, and a solution of 2.1 g of compound 9 (2.17 mmol) in dichloromethane is dropwise added, with the internal temperature being controlled to not exceed −70° C. during the dropwise addition; after the dropwise addition is completed, the temperature is raised to −45° C. to −40° C. for 50 minutes of reaction, and 2.81 g of diisopropylethylamine (21.71 mmol) is then dropwise added; after the dropwise addition is completed, the temperature is slowly raised to 0° C. and then reduced to −15° C. or less, and 0.72 g of tert-butanol (9.77 mmol) is added; the mixture is stirred for 10 minutes with the temperature being maintained constant, and a solution of 3.72 g of 2-tert-butyl 1,1,3,3-tetramethylguanidine (21.71 mmol) in dichloromethane is added; the temperature is slowly raised to 0° C. and then reduced to −10° C. or less, and 2.77 g of acetic anhydride (27.14 mmol) is slowly dropwise added; and after the dropwise addition is completed, a reaction is carried out for 15 minutes with the temperature being maintained constant, quenched by adding a saturated ammonium chloride aqueous solution, and allowed for layering, and the aqueous layer is extracted with 50 ml of dichloromethane. The organic layers are combined, washed with a saturated sodium bicarbonate aqueous solution and a saturated sodium chloride aqueous solution respectively, concentrated and subjected to column chromatography (n-hexane:ethyl acetate=10:1 to 1:1) to obtain a white powdery solid, with a yield of 79.1%.

$^1$HNMR (400MHZ, CDCl$_3$): δ6.85 (s, 1H), 6.09 (s, 1H), 5.99 (s, 1H), 5.20 (d, J=5.6 Hz, 1H), 5.14 (d, J=5.2 Hz), 5.03 (m, 1H), 4.82 (d, J=12.4 Hz, 1H), 4.63 (d, J=12.0 Hz, 1H), 4.52 (m, 1H), 4.35-4.17 (m, 4H), 3.76 (s, 3H), 3.56 (s, 3H), 3.45 (m, 2H), 2.91 (m, 2H), 2.32 (s, 3H), 2.28 (s, 3H), 2.21 (s, 3H), 2.12 (m, 2H), 2.03 (s, 3H).

With reference to a similar method, compound 36 is prepared, with a yield of 73.5%. MS: m/z (886.14), Found: 887.2 (M+H)$^+$.

Example 46: Example 46 Synthesis of Compound 21

Under argon protection, 1.0 g of compound 37 is dissolved in 25 ml of a 90% acetic acid aqueous solution, and 0.8 g of zinc powder is added; the mixture is stirred at 20° C. to 25° C. for 36 hours and filtered over diatomaceous earth; the filter cake is washed with dichloromethane, and the filtrate is added 100 ml of dichloromethane, washed with a saturated sodium bicarbonate aqueous solution and a saturated sodium chloride aqueous solution, dried over anhydrous sodium sulfate, concentrated and subjected to column chromatography (dichloromethane:methanol=50:1 to 10:1) to obtain 0.69 g of the compound as a white foamy solid, with a yield of 87.2% and HPLC >95%.

$^1$HNMR (400MHZ, CDCl$_3$): δ 6.73 (s, 1H), 6.08 (d, J=1.2 Hz, 1H), 5.99 (d, J=1.2 Hz, 1H), 5.93 (m, 1H), 5.21 (d, J=3.6 Hz, 1H), 5.14 (d, J=3.6 Hz, 1H), 5.02 (d, J=12.0 Hz, 1H), 4.51 (m, 1H), 4.34 (d, J=4.8 Hz, 1H), 4.27 (s, 1H), 4.20 (d, J=3.2, 1H), 4.13 (d, J=12 Hz, 1H), 3.79 (s, 3H), 3.57 (s, 3H), 3.45 (d, J=4.8 Hz, 1H), 3.41 (m, 1H), 3.31 (m, 1H), 2.92 (m, 2H), 2.29 (s, 31H), 2.25 (s, 3H), 2.19 (s, 3H), 2.16 (m, 11H), 2.04 (s, 3H).

With reference to a similar method, compound 36 is prepared, with a yield of 83.5%. MS: m/z (710.2), Found: 711.0 (M+H)$^+$.

Example 47: Example 47: Study on the Effects of Different Reaction Conditions on the Preparation of Compound QT9

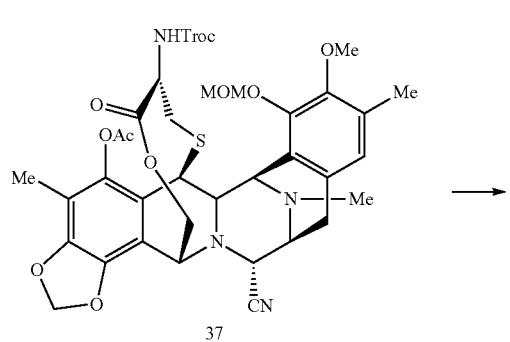

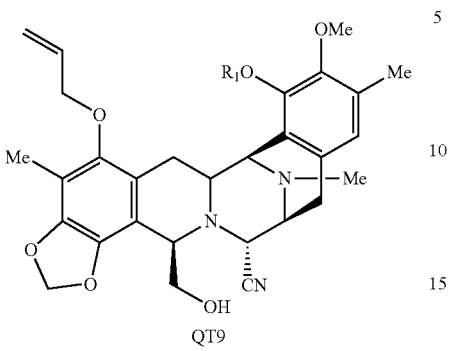

QT9 in which R₁ is MEM or MOM; with reference to a similar method to examples 1 and 2, compound QT9 is prepared from compound QT10, wherein the material charge amounts are shown as in the following table.

| Batch No. | Compound QT10 amount | Type and amount of base | Protecting agent (MEMCl or MOMBr) and amount thereof | Reaction temperature | Reaction situation |
|---|---|---|---|---|---|
| 1 | 1 eq | K₂CO₃, 30 eq | 20 eq | 20° C. to 30° C. | Yield > 50%; TLC results show the existence of impurities |
| 2 | 1 eq | K₂CO₃, 8 eq | 12 eq | 5° C. to 10° C. | Yield > 60%; the double-protected by-product has a content of 19.2% |
| 3 | 1 eq | DIPEA, 1 eq | 15 eq | 0° C. to 10° C. | Yield > 50%; TLC results show the existence of impurities |
| 4 | 1 eq | NaH, 1.0 eq | 2.0 eq | −10° C. to 0° C. | Yield > 85%; the double-protected by-product has a content of 1.3% |
| 5 | 1 eq | NaH, 1.5 eq | 1.5 eq | 5° C. to 10° C. | Yield > 85%; the double-protected by-product has a content of 1.8% |
| 6 | 1 eq | NaH, 1.2 eq; t-KOBu, 1.0 eq | 2.5 eq | 0° C. to 5° C. | Yield > 80%; the double-protected by-product has a content of 6.5% |
| 7 | 1 eq | t-KOBu, 3 eq | 5 eq | 5° C. to 10° C. | Yield > 80%; the double-protected by-product has a content of 6.017% |
| 8 | 1 eq | t-KOBu, 1.0 eq | 1 eq | 15° C. to 25° C. | Yield > 85%; the double-protected by-product has a content of 4.16% |
| 9 | 1 eq | t-KOBu, 5 eq | 5 eq | −5° C. to 5° C. | Yield > 80%; the double-protected by-product has a content of 7.1% |
| 10 | 1 eq | t-KOBu, 5 eq | 15 eq | −10° C. to 0° C. | Yield > 50%; TLC results show the existence of impurities |
| 11 | 1 eq | n-LiOBu, 10 eq | 10 eq | −10° C. to 15° C. | Yield > 75%; the double-protected by-product has a content of 16.8% |
| 12 | 1 eq | KOH, 2.0 eq | 2 eq | 5° C. to 15° C. | Yield > 85%; the double-protected by-product has a content of 1.7% |
| 13 | 1 eq | KOH, 15 eq | 5 eq | 0° C. to 10° C. | Yield > 85%; the double-protected by-product has a content of 5.7% |
| 14 | 1 eq | LiOCH₃, 2.0 eq | 2.0 eq | 0° C. to 10° C. | Yield > 80%; the double-protected by-product has a content of 6.41% |
| 15 | 1 eq | NaOH, 4.0 eq | 2.0 eq | 0° C. to 10° C. | Yield > 90%; the double-protected by-product has a content of <1% |

-continued

| Batch No. | Compound QT10 amount | Type and amount of base | Protecting agent (MEMCl or MOMBr) and amount thereof | Reaction temperature | Reaction situation |
|---|---|---|---|---|---|
| 16 | 1 eq | NaOH, 2.5 eq | 2.0 eq | 5° C. to 10° C. | Yield > 95%; the double-protected by-product has a content of <1% |
| 17 | 1 eq | NaOH, 1 eq | 2.0 eq | 0° C. to 5° C. | Yield > 95%; the double-protected by-product has a content of <1% |

In the table, eq stands for molar equivalent.

As can be seen from the reaction conditions in the above table, where the base is potassium t-butoxide, lithium methoxide, potassium hydroxide, lithium t-butoxide, etc., the corresponding compound QT9 can be prepared in all these cases; in addition, where NaOH, KOH, NaH or a mixture thereof is preferably selected as the base, the molar ratio of the compound QT10 to the base is 1:1 to 10, particularly 1 to 2.5, and the molar ratio of the compound QT10 to the hydroxyl protecting agent is 1:1 to 10, particularly 1 to 2.5, a very good effect can be achieved, and the double-protected impurities can be controlled to less than 2%; moreover, a majority of the double-protected impurities may be further removed by means of recrystallization, such that the purity of the target product reaches 99% or more; furthermore, taking into account safety issues in the industrial production process, sodium hydroxide is the most preferred, and the use of sodium hydroxide results in a high conversion rate, a smaller content of side reaction impurities, and a higher safety than sodium hydride. It can also be seen from the above comparative experiment that where sodium hydroxide is used, the amount thereof may fluctuate within a larger range.

What is claimed is:

1. A method for preparing compound QT9, comprising reacting compound QT10 with a hydroxyl protecting agent to obtain compound QT9:

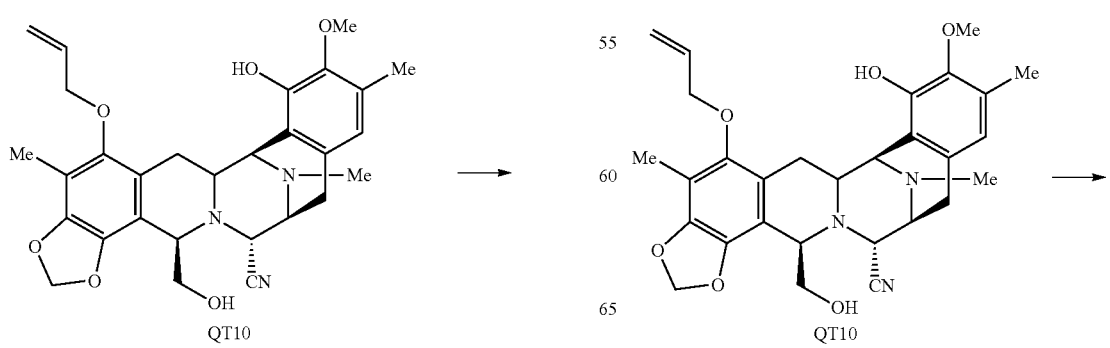

-continued

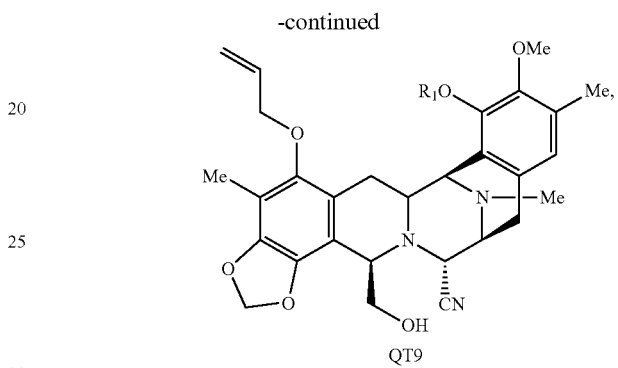

wherein $R_1$ of compound QT9 is a hydroxyl protecting group;
wherein, the compound QT10 is converted into compound QT9 under alkaline conditions using a base, and wherein the base is NaOH, KOH, NaH, LiOH, LiOCH$_3$, Na$_2$CO$_3$, K$_2$CO$_3$ or a mixture thereof.

2. The method according to claim 1, wherein the hydroxyl protecting group $R_1$ of compound QT9 is MOM, MEM, trimethylsilyl, tert-butyldimethylsilyl, or tert-butyldiphenylsilyl.

3. A method for preparing an ecteinascidin compound, comprising reacting compound QT10 with a hydroxyl protecting agent to obtain compound QT9:

-continued

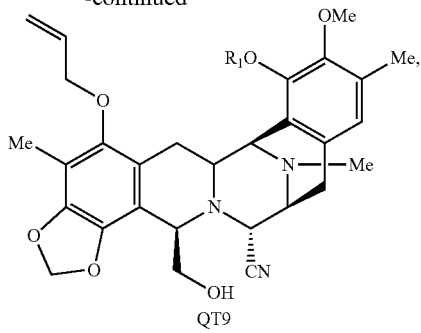
QT9 wherein $R_1$ of the compound QT9 is a hydroxyl protecting group;
wherein the hydroxyl protecting group $R_1$ of the compound QT9 is MOM, MEM, trimethylsilyl, tert-butyldimethylsilyl, or tert-butyldiphenylsilyl;
wherein the compound QT10 is converted into the compound QT9 under alkaline conditions using a base, and wherein the base is NaOH, KOH, NaH, LiOH, LiOCH$_3$, Na$_2$CO$_3$, K$_2$CO$_3$ or a mixture thereof.

4. The method according to claim 3, wherein the method further comprises selectively removing the allyl group from the compound QT9 to obtain compound QT8:

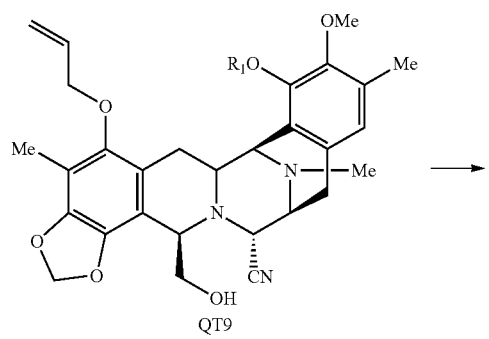
QT9

→

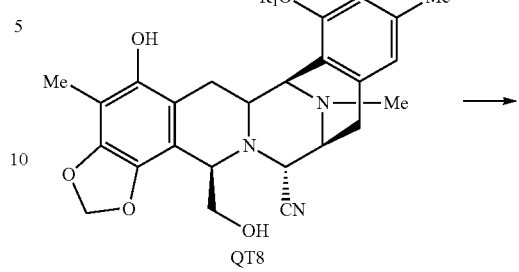
QT8

→

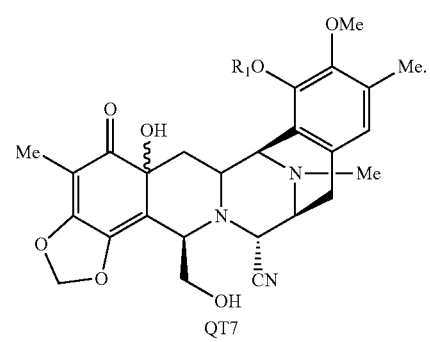
QT7

6. The method according to claim 5, wherein the method further comprises esterifying the primary hydroxyl group of the compound QT7 with a cysteine derivative to obtain compound QT6:

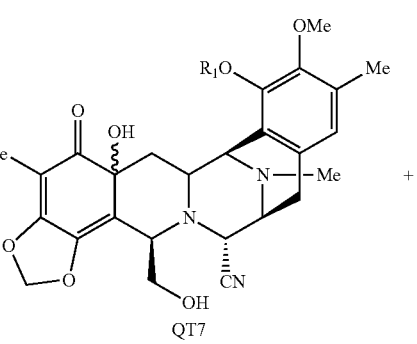
QT7
+

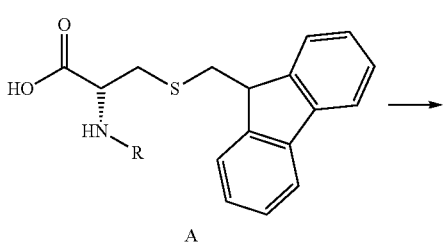
A
→

5. The method according to claim 4, wherein the method further comprises oxidizing the phenolic hydroxyl group of the compound QT8, and selectively hydroxylating the resulting oxidized form of the compound QT8 to obtain compound QT7:

-continued

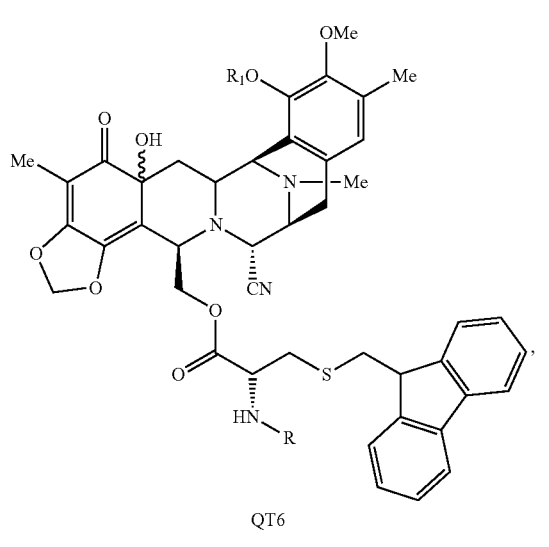

QT6 wherein R of the cysteine derivative and the compound QT6 is an amino protecting group which is Alloc, Cbz, Troc, or Boc.

7. The method according to claim 3, wherein the method further comprises esterifying the primary hydroxyl group of the compound QT9 with a cysteine derivative to obtain compound QT8A:

-continued

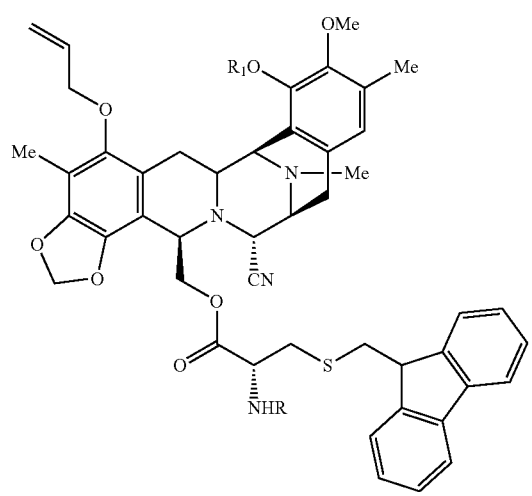

QT8A wherein R of the cysteine derivative and the compound QT8A is an amino protecting group which is Alloc, Cbz, Troc, or Boc.

8. The method according to claim 7, wherein the method further comprises selectively removing the allyl group from the compound QT8A to obtain compound QT7A:

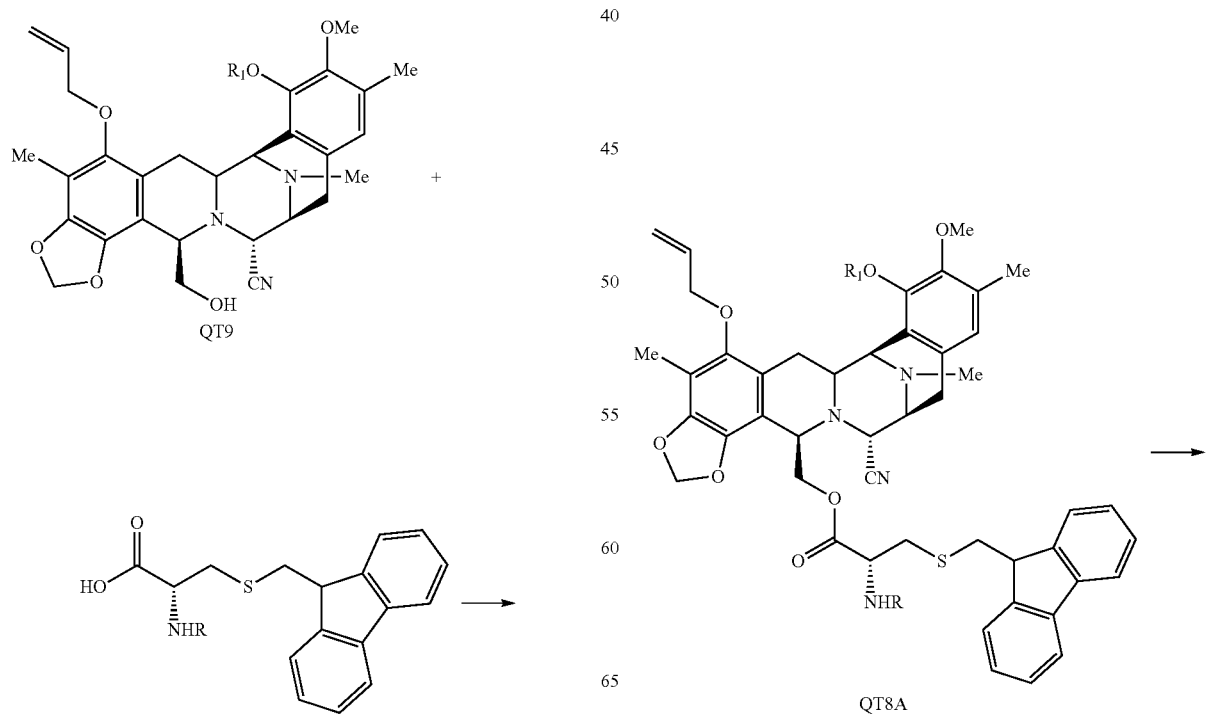

-continued

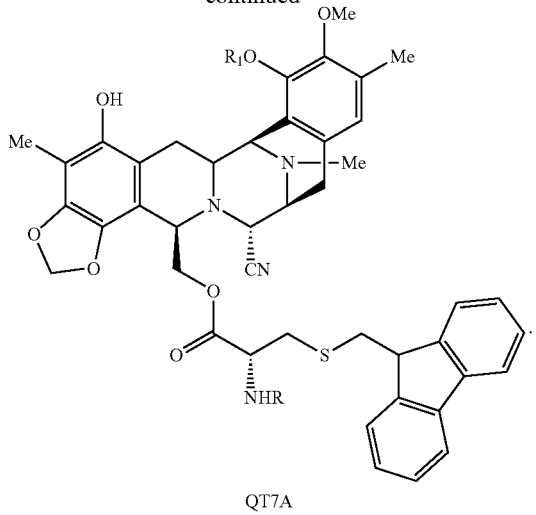

QT7A

9. The method according to claim 8, wherein the method further comprises oxidizing the phenolic hydroxyl group of the compound QT7A, and selectively hydroxylating the resulting oxidized form of the compound QT7A to obtain compound QT6:

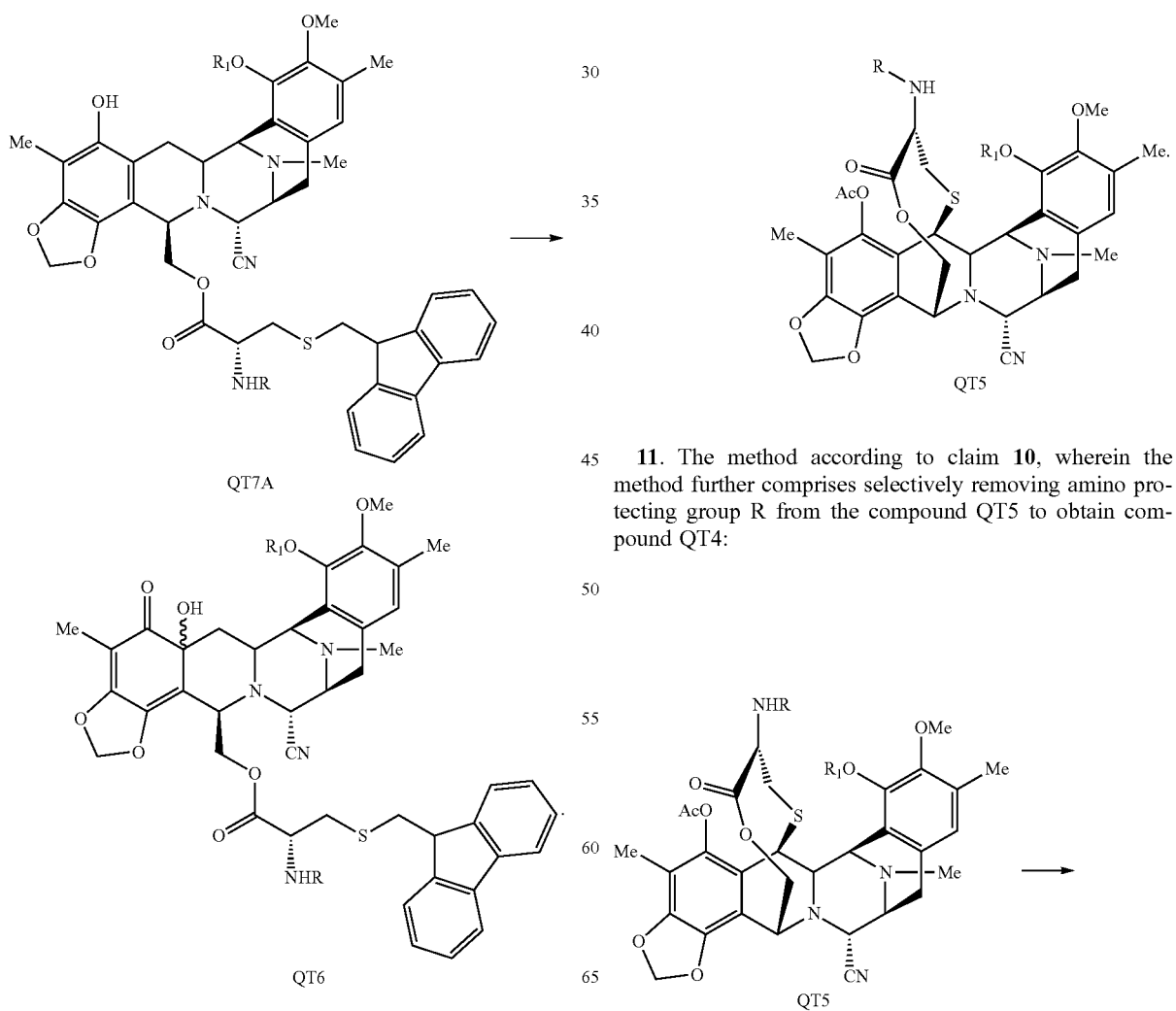

QT7A

QT6

10. The method according to claim 6, wherein the method further comprises reacting the compound QT6 with a Swern reagent and further with N-tert-butyl-N',N'-tetramethylguanidine to obtain 1,4-bridged lactone compound QT5:

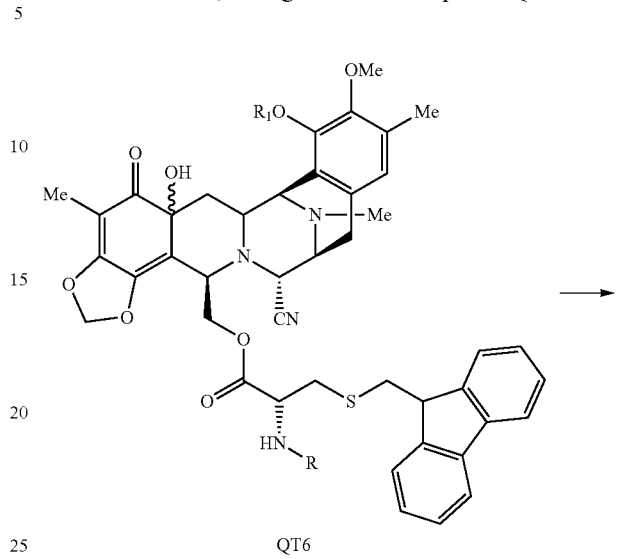

QT6

QT5

11. The method according to claim 10, wherein the method further comprises selectively removing amino protecting group R from the compound QT5 to obtain compound QT4:

QT5

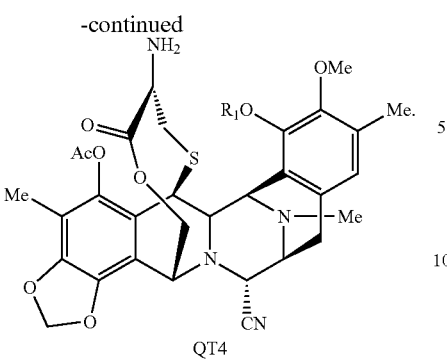

QT4

12. The method according to claim 11, wherein the method further comprises subjecting the compound QT4 to transamination conditions to obtain compound QT3:

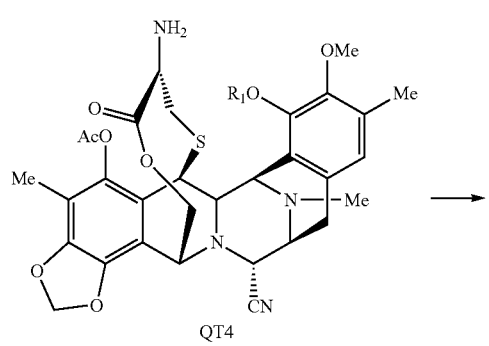

QT4

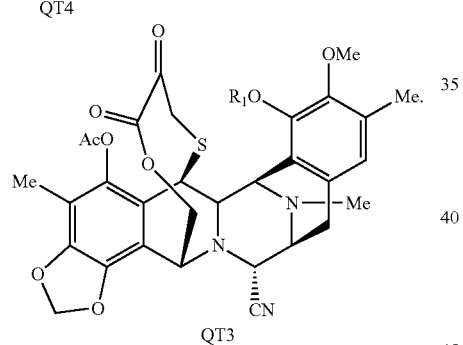

QT3

13. The method according to claim 12, wherein the method further comprises reacting the compound QT3 with 2-[3-hydroxy-4-methoxy-phenyl]ethylamine to obtain compound QT2, selectively removing the phenol hydroxyl protecting group $R_1$ from the compound QT2 to obtain compound ET770, and optionally converting the CN group in the compound ET770 into an OH group to obtain compound ET743:

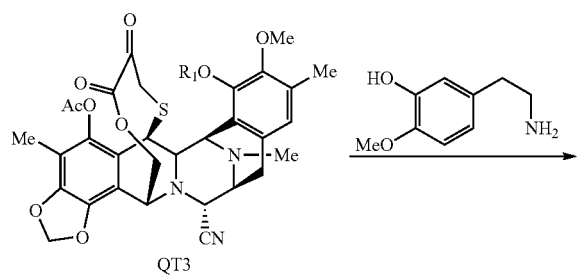

QT3

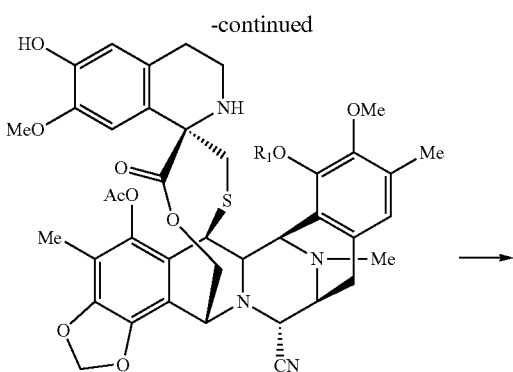

QT2

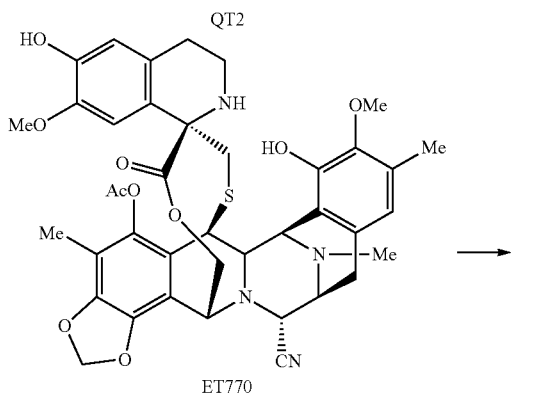

ET770

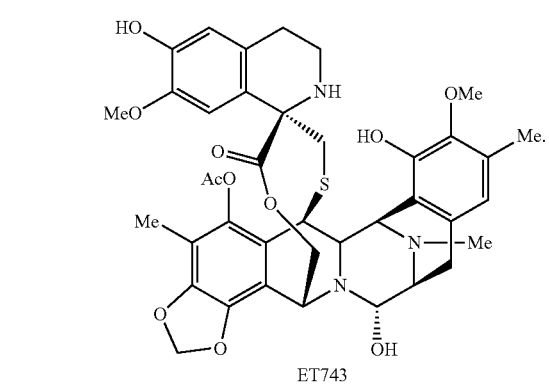

ET743

14. The method according to claim 10, wherein the method further comprises simultaneously removing the amino protecting group R and the hydroxyl protecting group $R_1$ from the compound QT5 to obtain compound QT4A:

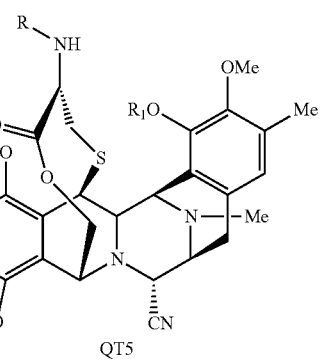

QT5

131
-continued

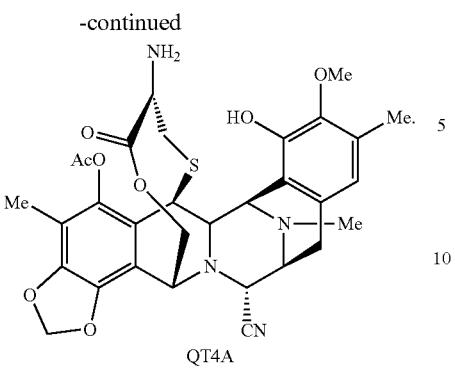

QT4A

132
-continued

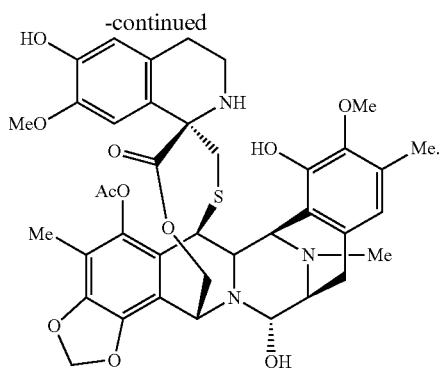

ET743

15. The method according to claim 14, wherein the method further comprises subjecting the compound QT4A to transamination conditions to obtain compound QT3A, and optionally reacting the compound QT3A with 2-[3-hydroxy-4-methoxy-phenyl]ethylamine to obtain compound ET770, and converting the CN group in the compound ET770 into an OH group to obtain compound ET743:

16. The method according to claim 6, wherein $R_1$ of the compound QT7 and the compound QT6 is MEM or MOM, and wherein R of the cysteine derivative and the compound QT6 is Alloc, Cbz, Troc or Boc.

17. The method according to claim 9, wherein the method further comprises reacting the compound QT6 with a Swern reagent and further with N-tert-butyl-N',N'-tetramethylguanidine to obtain 1,4-bridged lactone compound QT5:

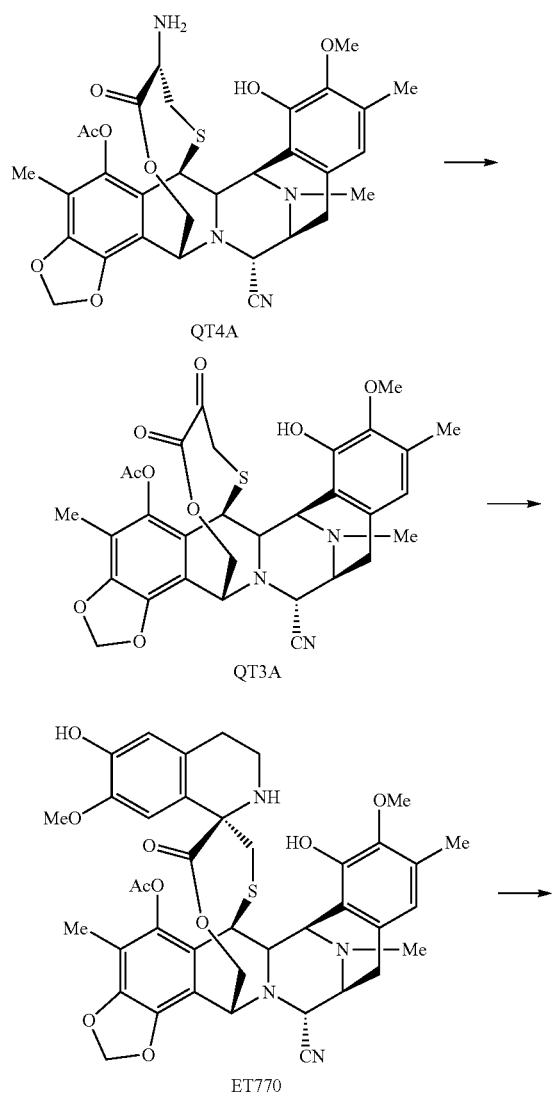

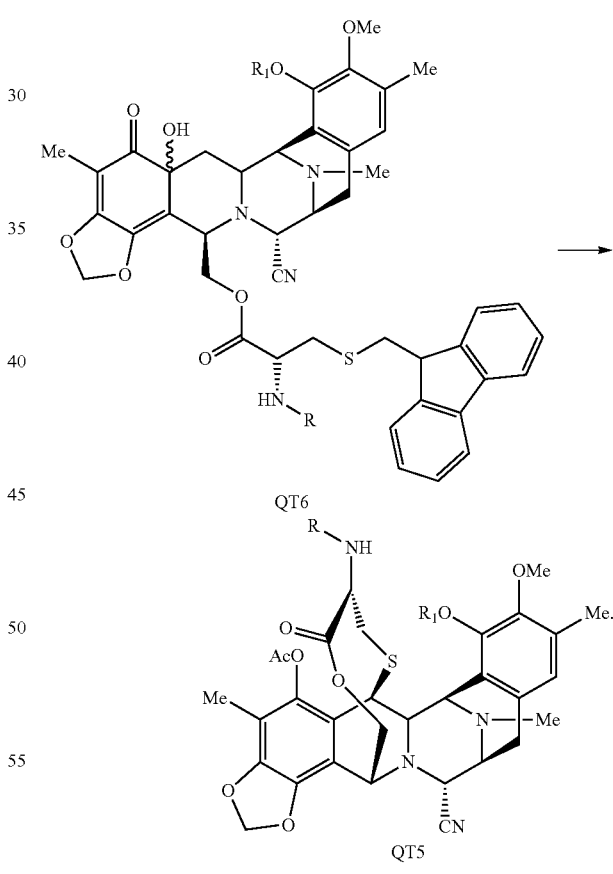

18. The method according to claim 14, wherein $R_1$ of compound QT5 is MEM or MOM, and wherein R of compound QT5 is Boc.

19. The method according to claim 1, wherein the hydroxyl protecting agent is bromomethyl methyl ether, chloromethyl methyl ether, or 2-methoxyethoxymethyl chloride, and the molar ratio of the compound QT10 to the hydroxyl protecting agent is 1:1 to 20, and wherein the molar ratio of the compound QT10 to the base is 1:1 to 30, and the reaction temperature is −10° C. to 30° C.

20. The method according to claim 1, wherein the molar ratio of the compound QT10 to the hydroxyl protecting agent is 1.5 to 2.5, and wherein the molar ratio of the compound QT10 to the base is 1.5 to 4, and the reaction temperature is 0° C. to 10° C.

21. The method according to claim 1, wherein the base is NaOH, KOH, NaH or a mixture thereof.

22. The method according to claim 3, wherein the hydroxyl protecting group $R_1$ is MOM or MEM.

23. The method according to claim 3, wherein the hydroxyl protecting agent is bromomethyl methyl ether, chloromethyl methyl ether, or 2-methoxyethoxymethyl chloride and the molar ratio of the compound QT10 to the hydroxyl protecting agent is 1:1 to 20, and wherein the molar ratio of the compound QT10 to the base is 1:1 to 30, and the reaction temperature is −10° C. to 30° C.

24. The method according to claim 23, wherein the molar ratio of the compound QT10 to the hydroxyl protecting agent is 1.5 to 2.5, and wherein the molar ratio of the compound QT10 to the base is 1.5 to 4, and the reaction temperature is 0° C. to 10° C.

25. The method according to claim 3, wherein the base is NaOH, KOH, NaH or a mixture thereof.

* * * * *